(12) United States Patent
Zacharie et al.

(10) Patent No.: US 8,258,295 B2
(45) Date of Patent: Sep. 4, 2012

(54) TRIAZINE DERIVATIVES, COMPOSITIONS CONTAINING SUCH DERIVATIVES, AND METHODS OF TREATMENT OF CANCER AND AUTOIMMUNE DISEASES USING SUCH DERIVATIVES

(75) Inventors: Boulos Zacharie, Laval (CA); Christopher Penney, Pierrefonds (CA); Lyne Gagnon, Laval (CA); Brigitte Grouix, Montreal (CA); Lilianne Geerts, Saint-Lazare (CA); Shaun D. Abbott, Pointe-Claire (CA)

(73) Assignee: Prometic Biosciences Inc., Laval (CA)

( * ) Notice: Subject to any disclaimer, the term of this patent is extended or adjusted under 35 U.S.C. 154(b) by 309 days.

(21) Appl. No.: 12/598,273

(22) PCT Filed: Apr. 25, 2008

(86) PCT No.: PCT/CA2008/000796
§ 371 (c)(1),
(2), (4) Date: Oct. 30, 2009

(87) PCT Pub. No.: WO2008/131547
PCT Pub. Date: Nov. 6, 2008

(65) Prior Publication Data
US 2010/0129350 A1    May 27, 2010

Related U.S. Application Data

(60) Provisional application No. 60/924,111, filed on Apr. 30, 2007.

(51) Int. Cl.
*C07D 251/70* (2006.01)
*A61K 31/53* (2006.01)
*A61P 35/00* (2006.01)
*A61P 37/00* (2006.01)
*A61P 25/28* (2006.01)
*A61P 19/02* (2006.01)
*A61P 17/06* (2006.01)

(52) U.S. Cl. ...................... 544/197; 514/245

(58) Field of Classification Search .............. 544/197; 514/245
See application file for complete search history.

(56) References Cited

U.S. PATENT DOCUMENTS

2009/0068169 A1*  3/2009  Penney et al. ............. 424/130.1
2009/0075867 A1*  3/2009  Gagnon et al. ................ 514/8

FOREIGN PATENT DOCUMENTS

CA        2216486 A1      4/1998
WO    WO 97/10887 A1    3/1997

OTHER PUBLICATIONS

Cha et al., Journal of Pharmacology and Experimental Therapeutics, 317(2), 571-578, 2006.*
Braselmann et al., Journal of Pharmacology and Experimental Therapeutics, 319(3), 998-1008, 2006.*
Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p4.*
Dermer et al., Bio/Technology, 1994, 12:320.*
Golub et al., Science, 286, 531-537, 1999.*
Cecil Textbook of Medicine, edited by Bennet, J.C., and Plum F., 20th edition,vol. 1, 1004-1010, 1996.*
International Preliminary Report on Patentability from International Application No. PCT/CA2008/000796, dated Nov. 12, 2009.

* cited by examiner

*Primary Examiner* — Venkataraman Balasubramanian
(74) *Attorney, Agent, or Firm* — France LeClaire

(57) ABSTRACT

We describe compounds of the following general formula (I): wherein X is fluorine or chlorine; Y is oxygen, sulfur, or an amino group; R is an amino, hydroxyl, sulfonamide, or carboxamide group or an N-monomethyl or N-dimethyl analog thereof; m is an integer from 2 to 6, and n is an integer from 0 to 2. The compounds may be used for treating certain cancers and autoimmune diseases.

(I)

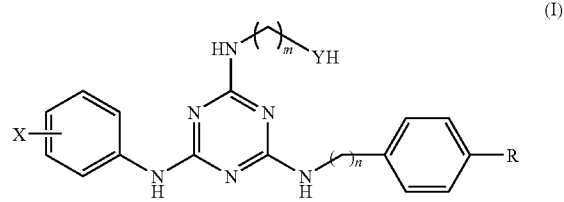

19 Claims, 28 Drawing Sheets

TRIAZINE DERIVATIVES, COMPOSITIONS CONTAINING SUCH DERIVATIVES, AND METHODS OF TREATMENT OF CANCER AND AUTOIMMUNE DISEASES USING SUCH DERIVATIVES

CROSS-REFERENCE TO RELATED APPLICATIONS

This application claims priority under 35 U.S.C. §371 from international application PCT/CA2008/000796, filed Apr. 25, 2008, which claims benefit of U.S. provisional application No. 60/924,111, filed Apr. 30, 2007.

FIELD OF INVENTION

The present invention relates to compounds of the following formula:

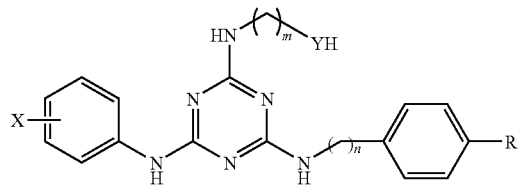

wherein X is fluorine or chlorine; Y is oxygen, sulfur, or an imino group; R is an amino, hydroxyl, sulfonamide, or carboxamide group or an N-monomethyl or N-dimethyl analog thereof; m is an integer from 2 to 6; and n is an integer from 0 to 2. The compounds may be used for treating certain cancers and autoimmune diseases.

BACKGROUND OF THE INVENTION

Cancer refers to more than one hundred clinically distinct forms of disease. Almost every tissue of the body can give rise to cancer and some can even yield several types of cancer. Cancer is characterized by an abnormal growth of cells that can invade the tissue of origin or spread to other sites. In fact, the seriousness of a particular cancer, or its degree of malignancy, is based upon the propensity of cancer cells to invade neighboring tissue and to spread. That is, various human cancers (e.g., carcinomas) differ appreciably as to their ability to spread from a primary site or tumor, and to metastasize throughout the body. Indeed, it is the process of tumor metastasis that is detrimental to long-term survival of the cancer patient. A surgeon can remove a primary tumor, but a cancer that has metastasized often reaches too many places to permit a surgical cure. To successfully metastasize, cancer cells must detach from their original location, invade into a blood or lymphatic vessel, travel in the circulation to a new site, and establish a tumor there.

The twelve major cancers are prostate, breast, lung, colorectal, bladder, non-Hodgkin's lymphoma, uterine, melanoma, kidney, leukemia, ovarian, and pancreatic cancers. Melanoma is a major cancer and a growing worldwide health problem by virtue of its ability to metastasize to most organs in the body which include lymph nodes, lungs, liver, brain, and bone. The clinical outcome for patients with metastasis to distant sites is significantly worse than that seen with regional lymph node metastases. The median survival time for patients with lung metastases is eleven months while that for patients with liver, brain, and bone metastases is four months. Four types of treatment have been used for distant melanoma metastases: surgery, radiation therapy, chemotherapy, and immunotherapy. Surgery is most often used to improve the quality of life of the patient, such as removing a metastasis that is obstructing the gastrointestinal tract. Radiation therapy has some degree of efficacy in local control of metastases, but is primarily limited to cutaneous and/or lymph node metastases. A number of chemotherapeutic agents have been evaluated for the treatment of metastatic melanoma. However, only two cytotoxic drugs are able to achieve a response rate of 10% or more. These drugs are decarbazine (DTIC) and nitrosoureas. Only DTIC is approved for the treatment of melanoma in most countries. Subsequently, the lack of clinically significant, beneficial, long-term effects of surgery, radiation therapy, and chemotherapy for the treatment of metastatic melanoma has led to the use of immunotherapy. Thus far, most attention has been given to the cytokines interleukin-2 and interferon-α. Clinical trials have yielded better results with interleukin-2 but, on average, only 15% of patients with metastatic melanoma exhibit a significant reduction in tumor burden in response to interleukin-2.

Similar to melanoma, other cancers become seriously life threatening once metastasis occurs. Pancreatic cancer yields a 3% chance of survival beyond one year after metastasis (e.g., first diagnosis) occurs. This increases only to 18% upon treatment with the cytotoxic drug gemcitabine and 24% upon treatment with gemcitabine, tarceva, and the EGFr kinase inhibitor. Prostate cancer can be successfully controlled by surgery or radiation as long as the cancer is confined to the prostate. But there is little effective treatment available once metastasis occurs, especially if androgen-deprivation therapy fails.

Other cancers may be more effectively treated with chemotherapeutic agents than melanoma, pancreatic, or prostate cancer. Chemotherapeutic agents, however, suffer two major limitations. First, the chemotherapeutic agents are not specific to cancer cells and particularly at high doses, they are toxic to normal rapidly dividing cells. Second, with time cancer cells develop resistance to chemotherapeutic agents thereby providing no further benefit to the patient. As noted for melanoma, other treatment modalities have been explored to address the limitations arising from the use of chemotherapeutic agents. Nonetheless, these additional treatments have been of limited success for the treatment of other cancers. Examples of additional cancer treatments and their limitations include surgery (inability to completely remove extensive metastasis), radiation (inability to selectively deliver radiation to cancer cells), and immunotherapy (the use of toxic cytokines with limited efficacy). For this reason, other newer therapeutic approaches are under exploration (e.g., antiangiogenesis agents, apoptosis agents, gene therapy) but these treatments are, relatively speaking, in their infancy. Therefore, a need still exists for novel approaches exemplified by novel chemotherapeutic agents which are efficacious (e.g., reduction in tumor size or spread of metastases), have limited toxicity for the treatment of cancer, prolong the time to develop drug resistance, or any combination thereof.

SUMMARY OF THE INVENTION

In one embodiment, compounds, compositions containing such compounds, and methods of manufacturing medicaments are provided.

In another embodiment, they may act through a useful mechanism of action with reduced toxicity for the treatment of at least some cancers. Although they may be used alone to treat cancer, a more efficacious treatment may comprise the use of the compounds in combination with other anticancer drugs or therapies. Use of the compounds in combination with chemotherapeutic agents may provide a potential method to address the limitations noted above that arise with the use of chemotherapy: drug toxicity and drug resistance. Thus, the compounds may be relatively less toxic than other chemotherapeutic agents, as evidenced by cell cytotoxicity and animal data, and their different mechanism of action should dampen chemotherapeutic drug resistance, especially if the dose of the chemotherapeutic agent can be lowered when used in combination with compounds of the present invention. The compounds may be used in the manufacture of a medicament for treating cancer.

In yet another embodiment, they may act through a useful mechanism of action with reduced toxicity for the treatment of at least some autoimmune diseases. Although they may be used alone to treat autoimmune disease, a more efficacious treatment may comprise the use of the compounds in combination with other anti-inflammatory drugs or therapies. The compounds may be used in the manufacture of a medicament for treating autoimmune disease.

Further aspects of the invention will be apparent to a person skilled in the art from the following description and claims and generalization therein.

DESCRIPTION OF CERTAIN EMBODIMENTS OF THE INVENTION

Figure 1A:
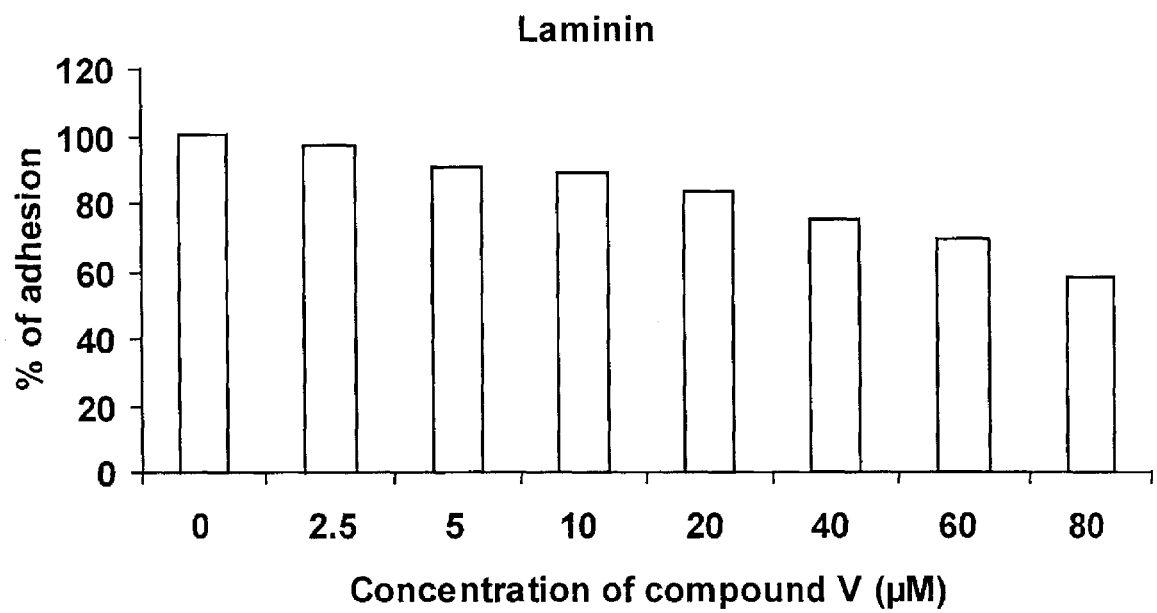
FIG. 1 shows the effect of compound V on PC-3 cell adhesion on a variety of substrates: (A) laminin, (B) MATRIGEL™ basement membrane matrix, or (C) collagen.

Compounds of the present invention, or pharmaceutically-acceptable derivatives thereof, are described by the following formula:

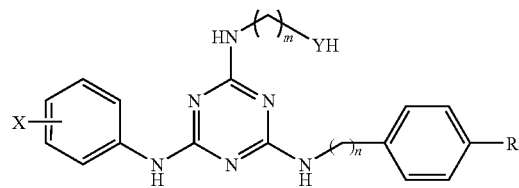

wherein
X is F or Cl;
Y is NH, O, or S;
R is $NH_2$, OH, $SO_2NH_2$, $SO_2N(CH_3)H$, $SO_2N(CH_3)_2$, or $CONH_2$;
m is 2, 3, 4, 5 or 6; and n is 0, 1 or 2 in which a two-carbon fragment (n=2) may be represented by
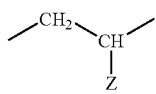
for Z=H or OH.
In preferred embodiments, one or more of the following may apply:
X=F; and/or
Y=NH or O; and/or
R=$NH_2$, OH, $SO_2NH_2$, or $SO_2N(CH_3)_2$; and/or
m=4, 5 or 6; and/or
n=2.
Particularly preferred are compounds I-XI which have the following structures:
| Compound | Structure |
|---|---|
| I | 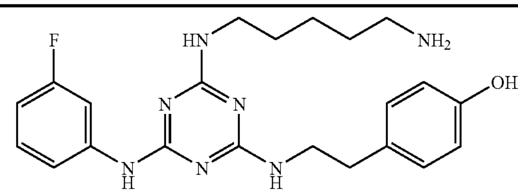 |
| II | 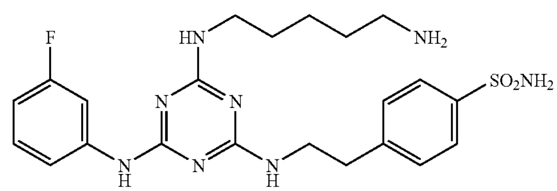 |
| III | 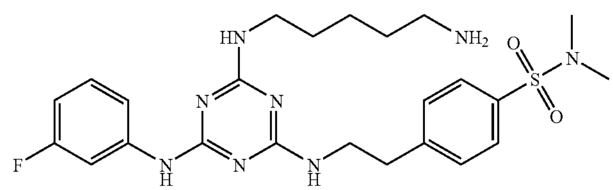 |
| IV | 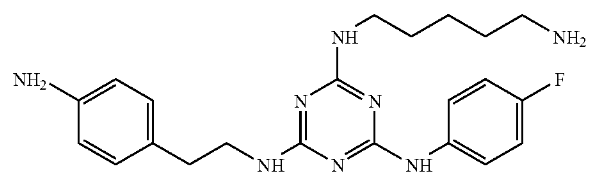 |
| V | 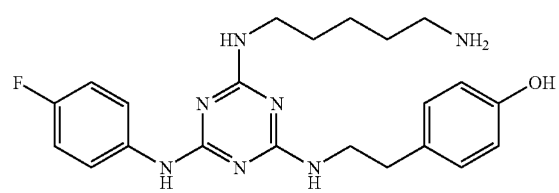 |
| VI | 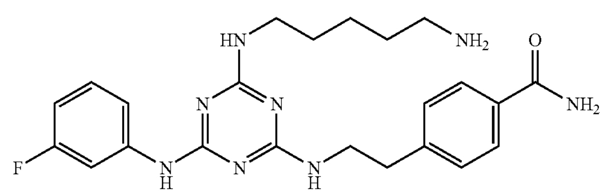 |
| VII | 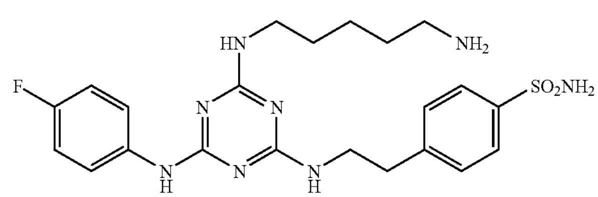 |

-continued

| Compound | Structure |
|---|---|
| VIII | 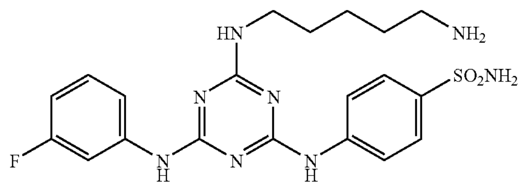 |
| IX | 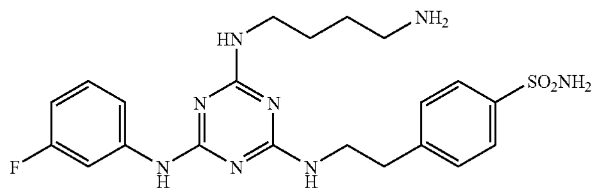 |
| X | 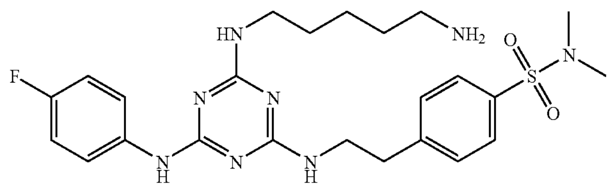 |
| XI | 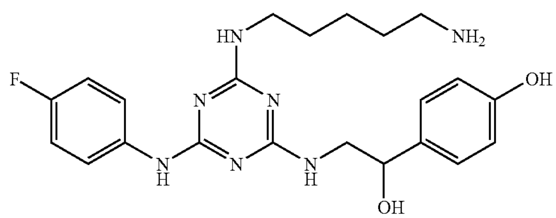 |
| XII | 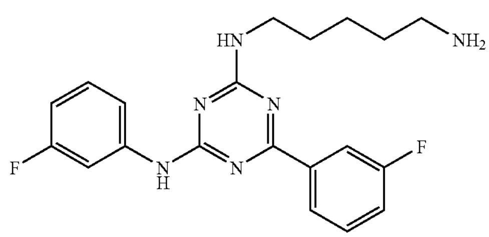 |

Although some compounds are described by the general formula above, it will be appreciated by anyone skilled in the art that certain structural modifications which lie outside of the formula, but which are nonetheless obvious, fall within the scope of this invention. For example, it is possible to synthesize compounds described by the above formula that do not contain a halogen substitution on the phenyl ring. Such compounds were made, but they were observed to be generally more toxic than monochloro- or fluorophenyl-substituted triazine compounds. Similarly, dihalophenyl substituted triazine compounds fall within the scope of the present invention. Additionally, although the general formula describes para-substituted (amino, hydroxyl, sulfonamide, etc.) phenethyl compounds, it is possible that such substituents can also be made at ortho- or meta-positions of the benzene ring portion of the phenethyl moiety. Finally, the ethylene portion of the substituted phenethyl moiety can be replaced by an unsaturated ethylene fragment or a fused cyclic (five or six-membered ring) structure with the benzene ring to introduce a structure with less degrees of freedom than the phenethyl moiety or a more rigidified alternative.

One novel approach to the treatment of cancer lies in the discovery of new compounds which are efficacious in reducing tumor size and/or the spread of metastasis and which can also reduce inflammation. Compounds of the present invention may satisfy this requirement for such a novel class of compounds useful for the treatment of cancer. That is, compounds which simultaneously exhibit significant anticancer and anti-inflammatory properties offer a potential two-pronged approach which targets both genetically unstable tumor cells (high mutation rate and subsequent resistance to chemotherapy) and genetically normal cells present in inflamed tissue.

This two-pronged approach to the treatment of cancer is made more compelling by the increasing awareness that a link exists between chronic inflammation and the subsequent development of cancer. This chronic inflammation is, in turn, often the result of persistent and nonlife threatening (at the time) viral or bacterial infection. Indeed, the etiology of numerous specific cancers can be directly linked to specific pathogens. For example, human papilloma virus, hepatitis B or C virus, and Epstein-Barr virus are risk factors for cervical cancer, hepatocellular carcinoma, and lymphoproliferative disorders respectively. *H. pylori* is one of the main contributors to gastric cancer. It was more recently discovered that periodontal (gum) disease, a chronic inflammatory condition associated with the presence of a higher number of bacteria in the mouth, is linked to a significantly higher risk of developing pancreatic cancer.

The link between cancer and inflammation appears to have its roots at the molecular level. Molecules associated with inflammation, or a proinflammatory immune response, are linked with the progression of cancer. For example, tumor necrosis factor (TNFα) may be regarded as the most important of the proinflammatory cytokines since it regulates the production of other proinflammatory cytokines (e.g., IL-1, IL-6, IL-8, and GM-CSF). Interestingly, high doses of TNFα administered to tumor-bearing animals display anticancer activity. This has not, however, translated to significant anticancer activity in humans as evidenced by a phase I clinical trial with recombinant TNFα. More importantly, TNFα is expressed in a range of human tumors and its presence is generally associated with poor prognosis. Indeed, it appears that relatively low concentrations of endogenous TNFα chronically produced in the tumor microenvironment enhances tumor development and spread. That is, the anticancer activity of TNFα is only observed at supraphysiologic concentrations of this cytokine. Another molecule, or set of protein molecules, recently hypothesized to provide a link between cancer and inflammation is the transcription factor NFκB. NFκB, a family of DNA binding proteins, may be the strongest transcriptional activator in mammalian cells. This transcription factor activates the biosynthesis of a number of proteins which include several proinflammatory cytokines (including TNFα) and chemokines. As noted above for TNFα, many cancers have elevated NFκB activity. Work with a number of mouse models has shed light as to the mechanism by which sustained activation of NFκB might link inflammation to tumor promotion and progression. This work was recently reviewed by Karin & Greten (*Nature Immunology*, 5:749-759, 2005). Examples of autoimmune diseases that may be treated include arthritis (e.g., rheumatoid or psoriatic arthritis), psoriasis, Crohn's disease, inflammatory bowel disease, ankylosing spondylitis, Sjögren's syndrome, Still's disease (macrophage activation syndrome), multiple sclerosis, uveitis, scleroderma, myositis, Reiter's syndrome, Wegener's syndrome, systemic lupus erythematosus (SLE), immune thrombocytopenic purpura (ITP), glomerulonephritis, and vasculitis.

One indication of the ability of the compounds of the present invention to address at least one of the molecular links described above between cancer and inflammation, TNFα, is demonstrated in Examples 21 and 22. In these examples, it is shown in cell based assays (WEHI-13VAR and J774A.1 cells) that compounds of the present invention may antagonize the proinflammatory activity of TNFα. That is, these compounds may inhibit the effect of TNFα as ascertained by their ability to inhibit TNFα-induced apoptosis or cytotoxicity in the WEHI-13VAR cell line and to inhibit LPS-induced production of TNFα in the J774A.1 cell line.

Another indication of the ability of the compounds of the present invention to address other molecular links described above between cancer and inflammation, arachidonic acid metabolites, is demonstrated in Example 28. In this example, it is shown in an LPS-induced, air-pouch model that compounds of the present invention induce an inhibition of prostaglandin $E_2$ ($PGE_2$) and leukotriene $B_4$ ($LTB_4$) production. Further to their pro-inflammatory properties, it is well documented that the eicosanoid pathway is activated in prostate, breast, and colon cancer. Cyclooxygenase (COX; prostaglandin) and lipoxygenase (LOX; leukotriene) metabolites contribute to the progression of the disease via the promotion of cell proliferation, motility, invasion, and angiogenesis. That is, these compounds may inhibit cancer and inflammatory diseases by their inhibitory effect on the production of $PGE_2$ and $LTB_4$ as ascertained by their ability to inhibit LPS-induced inflammation in an air-pouch model.

Compounds of the present invention include all pharmaceutically acceptable derivatives, such as salts and prodrug forms thereof, and analogues as well as any geometrical isomers or enantiomers. Formulations of the active compound may be prepared so as to provide a pharmaceutical composition in a form suitable for enteral, mucosal (e.g., sublingual, pulmonary, and rectal), parenteral (e.g., intramuscular, intraarterial, intradermal, subcutaneous, and intravenous), or topical (e.g., ointments, creams, and lotions) administration. In particular, compounds of the present invention may be solubilized in an alcohol or polyol solvent (e.g., SOLUTOL® HS 15 polyoxyethylene esters of 12-hydroxystearic acid from BASF, glycerol, ethanol, etc.), aqueous solution of mono- or disaccharides, or any other biocompatible solvent such as dimethyl sulfoxide (DMSO) or CREMOPHOR EL® polyethoxylated castor oil (also from BASF). The formulation may, where appropriate, be conveniently presented in discrete dosage units and may be prepared by any of the methods well known in the art of pharmaceutical formulation. All methods include the step of bringing together the active pharmaceutical ingredient with liquid carriers or finely divided solid carriers or both as the need dictates. When appropriate, the above-described formulations may be adapted so as to provide sustained release of the active pharmaceutical ingredient. Sustained release formulations well known to the art include the use of a bolus injection, continuous infusion, biocompatible polymers, or liposomes.

Suitable choices in amounts and timing of doses, formulation, and routes of administration can be made with the goals of achieving a favorable response in the mammal (i.e., efficacy), and avoiding undue toxicity or other harm thereto (i.e., safety). Therefore, "effective" refers to such choices that involve routine manipulation of conditions to achieve a desired effect: e.g., reducing morbidity or mortality of a patient with a cancer or autoimmune disease; decreasing cancer cell growth or metastasis; altering cell cycling or apoptosis; reducing or otherwise ameliorating tissue injury associated with an immune response to body constituents (organs and tissues like adrenal, eye, kidney, liver, lung, pancreas, nervous system, skin, synovial joint, thyroid, etc.); restoring the immunological status or normalizing a pathological disorder/condition of the mammal (antibody titer, immune cell subsets, signaling by cytokines or chemokines, antibody-antigen immune complexes, etc.); removing free antibodies and/or antibody-antigen immune complexes from the circulation; improving laboratory indicia of autoimmune disease (concentration or absolute amount of soluble mediators of inflammation, presence of autoantibodies, cellular proliferation, etc.); increasing efficacy of conventional chemotherapeutic or anti-inflammatory drug therapy; and combinations thereof. In particular, deleterious effects of conventional chemotherapeutic or anti-TNFα treatment may be avoided. The mammal may be an animal or a human patient.

The amount of compound administered is dependent upon factors such as, for example, bioactivity and bioavailability of the compound (e.g., half-life in the body, stability, and metabolism); chemical properties of the compound (e.g., molecular weight, hydrophobicity, and solubility); route and scheduling of administration; and the like. It will also be understood that the specific dose level to be achieved for any particular patient may depend on a variety of factors, including age, health, medical history, weight, combination with one or more other compounds, and severity of disease.

The terms "treatment" refers to, inter alia, reducing or alleviating one or more symptoms of cancer or autoimmune disease. For a given patient, improvement of a symptom, its worsening, regression or progression may be determined by an objective or subjective measure.

Finally, it will be appreciated by those skilled in the art that the reference herein to treatment extends to prophylaxis as well as therapy of an established cancer or autoimmune disease. Thus, for example, compounds of the present invention could be used after surgical removal of the primary tumor or prior to surgery or aggressive chemotherapy or even when the patient is in remission. The relative lack of toxicity of the compounds observed in the in vivo mouse studies (e.g., as observed in the attached examples) when compared to standard cancer therapies allows for greater prophylactic use than would be advisable with conventional therapies. Similarly, compounds of the present invention may be used in combination with other existing modes of treatment of cancer or autoimmune disease or agents used for the treatment of cancer (e.g., cytotoxic drugs, angiogenesis inhibitors, immunostimulants, protein kinase inhibitors) or autoimmune disease (e.g., anti-inflammatory corticosteroids, nonsteroidal anti-inflammatory drugs, methotrexate, DMARDs, biologics such as recombinant protein or monoclonal antibody). Examples of chemotherapeutic agents that may be used with one or more compounds of the invention include decarbazine, doxorubicin, daunorubicin, cyclophosphamide, vinblastine, vincristine, bleomycin, etoposide, topotecan, irinotecan, taxotere, taxol, 5-fluorouracil, gemcitabine, cisplatin, carboplatin, oxaliplatin, satraplatin, and chlorambucil.

Examples of therapeutic agents that may be used with one or more compounds of the invention include those that block binding of TNFα to its receptor or subsequent signal transduction (e.g., recombinant proteins which specifically bind to TNFα, anti-TNFα antibodies, soluble TNFα receptors, non-proteinaceous compounds which are less than 1000 MW). The dose of compound to be administered will ultimately be at the discretion of the oncologist, rheumatologist, or other physician. In general, however, the dose will be in the range from about 1 to about 75 mg/kg per day. More preferably, the range will be from about 2 to about 50 mg/kg per day.

The following examples further illustrate the practice of this invention but are not intended to be limiting thereof.

EXAMPLES

The general synthetic sequence for preparation of the compounds useful in the present invention is outlined in route 1 or route 2 (Scheme 1). Route 1 illustrates the reaction of cyanuric chloride with haloaniline to give the dichloro-triazine intermediate. Aryl or aralkylamines were then added followed by alkylamines. Route 2 demonstrates the preparation of the dichloro-triazine intermediate as in route 1 followed first by the reaction with alkylamines then by the addition of aryl or aralkylamines. The last step was the removal of the protecting groups.

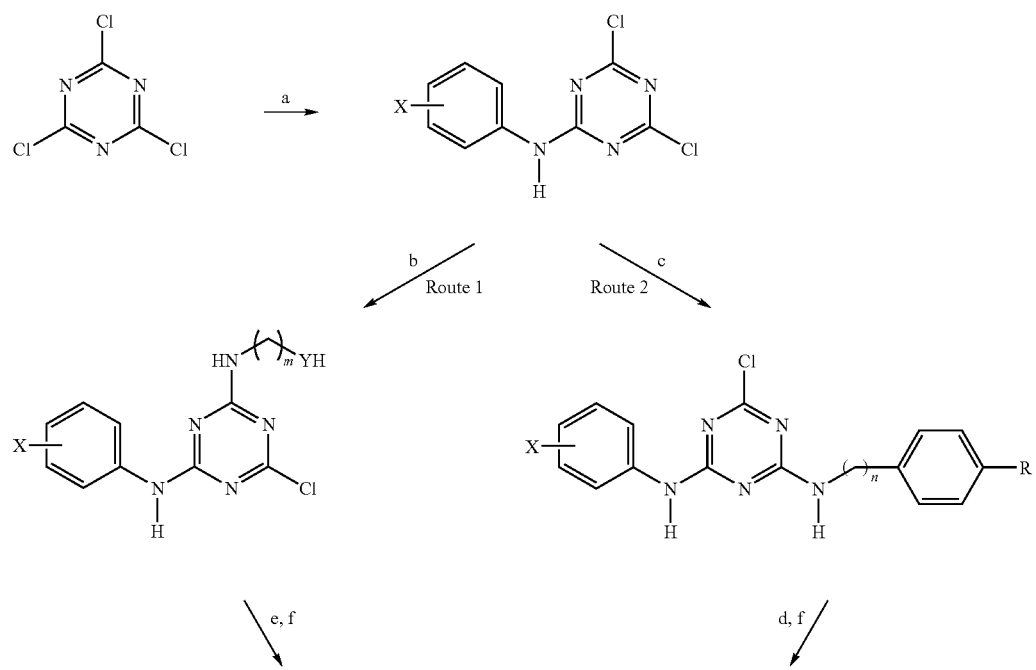

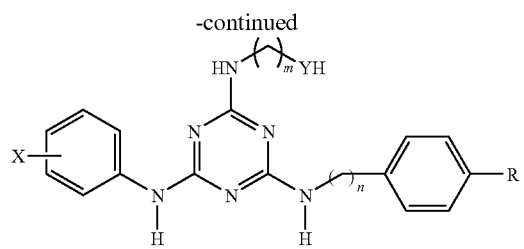

Reagents: (a) haloaniline, acetone/water, −10° C.→r.t.; (b) alkyldiamine or alkanolamine or thioalkylamine, NaHCO$_3$/H$_2$O/THF/acetone, r.t.; (c)

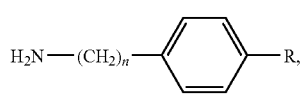

NaHCO$_3$, acetone/H$_2$O; (d) alkyldiamine or alkanolamine or thioalkylamine, THF/MeOH, 130° C./10 min, microwave; (e)

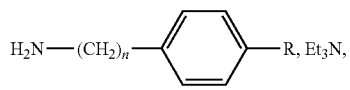

THF, 65° C.; (f) removal of the protecting group (where applicable).

Instrumentation

All HPLC chromatograms and mass spectra were recorded on a HP 1100 LC-MS Agilent instrument using a diode array detector. An analytical C18 column (75×4.6 mm, 5 microns) with a gradient of 1%-40% acetonitrile-water containing 0.01% TFA in 6 min and a flow of 2 ml/min (method 1), an analytical C18 column (75×4.6 mm, 5 microns) with a gradient of 15-99% acetonitrile-water containing 0.01% TFA in 6 min and a flow of 2 ml/min (method 2), an analytical C18 column (75×4.6 mm, 5 microns) with a gradient of 0.1%-20% acetonitrile-water containing 0.01% TFA in 5 min and a flow of 1 ml/min (method 3), or an analytical C18 column (75×4.6 mm, 5 microns) with a gradient of 1%-50% acetonitrile-water containing 0.01% TFA in 5 min and a flow of 1 ml/min (method 4) was used.

Example 1

Synthesis of Compound I (Representative Example of Route 1)

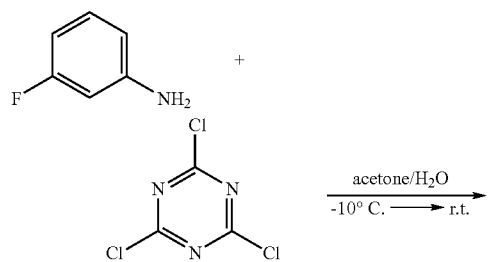

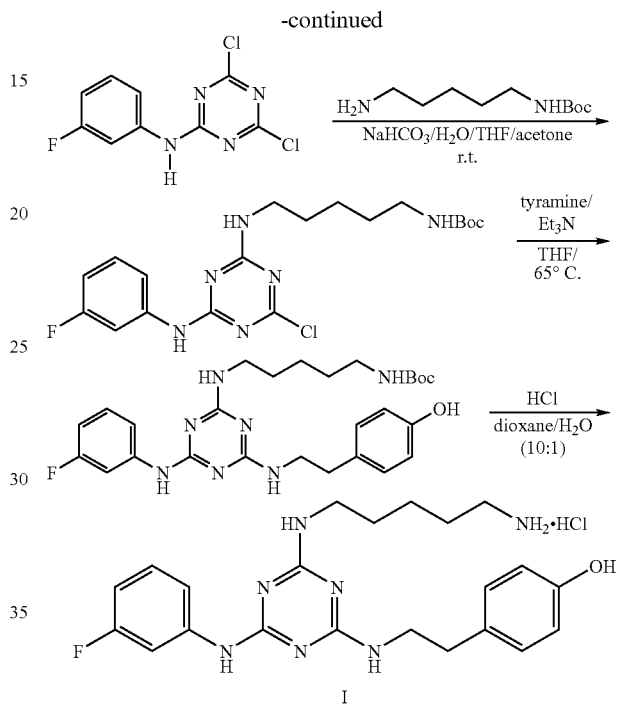

Cyanuric chloride (10.0 g, 54.2 mmol) was added in small portions to a cooled (−10° C.) mixture of water (50 ml) and acetone (50 ml). A solution of the 3-fluoroaniline (5.2 ml, 54.2 mmole) in acetone (50 ml) was added slowly over 50 min, maintaining the temperature of the reaction below −5° C. The reaction was then stirred at ambient temperature for one hour. The pH of the reaction was adjusted from 2 to 8 with saturated aqueous sodium bicarbonate (200 ml), and stirring was continued for a further 30 min. The precipitated solid was collected by filtration, washed with water and dried in vacuo. This gave 2,4-dichloro-3-fluorophenylamino-1,3,5-triazine as a white solid: 13.3 g, 94% yield; $^1$H NMR (400 MHz, d$_6$-DMSO): δ 6.97-7.01 (1H, m), 7.38-7.43 (2H, m), 7.52-7.55 (1H, m), 11.25 (1H, br); LRMS (ESI): m/z 259 (MH+); HPLC (method 2): 4.1 min. The product was used in the next step without further purification. This dichloro-triazine derivative (6.4 g, 24.7 mmole) was dissolved in THF (70 ml) at room temperature and was treated with a solution of the 5-(tert-butoxycarbonylamino)pentylamine (7.5 g, 37.0 mmole) in a mixture of acetone (50 ml) and water (50 ml). The resulting solution was then treated with a saturated aqueous sodium bicarbonate (70 ml). The reaction was stirred at room temperature for 2.5 hr to 3 hr. The mixture was then concentrated in vacuo, diluted with water, and extracted with ethyl acetate. Combined organic extracts were washed with saturated aqueous sodium chloride, 2M aqueous HCl, saturated sodium chloride, saturated sodium bicarbonate, and saturated sodium chloride then dried (magnesium sulfate-charcoal), filtered through CELITE diatomaceous earth, and concentrated in vacuo to 200 ml. This solution was poured, with stirring, into 1.2 L of hexane and the precipitate was collected by filtration, washed with hexane, and dried in vacuo to yield the monochloro-[1,3,5]triazine derivative as a white solid: 6.6 g, 63% yield; $^1$H NMR (400 MHz, $d_6$-DMSO) δ 1.23-1.30 (2H, m), 1.31-1.56 (2H, m), 1.34 (9H, s), 1.44-1.56 (2H, m), 2.85-2.91 (2H, m), 3.20-3.30 (2H, m), 6.70-6.77 (1H, m), 6.79-6.85 (1H, m), 7.25-7.33 (1H, m), 7.38-7.43 (1H, m), 7.67-7.75 & 7.76-7.85 (1H, br), 8.14-8.21 & 8.22-8.30 (1H, br), 10.05-10.11 & 10.15-10.26 (1H, br); LRMS (ESI): m/z 425 (MH+), 447 (MH+Na); HPLC (method 2): 4.5 min. A solution of the monochloro-triazine (6.6 g, 15.6 mmole) in THF (300 ml) was treated with tyramine (6.4 g, 46.7 mmole) and triethylamine (77.7 mmol, 10.9 ml). The reaction was heated at 65-70° C. for 16 hr to 60 hr, then cooled to ambient temperature and concentrated in vacuo. The residue was extracted with ethyl acetate and filtered. The filtrate was washed with 1M aqueous HCl, saturated sodium chloride, saturated aqueous sodium bicarbonate, and saturated sodium chloride, then dried (magnesium sulfate-charcoal), filtered through CELITE diatomaceous earth, and concentrated in vacuo. The residue was then dissolved in ether (150 ml) and this solution was added dropwise to 1.4 L of hexane with vigorous stirring. The precipitated solid was collected by filtration and dried in vacuo to yield the tri(amino-substituted)-[1,3,5]triazine derivative as an off-white solid: 6.5 g, 80% yield; $^1$H NMR (400 MHz, $d_6$-DMSO) δ 1.21-1.29 (2H, m), 1.32-1.41 (2H, m), 1.34 (9H, s), 1.44-1.54 (2H, m), 2.65-2.71 (2H, m), 2.88 (2H, dt, J=6.5, 6.5 Hz), 3.15-3.27 (2H, m), 3.33-3.42 (2H, m), 6.61-6.70 (1H, m), 6.67 (2H, d, J=8.5 Hz), 6.71-6.76 (1H, m), 6.84-7.02 (1H, m), 7.01 (2H, d, J=8.5 Hz), 7.16-7.23 (1H, m), 7.39-7.47 (1H, m), 7.87-7.91 (1H, m), 8.92-8.94 & 9.00-9.06 (1H, 2×br), 9.13 (1H, s); LRMS (ESI): m/z 526 (MH+), 548 (MH+Na); HPLC (method 2): 2.9 min. A solution of the Boc-protected compound (6.5 g, 12.4 mmole) in 4M HCl/1,4-dioxane (100 ml) and water (10 ml) was stirred at room temperature for 2 hr. Solvents and excess acid were evaporated in vacuo and traces of water were removed by co-evaporation (×2) with isopropanol (25 ml). The dried residue was dissolved in isopropanol (25 ml) and the solution was added dropwise to ether (450 ml) with vigorous stirring. The precipitated solid was collected by filtration, dried in vacuo, and then dissolved in pyrogen-free water (800 ml), filtered (0.22 μm), and lyophilized to give the deprotected compound I as an off-white solid: 5.5 g, 89% yield; $^1$H NMR (400 MHz, $d_6$-DMSO) δ 1.26-1.35 (2H, m), 1.47-1.57 (4H, m), 2.64-2.73 (4H, m), 3.24-3.31 (2H, m), 3.32-3.55 (5H, m, $CH_2+NH_3+$), 6.63 (2H, d, J=8.5 Hz), 6.82-6.89 (1H, m), 6.93-7.06 (2H, m), 7.24-7.39 (2H, m), 7.61-7.73 (1H, m), 7.81-7.93 (3H, m), 8.15-8.25, 8.40-8.60, 9.10-9.30, 10.25-10.40 & 10.55-10.65 (2H, br); $^{19}$F NMR (376.5 MHz, $CD_3OD$): δ −114.50 to −113.84 (1F, m); LRMS (ESI): m/z 426 (MH+), 448 (MH+Na); HPLC (method 2): 1.6 min.

Example 2

Synthesis of Compound V (Representative Example of Route 2)

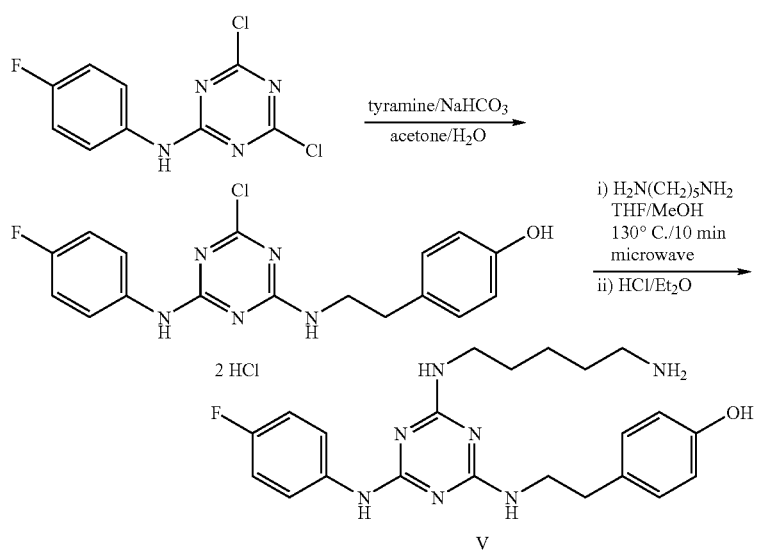

2,4-Dichloro-4-fluorophenylamino-1,3,5-triazine was prepared in accordance with Example 1 using 4-fluoroaniline (18 ml, 190 mmol) replacing 3-fluoroaniline to yield a white solid: 44.3 g, 90% yield; $^1$H NMR (400 MHz, $d_6$-DMSO) δ; LRMS (ESI): m/z 259 (MH+) HPLC (method 2): 4.0 min. The dichloro-triazine (44.2 g, 0.2 mole) was coupled with tyramine (35.1 g, 0.3 mole) according to Example 1 with tyramine replacing 5-(tert-butoxycarbonylamino)pentylamine to yield a white solid: 56.1 g, 91% yield; LRMS (ESI): m/z 360 (MH+), 382 (MH+Na); HPLC (method 2): 3.7 min. A solution of the monochlorotriazine (15.0 g, 41.8 mmole) and 1,5-diaminopentane (24.5 ml, 209 mmole) in tetrahydrofuran (125 ml) and methanol (60 ml) was divided into nine portions. Each portion was heated in a chemistry microwave apparatus at 130° C. for 10 min. The portions were then recombined, concentrated in vacuo, and the residue dissolved in ethyl acetate. The ethyl acetate solution was washed with water and with saturated sodium chloride, and then extracted with 2M aqueous HCl. The aqueous extract was washed with ethyl acetate, then basified with saturated aqueous sodium bicarbonate. The precipitate was extracted with ethyl acetate and the extracts were washed with saturated sodium chloride, then dried (magnesium sulfate-charcoal), filtered through CELITE diatomaceous earth, and concentrated in vacuo. The residue was dissolved in methanol (300 ml), and the solution was treated with a 1M solution of HCl in ether (60 ml) and the solution was concentrated in vacuo. The residue was dissolved in hot isopropanol (150 ml) and this solution was added dropwise to ether (1.5 L) with vigorous stirring. The precipitated solid was collected by filtration, dried in vacuo, and then dissolved in pyrogen-free water (1.6 L), filtered (0.22 μm) and lyophilized to give compound V as its hydrochloride salt: 14.9 g, 72% yield; mp 130-133° C.; $^1$H NMR (400 MHz, D$_2$O) δ 1.16-1.27 (2H, m), 1.37-1.54 (4H, m), 2.53-2.64 (2H, m), 2.76-2.83 (2H, m), 3.09-3.17 (2H, m), 3.21-3.48 (2H, m), 6.56-6.64 (2H, m), 6.85-7.02 (4H, m), 7.16-7.27 (2H, m); $^{19}$F NMR (376.5 MHz, CD$_3$OD): δ −118.1 to −116.0 (1F, m); LRMS (ESI): m/z 426 (MH+); HPLC (method 2): 1.6 min.

Example 3

Compound II

The above compound was prepared in accordance with Example 1 using 4-[2-aminoethyl]benzene-sulfonamide instead of tyramine. White solid, 77% yield; mp 145-147° C.; NMR (400 MHz, D$_2$O) δ 1.14-1.26 (2H, m), 1.33-1.44 (2H, m), 1.46-1.55 (2H, m), 2.64-2.84 (4H, m), 3.04-3.15 (2H, m), 3.33-3.56 (2H, m), 6.68-6.84 (1H, m), 6.88-6.99 (1H, m), 7.09-7.32 (4H, m), 7.44-7.63 (2H, m); $^{19}$F NMR (376.5 MHz, CD$_3$OD): δ −114.50 to −113.81 (1F, m); LRMS (ESI): m/z 489 (MO; HPLC (method 2): 1.6 min.

Example 4

Compound III

The above compound was prepared in accordance with Example 2 using N,N-dimethyl-4-[2-aminoethyl]benzene-sulfonamide instead of tyramine. N,N-dimethyl-4-(2-aminoethyl)benzene-sulfonamide, which was synthesized as follows: A solution of 4-[2-aminoethyl]benzene-sulfonamide (26.5 g, 0.1 mole) in anhydrous DMF (120 ml) was treated with phthalic anhydride (23.5 g, 0.2 mole), and the reaction was heated at 70° C. for 4 hr. The reaction was cooled to ambient temperature and 1,1'-carbonyldiimidazole (21.5 g, 0.1 mole) was added in small portions, and the reaction was stirred at ambient temperature overnight. Solvent was evaporated in vacuo, and the residue was washed with water, dried, and triturated with ethyl acetate to give the phthaloyl-protected compound as a white solid: 38.1 g, 89% yield; NMR (400 MHz, d$_6$-DMSO) δ 2.98 (2H, t, J=7.0 Hz), 3.82 (2H, t, J=7.0 Hz), 7.29 (2H, s), 7.38 (2H, d, J=8.0 Hz), 7.69 (2H, t, J=8.0 Hz), 7.76-7.84 (4H, m); LRMS (ESI): m/z 331 (MH$^+$), 348 (MH+Na); HPLC (method 2): 2.9 min. A solution of the phthaloyl-protected compound (12.7 g, 38.6 mmole) in anhydrous DMF (120 ml) under N$_2$ at 0° C. was treated with NaH (60% dispersion in oil; 3.5 g, 88.8 mmol) in small portions over 15 min and the reaction was stirred under N$_2$ at 0° C. for one hour. Iodomethane (4.8 ml, 77.2 mmole) was then added dropwise over 15 min and the reaction was stirred under N$_2$ at 0° C. to room temperature overnight. The resultant yellow suspension was poured onto ice/water (1.4 L), and was stirred for 30 min. The precipitate was collected by filtration, washed sequentially with water, hexane, and ether and then dried in vacuo to give the N,N-dimethyl-benzenesulfonamide derivative as a white solid: 11.3 g, 81% yield; LRMS (ESI): m/z 359 (MH$^+$), 381 (MH+Na); HPLC (method 2): 3.7 min. A solution of the phthaloyl-protected compound (11.3 g, 31.5 mmole) and hydrazine hydrate (4.6 ml, 44.6 mmoles) in 95% ethanol (125 ml) was heated at reflux for 2 hr. The white solid that formed was removed by filtration and washed with ethanol. Combined filtrate and washings were concentrated in vacuo, and the solid that formed was removed by filtration and washed with ethanol. This procedure was repeated thrice and the final filtrate was evaporated to dryness in vacuo. The solid was extracted with ethyl acetate. The extracts were concentrated in vacuo to give the free amine as a yellow oil: 4.8 g, 67% yield; $^1$H NMR (400 MHz, CD$_3$OD) δ 2.65 (6H, s), 2.84-2.92 (4H, m), 7.47 (2H, d, J=8.5 Hz), 7.71 (2H, d, J=8.5 Hz); LRMS (ESI): m/z 229 (MH$^+$), 251 (MH+Na); HPLC (method 2): 2.3 min. This compound was reacted with the dichlorotriazine followed by the alkyl amine, and then deprotected to give the final product. White solid (2.2 g, 92%); mp 143-146° C.; $^1$H NMR (400 MHz, CD$_3$OD) δ 1.42-1.53 (2H, m), 1.64-1.78 (4H, m), 2.60 & 2.64 (6H, 2×s), 2.92-2.99 (2H, m), 3.01-3.07 (2H, m), 3.39-3.48 (2H, m), 3.68-3.78 (2H, m), 6.83-6.92 (1H, m), 7.24-7.37 (2H, m), 7.42-7.71 (5H, m); LRMS (ESI): m/z 517 (MH$^+$), 539 (MH+Na); HPLC (method 1): 4.3 min.

Example 5

Compound IV

The above compound was prepared in accordance with Example 1 using 2-[4-aminophenyl]-ethylamine instead of tyramine. Yellow solid, 97% yield; mp 155-158° C.; $^1$H NMR (400 MHz, D$_2$O) δ 1.42-1.53 (2H, m), 1.63-1.76 (4H, m), 2.87-3.02 (4H, m), 3.40-3.48 (2H, m), 3.62-3.77 (2H, m), 7.07-7.15 (2H, m), 7.28-7.38 (3H, m), 7.40-7.49 (1H, m), 7.52-7.63 (2H, m); LRMS (ESI): m/z 425 (MH$^+$), 447 (MH+Na); HPLC (method 3): 1.9 min.

Example 6

Compound VI

The above compound was prepared in accordance with Example 2 using 4-[2-aminoethyl]benzamide and 3-fluoroaniline instead of tyramine and 4-fluoroaniline, respectively. 4-[2-Aminoethyl]-benzamide was prepared as follows: A suspension of 4-[2-aminoethyl]benzoic acid hydrochloride (5.0 g, 24.8 mmole) in methanol (200 ml) was treated with a 4M solution of HCl in 1,4-dioxane (10 ml, 40 mmole) and the reaction was heated at reflux overnight. Solvents and excess acid were removed in vacuo. The residue was triturated with ether and dried in vacuo to give the ester as a white solid: (5.5 g, quantitative); $^1$H NMR (400 MHz, CD$_3$OD) δ 3.04 (2H, t, J=7.0 Hz), 3.21 (2H, td, J=7.0, 0.5 Hz), 3.89 (3H, s), 7.41 (2H, dd, J=8.0, 0.5 Hz), 8.00 (2H, d, J=8.0 Hz). A suspension of this hydrochloride salt (5.4 g, 24.8 mmole) in tetrahydrofuran (60 ml) and methanol (30 ml) was treated with diisopropylethylamine (4.8 ml, 27.3 mmole) and di-tert-butyl dicarbonate (8.1 g, 37.2 mmole). The reaction was stirred at ambient temperature under N$_2$ for 5 hr. Solvents were evaporated in vacuo and the residue was dissolved in ethyl acetate. The solution was washed with water and saturated sodium chloride, then dried (magnesium sulfate), filtered, and evaporated in vacuo. The residue was triturated with cold ether and dried in vacuo to give the protected compound as a white solid (5.6 g, 81%); LRMS (ESI): m/z 192 (MH$^+$), 302 (MH+Na); HPLC (method 2): 3.9 min. A solution of the ester (5.6 g, 20.0 mmole) in 1,4-dioxane (36 ml) was treated with saturated aqueous ammonia (36 ml). The reaction was heated in a sealed tube at 100° C. overnight. After cooling, the precipitated solid was collected by filtration, washed with water, and dried in vacuo to give the amide as a white solid (4.4 g, 82%); LRMS (ESI): m/z 287 (MH+Na); HPLC (method 2): 2.6 min. Deprotection of the tert-butoxycarbonyl compound (4.4 g, 16.5 mmole) was undertaken by a modification of the procedure in Example 2 in which the water co-solvent was omitted and the solid was dried in vacuo rather than lyophilized, to yield a white solid (3.3 g, quantitative); LRMS (ESI): m/z 165 (MH$^+$), 187 (MH+Na); HPLC (method 2): 0.3 min. This compound was reacted with the dichloro-triazine, followed by the alkyl amine, and then deprotected to give the final product. White solid, 1.0 g, 20% yield; mp 190-192° C.; $^1$H NMR (400 MHz, D$_2$O) δ 1.13-1.26 (2H, m), 1.31-1.55 (4H, m), 2.54-2.84 (4H, m), 2.99-3.12 (2H, m), 3.23-3.49 (2H, m), 6.66-6.82 (1H, m), 6.86-7.14 (3H, m), 7.16-7.25 (2H, m), 7.36-7.57 (2H, m); LRMS (ESI): m/z 453 (MH$^+$); HPLC (method 2): 1.5 min.

Example 7

Compound VII

The Boc-protected compound (4.8 mmole) was deprotected by a variation of the procedure used in Example 1. In this case, 4M HCl/1,4-dioxane (36 ml) in methylene chloride (30 ml) was used, at 0° C. to ambient temperature, to yield a low-density, white solid, 87% yield; mp 165-168° C.; $^1$H NMR (400 MHz, CD$_3$OD) δ 1.40-1.51 (2H, m), 1.62-1.74 (4H, m), 2.87-3.04 (4H, m), 2.93 (2H, t, J 7.5 Hz), 3.01 (2H, t, J 6.5 Hz), 3.41 (2H, t, J 7.5 Hz), 3.64-3.77 (2H, m), 7.07-7.16 (2H, m), 7.29-7.48 (2H, m), 7.50-7.62 (2H, m), 7.77-7.86 (2H, m); $^{19}$F NMR (376.5 MHz, CD$_3$OD): δ −120.2 to −119.8 (1F, m); LRMS (ESI): m/z 245 (MH$^+$), 489 (MH+Na); HPLC (method 1): 3.6 min.

Example 8

Compound VIII

The above compound was prepared in accordance with Example 2 using 4-aminobenzene sulfonamide and 3-fluoroaniline instead of tyramine and 4-fluoroaniline, respectively. Pale-beige solid, 95% yield; mp 162-163° C.; $^1$H NMR (400 MHz, CD$_3$OD) δ 1.47-1.56 (2H, m), 1.67-1.78 (4H, m), 2.95 (2H, t, J=7.5 Hz), 3.52 (2H, t, J=7.0 Hz), 6.92-7.00 (1H, m), 7.29-7.42 (2H, m), 7.60-7.78 (1H, m), 7.82-7.95 (4H, m); $^{19}$F NMR (376.5 MHz, CD$_3$OD): δ −114.17 to −113.71 (1F, m); LRMS (ESI): m/z 461 (MH$^+$), 483 (MH+Na); HPLC (method 4): 3.7 min.

Example 9

Compound IX

The above compound was prepared in accordance with Example 2 using 4-[2-aminoethyl]benzene sulfonamide and 4-aminobutylamine instead of tyramine and 5-aminopentylamine, respectively. White solid, 74% yield; mp 181-184° C.; $^1$H NMR (400 MHz, CD$_3$OD) δ 1.65-1.77 (4H, m), 2.93-3.04 (4H, m), 3.42-3.54 (2H, m), 3.68-3.78 (2H, m), 6.86-6.95 (1H, m), 7.24-7.50 (4H, m), 7.57-7.66 (1H, m), 7.78-7.86 (2H, m); $^{19}$F NMR (376.5 MHz, CD$_3$OD): δ −116.10 to −115.43 (1F, m); LRMS (ESI): m/z 475 (MH$^+$), 497 (MH+Na); HPLC (method 1): 3.6 min.

Example 10

Compound X

The above compound was prepared in accordance with Example 2 using N,N-dimethyl-4-(2-aminoethyl)benzenesulfonamide instead of tyramine. Pale beige solid, 57% yield; mp 290-295° C. (decomp.); $^1$H NMR (400 MHz, D$_2$O) δ 1.12-1.27 (2H, m), 1.32-1.57 (4H, m), 2.30-2.44 (6H, m), 2.75-2.84 (4H, m), 3.06-3.19 (2H, m), 3.53-3.65 (2H, m), 6.98-7.04 (2H, m), 7.17-7.35 (3H, m), 7.37-7.48 (2H, m), 7.52-7.58 (1H, m); LRMS (ESI): m/z 517 (MH$^+$), 539 (MH+Na); HPLC (method 2): 1.8 min.

Example 11

Compound XI

The above compound was prepared in accordance with Example 2 using [±]-octopamine instead of tyramine. White solid, 36% yield; mp 122-125° C.; $^1$H NMR (400 MHz, CD$_3$OD) δ 1.36-1.43 (2H, m), 1.50 (2H, tt, J=7.0, 7.0 Hz), 1.57-1.63 (2H, m), 2.62 (2H, t, J=7.0 Hz), 3.28-3.40 (2H, m), 3.45 (1H, J=13.5, 8.0 Hz), 3.54-3.63 (1H, m), 4.67-4.75 (1H, m), 6.69 (2H, d, J=8.5 Hz), 6.96-7.00 (2H, m), 7.13 (2H, d, J=8.5 Hz), 7.56-7.67 (2H, m); LRMS (ESI): m/z 442 (MH$^+$); HPLC (method 1): 3.3 min.

Anticancer Activity

Example 12

In Vitro Cytotoxicity of Compounds Assayed on Normal and Cancer Cells

This assay was performed to determine the effect of compounds of the present invention on cell cytotoxicity. Cells were incubated in presence or absence of compounds in their respective conditioned media. After 24 hr or 72 hr incubation, 50 µl of 3-(4,5-dimethyl-2-thiazyl)-2,5-diphenyl-2H-tetrazolium bromide (MTT; 2 mg/ml) was added and further incubated for 4 hr. The supernatant was discarded and 100 µl of dimethylsulfoxide (DMSO) was added. Absorbance was read at 570 nm with a TecanSunrise ELISA plate reader. The control group consisted of cells without compounds and is referred to as 100% of viable cells. IC$_{50}$ was determined using Prism software.

Table 1 represents the effect (IC$_{50}$) of compounds on normal (NHDF or normal human dermal fibroblast; HUVEC or human umbilical vein endothelial cell) and cancer (PC-3 human prostate carcinoma cell; P815 murine mastocytoma cell) cell lines in a 24 hr or 72 hr cell culture. All compounds have weak effect on cell cytotoxicity. The predictive utility of cell based cytotoxicity assays to assess the potential in vivo anticancer activity of compounds with selected cancer cell lines is well established in the art and the use of whole cells, instead of isolated protein receptors or enzymes, provides a more reliable determination of activity. See, for example, Paull et al. (*J. Nat'l Cancer Inst.* 81:1088-1092, 1989); Monks et al. (*J. Nat'l Cancer Inst.* 83:757-766, 1991); Bandes et al. (*J. Nat'l Cancer Inst.* 86:770-775, 1994); and Kamate et al. (*Int'l J. Cancer* 100:571-579, 2002).

TABLE 1

Effect of compounds on normal and cancer cell cytotoxicity in 24-hour or 72-hour cell culture.

|  | $IC_{50}$ of 24-hour culture | | | | $IC_{50}$ of 72-hour culture | | | |
| --- | --- | --- | --- | --- | --- | --- | --- | --- |
| Compound | NHDF | HUVEC | PC-3 | P815 | NHDF | HUVEC | PC-3 | P815 |
| I | 56.8 | 18.8 | 49.4 | 34 | 16.3 | 10.1 | 11.8 | 4.0 |
| II | >100 | 92.2 | 32.2 | 66.5 | 28.6 | 38.9 | 18.5 | 1.6 |
| III | nd | nd | 30.1 | 13.6 | nd | nd | 27.6 | 5.5 |
| IV | 82.1 | 51.3 | 56.6 | 33 | 42.5 | >100 | 51.9 | nd |
| V | 78.6 | 31.8 | 43.3 | 23.5 | 45.8 | >100 | 26.8 | 7.5 |
| VII | nd | nd | 17.7 | 12.6 | nd | nd | 14.1 | 4.0 |
| VIII | nd | nd | 31.0 | 10.9 | nd | nd | 5.2 | 2.9 |
| XII | nd | nd | nd | nd | nd | nd | 9.0 | 21.7 | nd = not determined

Example 13

In Vitro Effect of Compounds on PC-3 Cell Migration or Invasion

An in vitro migration assay was used to assess cell mobility in two dimensions. PC-3 cells were plated on a 12-well plate and grown to confluence in RPMI+10% FBS. A rubber policeman was used to create a denuded area. Confluent cells were quiesced by mitomycin C treatment (0.5 µM) at the concentration used to prevent the confounding issue of cell proliferation and protein synthesis. These cells were also incubated in the presence or absence of endothelial growth factor (EGF) and compound for 24 hr, then they were photographed.

The effects of EGF and compound V on PC-3 cell migration or invasion in the in vitro migration assay were determined. EGF promotes the migration or invasion of PC-3 cells treated with mitomycin compared to control (i.e., no added EGF). The addition of different concentrations (i.e., 1 µM to 10 µM) of compound V to the cell culture medium produces an inhibition of the EGF-induced PC-3 migration or invasion. Similar results were observed with compound I. The addition of different concentrations (i.e., 1 µM to 20 µM) of compound I to the cell culture produces an inhibition of the EGF-induced PC-3 migration or invasion after 24 hr of culture.

Example 14

In Vitro Effect of Compounds on PC-3 Cell Adhesion to Extracellular Matrix Components An in vitro cell adhesion assay was used to assess the effect of the compounds on cancer cell adhesion. Microtiter 96-well plates were coated for 1 hr at room temperature with 50 µl/ml of adhesive ligands previously diluted to 5 µg/ml for laminin, 10 µg/ml for MATRIGEL™ basement membrane matrix, or 10 µg/ml for collagen in PBS. The wells were blocked with a solution of 1% BSA in PBS (100 µl/well) for 1 hr at 37° C. Subconfluent cultures of PC-3 cells were incubated with a 5 µM solution of calcein-AM for 30 min at 37° C., and then free calcein-AM was washed out (30 min) by incubation of the PC-3 cells in media without calcein-AM. Calcein-AM-labeled cells were trypsinized, washed, and resuspended in adhesion buffer (RPMI-1640, 10% FBS supplemented with 1 mM of $MgCl_2$). Labeled PC-3 cells were preincubated in absence or presence of compounds for 30 min and then a final volume of 100 µl of preincubated cells were allowed to attach at 37° C. in a humidified incubator for 15 min, 30 min, or 60 min at 37° C. Nonattached cells were removed by two washes with PBS and attached cells were lysed with 100 µl of a 1% Triton X-100 solution in PBS. Plates were read on a Tecan GENios Plus fluorescent reader with an excitation wavelength of 485 nm and an emission wavelength of 530 nm. The number of attached cells was calculated based upon standard curves. Nonspecific cell attachment (attachment to wells coated with BSA) was always less than 5%.

Figure 1B:
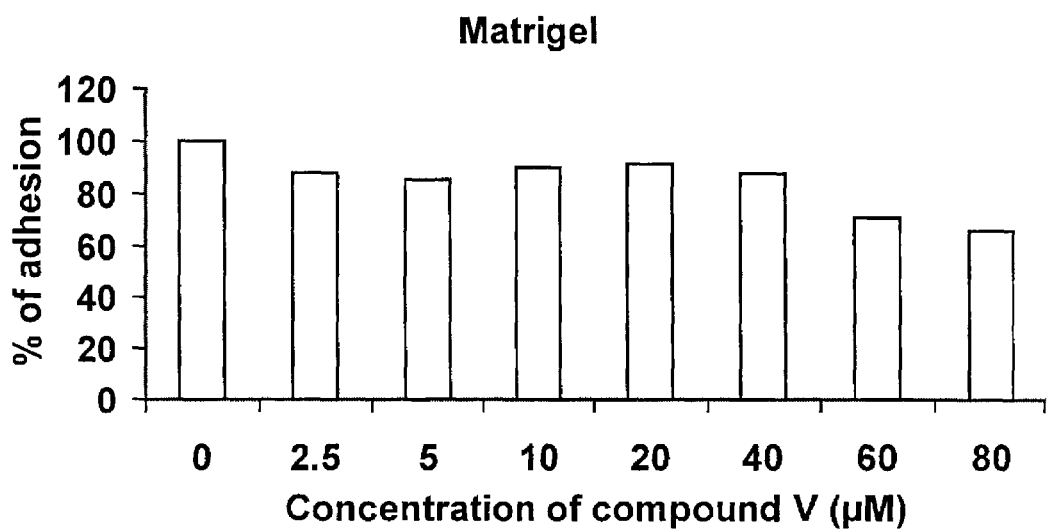
Figure 1C:
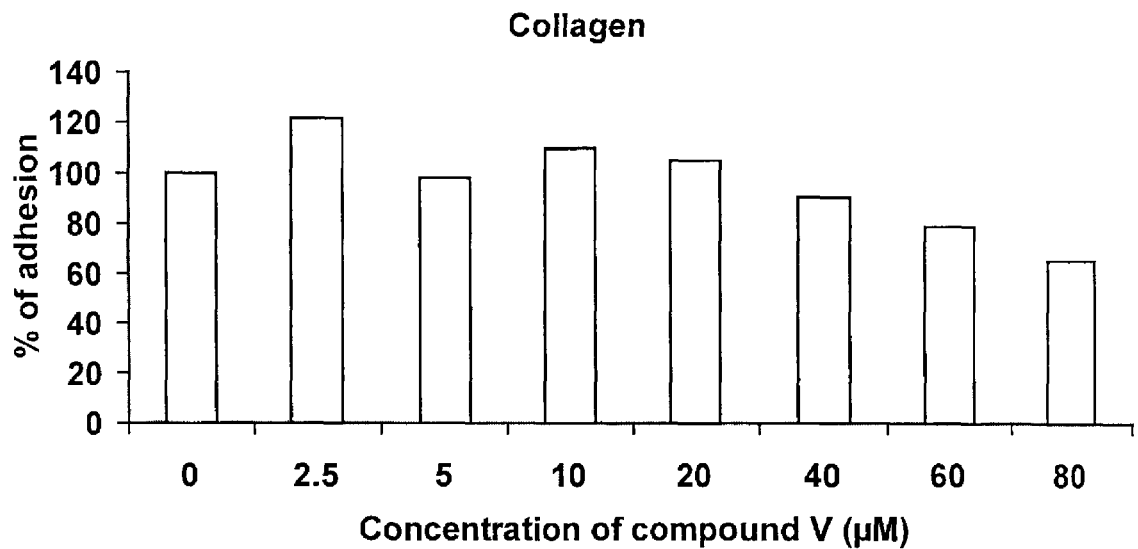

The addition of different concentrations of compound V in the above described in vitro cell adhesion assay inhibits PC-3 cells adhesion in a dose dependent fashion to a variety of substrates: laminin (FIG. 1A), MATRIGEL™ basement membrane matrix (FIG. 1B), or collagen (FIG. 1C).

Example 15

Antitumor Effects of Compounds on a Primary B16F10 Melanoma Tumor

Female 6-8 week old C57BL/6 mice were injected intradermally on day 0 with 50 µl of $3.75 \times 10^4$ viable B16F10 melanoma cells from ATCC (source of cell culture, Dr. I. J. Fidler). On day 14, tumors reached 80 mm and animals were randomized for treatments. Animals were then injected IV with saline (negative control) or compound (5 mg/kg, 25 mg/kg, or 50 mg/kg) on day 14, day 16, and day 18 or 10 mg/kg doxorubicin (positive control) on day 14. Mice were sacrificed on day 29. Body weight and tumor volume were recorded. Serial tumor volume was obtained by bi-dimensional diameter measurements with calipers, using the formula 0.4 ($a \times b^2$) where "a" was the major tumor diameter and "b" the minor perpendicular diameter. An antitumor effect can be quantitated by T/C, which is calculated as (Treated tumor volume/Control tumor volume)×100%.

Figure 2A:
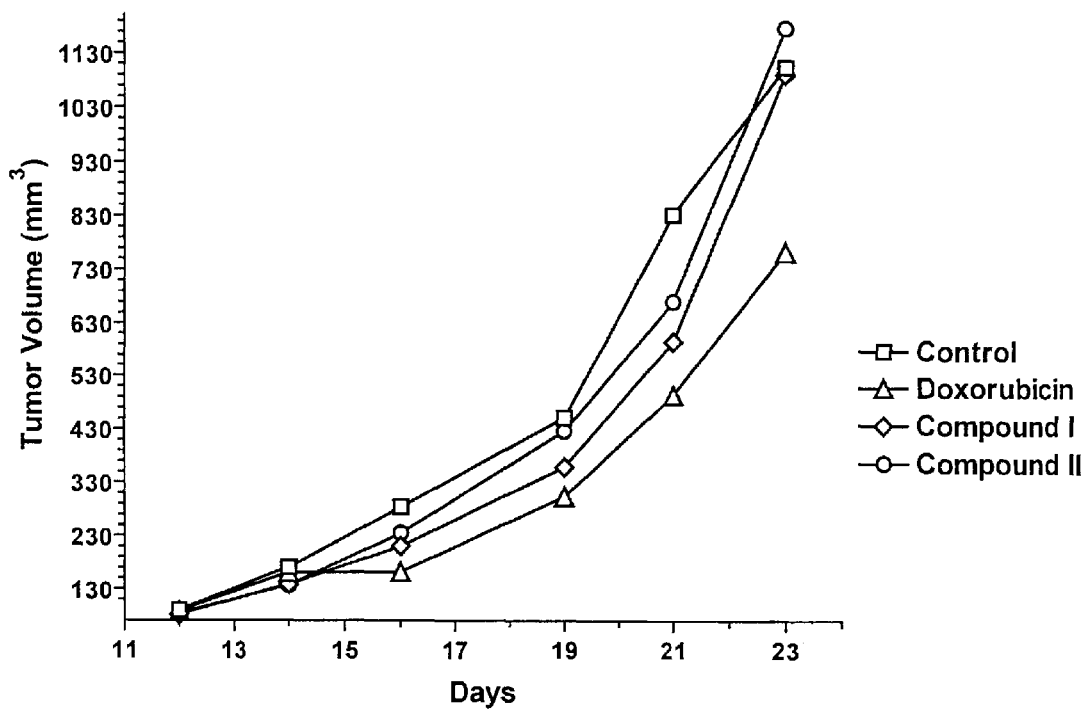
FIG. 2 shows the antitumor effects on a B16F10 primary melanoma of different compounds. The effects of compound I, compound II, or doxorubicin are compared in FIG. 2A. The effects of compound V or cytoxan are compared in FIG. 2B.
Figure 2B:
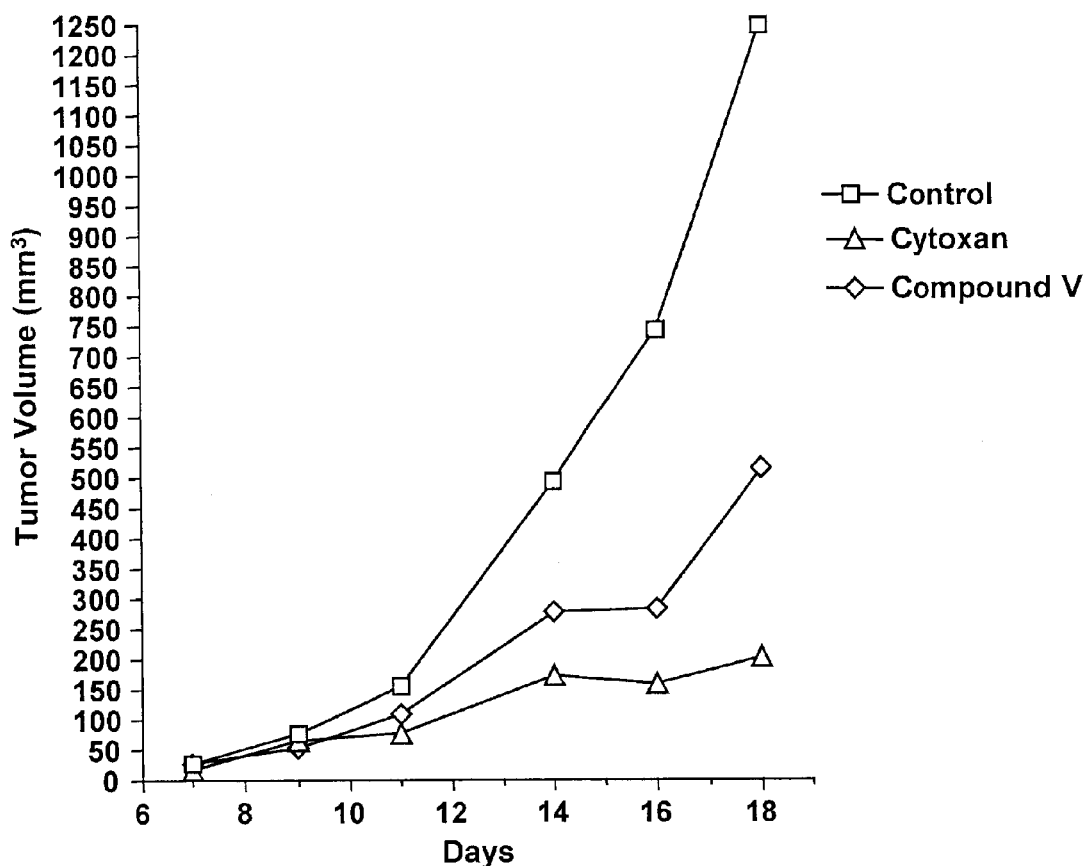

FIG. 2A shows the antitumor efficacy of compounds I or II on primary tumor B16F10 cells. Both compounds induce a weak reduction (T/C around 80%) of the tumor volume compared to the control. FIG. 2B shows the antitumor efficacy of compound V on primary tumor B16F10 cells. Compound V induces a significant reduction (T/C<40%, p=0.001) of the tumor volume compared to the control.

Example 16

Antitumor Effects of Compounds on a Primary DA-3 Breast Tumor

The syngeneic DMBA3 (DA-3, breast carcinoma model) cell line arose from a preneoplastic lesion treated with 7,12-dimethylbenzanthracene in female BALB/c mice. DA-3 cells were grown as monolayer cultures in plastic flasks in RPMI- 1640 containing 0.1 mM nonessential amino acids, 0.1 μM sodium pyruvate, 2 mM L-glutamine. This was further supplemented with 50 μM 2-mercaptoethanol and 10% fetal bovine serum. The DA-3 tumors were serially passaged in vivo by intradermal inoculation of 50 μl of $5\times10^5$ viable tumor cells to produce localized tumors in 6- to 8-week old BALB/c mice. The animals were then serially monitored by manual palpation for evidence of tumor. Mice were treated at day 11, 18, and 25 with cyclophosphamide (100 mg/kg, IV injection) and by intravenous treatment at day 11, day 12, day 13, day 15, day 18, day 20, day 22, and day 25 with compound. Mice were sacrificed from day 27 to day 55. Serial tumor volume was obtained by bi-dimensional diameter measurements with calipers, using the formula 0.4 $(a\times b^2)$ where "a" was the major tumor diameter and "b" the minor perpendicular diameter. Tumors were palpable, in general, 7 days to 10 days post-inoculation. The National Cancer Institute (USA) defines the product as effective if T/C is ≦40%.

Figure 3:
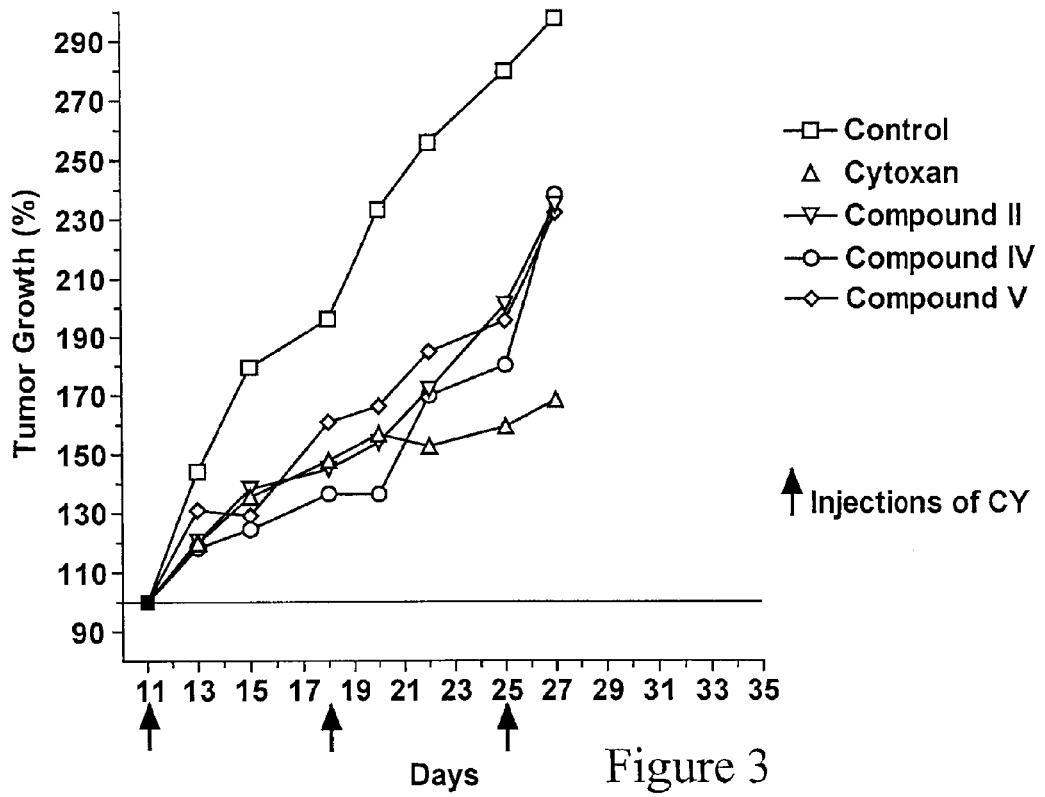
FIG. 3 shows the antitumor effects of intravenous administration of compound II, compound IV, compound V, or cyclophosphamide on a DA-3 breast tumor.

FIG. 3 shows the antitumor efficacy of intravenous administration (5 mg/kg) of compound II, compound IV, compound V, or cyclophosphamide. All compounds induce a significant ($p<0.05$) inhibition of tumor volume with a T/C between 25% to 70%. Furthermore, in comparison to cyclophosphamide which induces significant ($p<0.04$) inhibition of tumor volume with a T/C between 24% to 50%, all compounds were similar to cyclophosphamide up to day 20. The antitumor efficacy of combinations of compound and CYTOXAN cyclophosphamide was also determined against the DA-3 tumor.

Figure 4A:
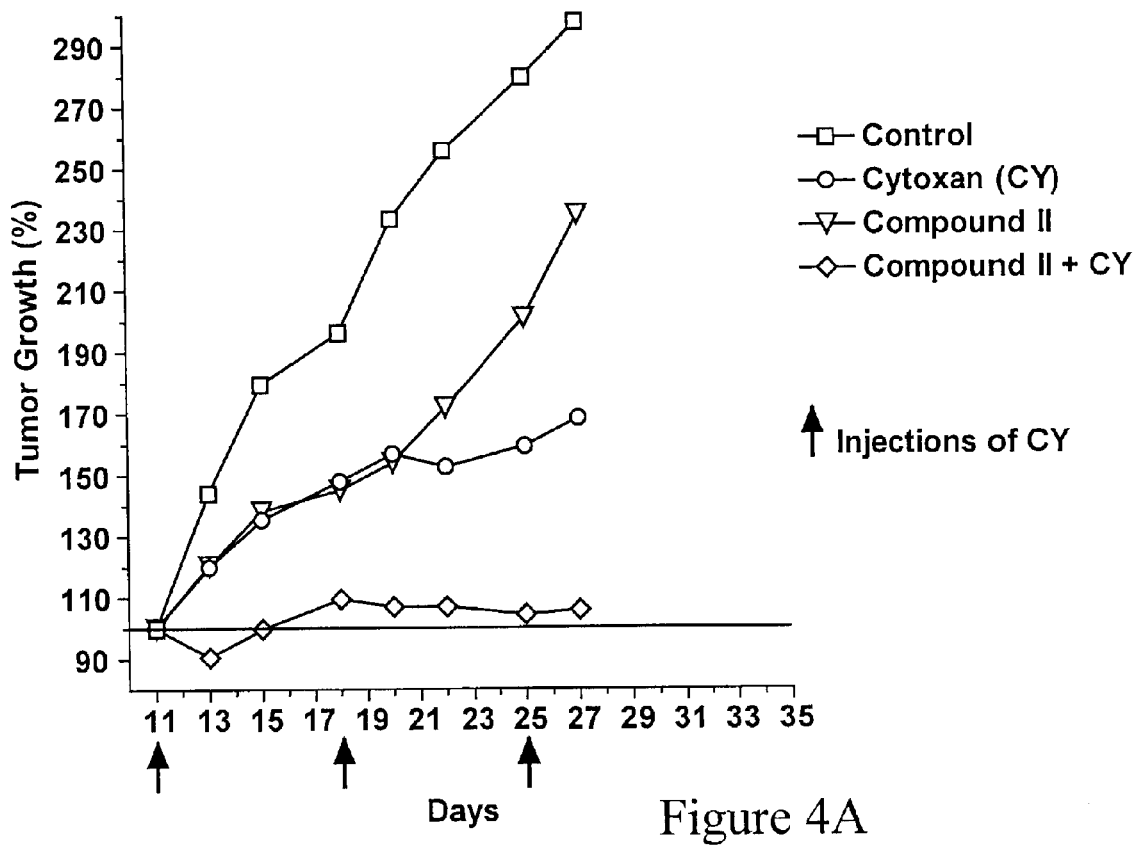
FIG. 4 shows the antitumor effects of intravenous administration of combinations of compounds on a DA-3 breast tumor. The effects of compound II, cyclophosphamide, and cyclophosphamide+compound II are compared in FIG. 4A. The effects of compound I, cyclophosphamide, and cyclophosphamide+compound I are compared in FIG. 4B. The effects of compound V, cyclophosphamide, and cyclophosphamide+compound V are compared in FIG. 4C.

FIG. 4A compares the antitumor efficacy of intravenous administration (50 mg/kg) of compound II alone to the combination of compound II and cyclophosphamide. Compound II induces significant ($p<0.05$) inhibition of tumor volume with a T/C between 40% to 70%. Furthermore, as compared to cyclophosphamide which induces significant ($p<0.05$) inhibition of tumor volume with a T/C between 24% to 50%, mice treated with the combination of cyclophosphamide and compound II also demonstrate a significant ($p<0.0001$) inhibition of tumor volume with a regression and a T/C lower than 10%. A regression and cytostatic effect (no growth) was observed in the combination regimen.

Figure 4B:
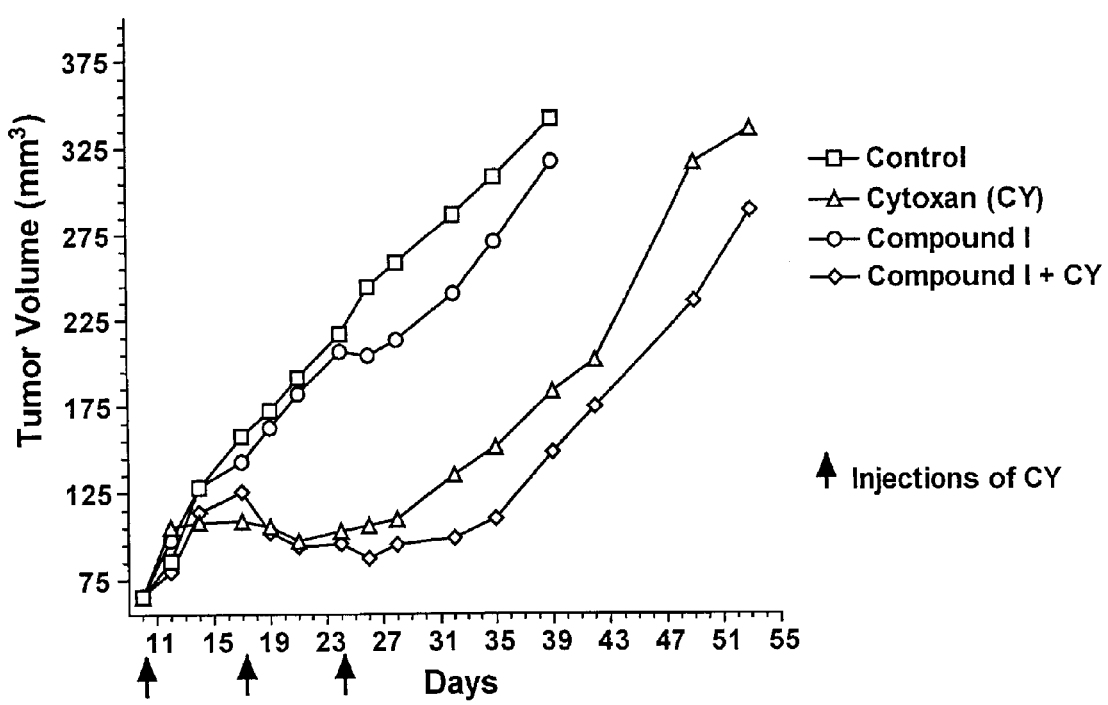

FIG. 4B compares the antitumor efficacy of intravenous administration (50 mg/kg) of compound I alone to the combination of compound I and cyclophosphamide. Compound I has a weak inhibitory effect on DA-3 tumor growth. Cyclophosphamide induces a significant ($p<0.01$) inhibition of tumor volume with a T/C between 20% to 50%, mice treated with the combination of cyclophosphamide and compound I also demonstrate a significant ($p<0.05$) inhibition of tumor volume with a T/C between 10% to 40%. A cytostatic effect (no growth) was observed in the combination regimen up to day 35. All treatments were stop at day 35. Cyclophosphamide-treated and combination CY+ compound I-treated mice were kept to observe the re-growth of the tumor. The re-growth of the tumor was similar in both groups, but less pronounced or delayed in the combination regimen group.

Figure 4C:
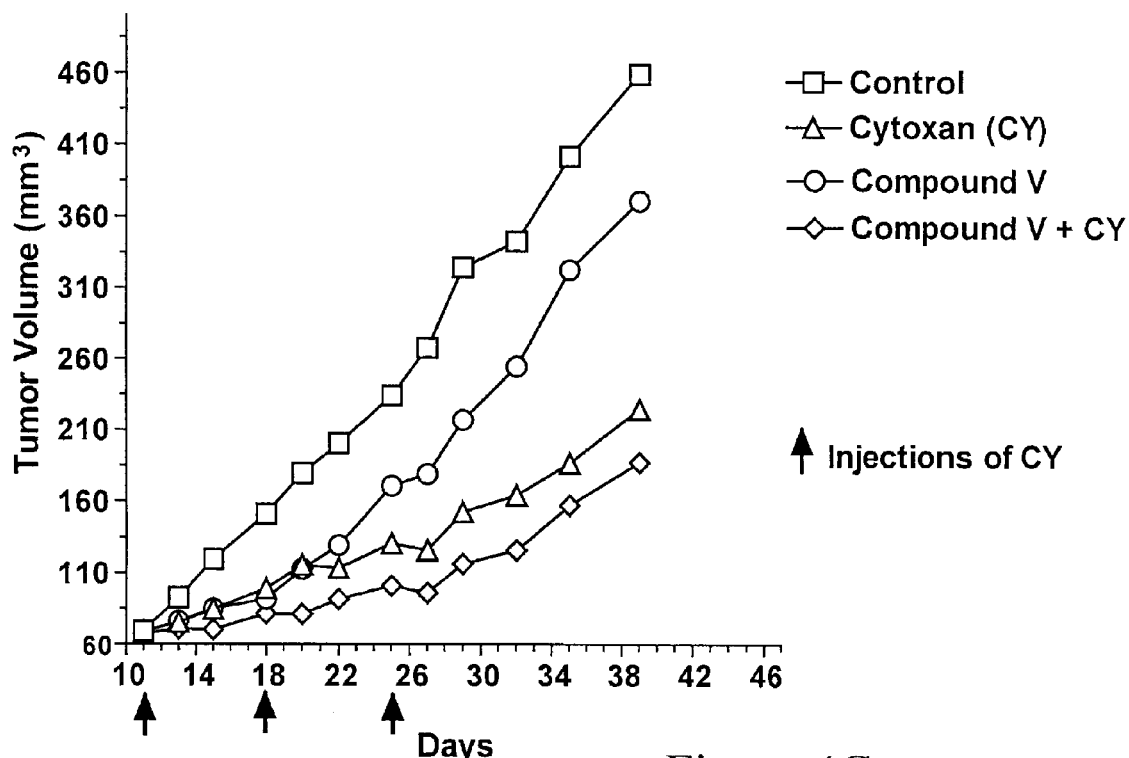

FIG. 4C compares the antitumor efficacy of intravenous administration (12.5 mg/kg) of compound V alone to the combination of compound V and cyclophosphamide. All regimens induce significant inhibition ($p<0.04$) of the tumor volume up to day 20. Mice treated with compound V demonstrated reduction of tumor volume with a T/C between 36% to 74%. However, in comparison to cyclophosphamide which induces an inhibition of tumor volume with a T/C between 30% to 45%, mice treated with the combination of cyclophosphamide and compound V demonstrate a significant inhibition of tumor volume with a T/C between 1% to 20%.

Figure 5:
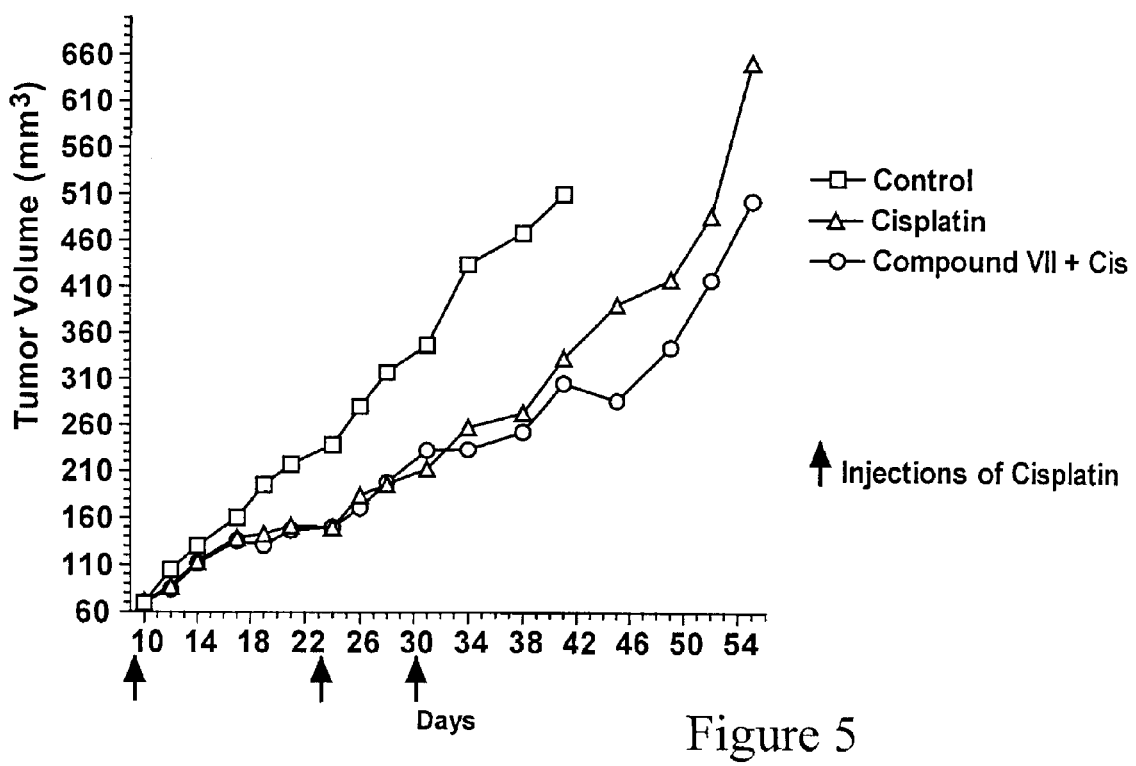
FIG. 5 shows the antitumor efficacy of oral administration of cisplatin alone compared to the combination of compound VII and cisplatin on a DA-3 breast tumor.

FIG. 5 compares the antitumor efficacy of oral administration (50 mg/kg) of cisplatin alone to the combination of compound VII and cisplatin. Cisplatin induces a significant ($p<0.01$) inhibition of tumor volume with a T/C between 40% to 77% from day 40 to 77. Mice treated with the combination of cisplatin and compound VII also demonstrate a significant ($p<0.01$) inhibition of tumor volume with a T/C between 34% to 71% from day 34 to 71.

Example 17

Antitumor Effects of Compounds on a Primary P815 Mastocytoma Tumor

The syngeneic P815 is a DBA/2 ($H-2^d$)-derived mastocytoma obtained from ATCC (TIB64). P815 cells were grown in DMEM containing 10% fetal bovine serum. At day 0, 50 μl of $5\times10^5$ viable P815 cells were intradermally injected to produce localized tumors in 6- to 8-week old DBA/2 mice. The animals were then serially monitored by manual palpation for evidence of tumor. Mice were then treated every day with oral administration of vehicle (negative control), acetylsalicylic acid (positive control, 50 mg/kg), or compound (50 mg/kg). Mice were sacrificed at day 23. Serial tumor volume was obtained by bi-dimensional diameter measurements with calipers, using the formula 0.4 $(a\times b^2)$ where "a" was the major tumor diameter and "b" the minor perpendicular diameter. Tumors were palpable, in general, 3 days to 5 days post-inoculation.

Figure 6:
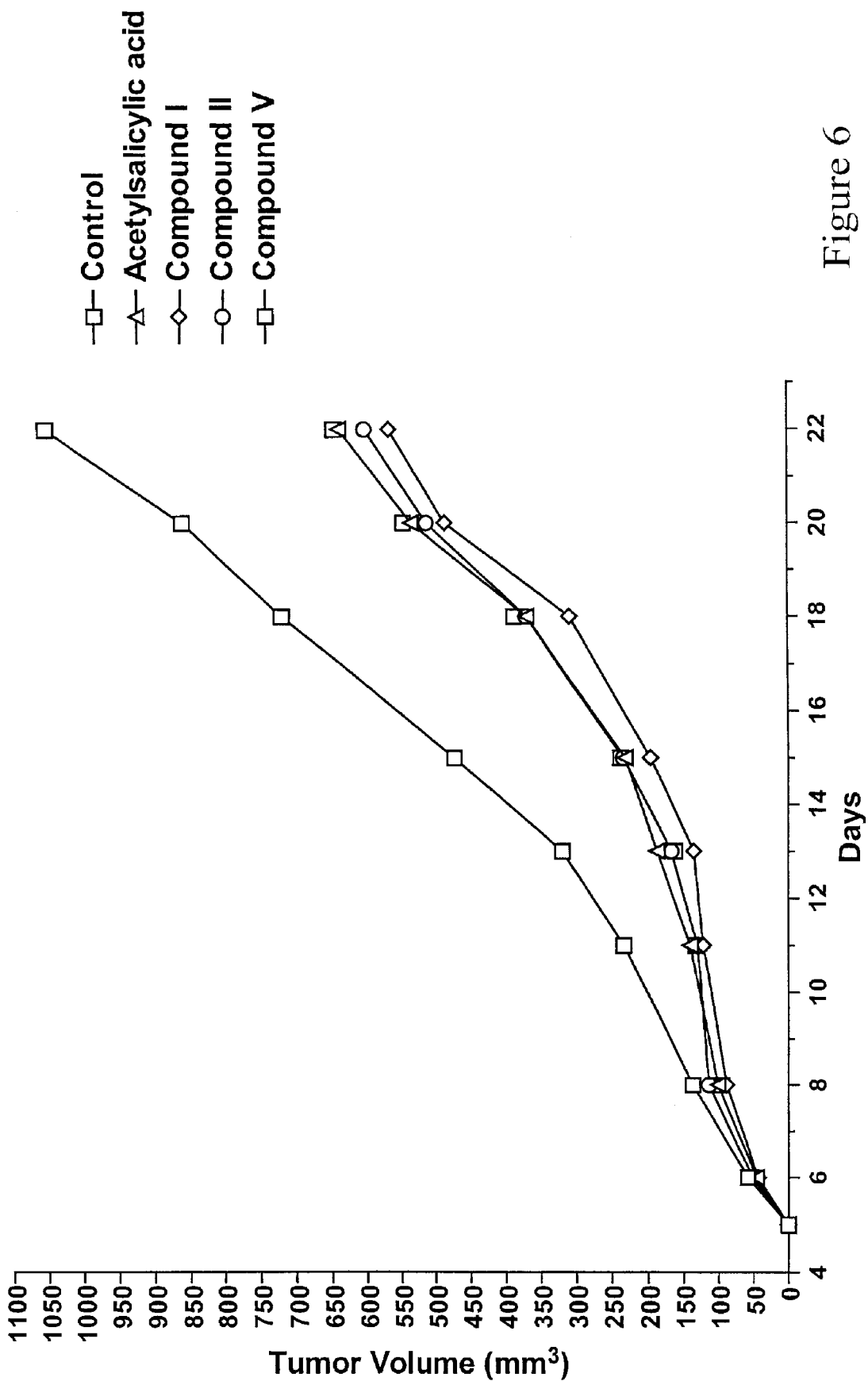
FIG. 6 shows the antitumor efficacy of compound I, compound II, compound V, or acetylsalicylic acid on a P815 mastocytoma.

FIG. 6 shows the effect of oral administration of compound I, compound II, compound V, or acetylsalicylic acid (positive control) on primary tumor P815 cells. All compounds induce a significant reduction (T/C between 40% to 50%) of tumor growth. Furthermore, the effects of all compounds were comparable to the gold standard, soluble acetylsalicylic acid.

Example 18

Antitumor Effects of Compounds on a Primary Lewis Lung LL/2 Carcinoma Tumor

The syngeneic LL/2 is a lung tumor cell line obtained from ATCC(CRL-1642). LL/2 cells were grown in DMEM containing 10% fetal bovine serum. At day 0, 50 μl of $3\times10^5$ viable LL/2 cells were intradermally injected to produce localized tumors in 6- to 8-week old mice. The animals were then serially monitored by manual palpation for evidence of tumor. Mice were then treated every day with oral administration of vehicle (negative control), or compound (50 mg/kg) and with intravenous injection of cisplatin (5 mg/kg) at day 6 and day 13. Mice were sacrificed at day 16. Serial tumor volume was obtained by bi-dimensional diameter measurements with calipers, using the formula 0.4 $(a\times b^2)$ where "a" was the major tumor diameter and "b" the minor perpendicular diameter. Tumors were palpable, in general, 3 days to 5 days post-inoculation.

Figure 7A:
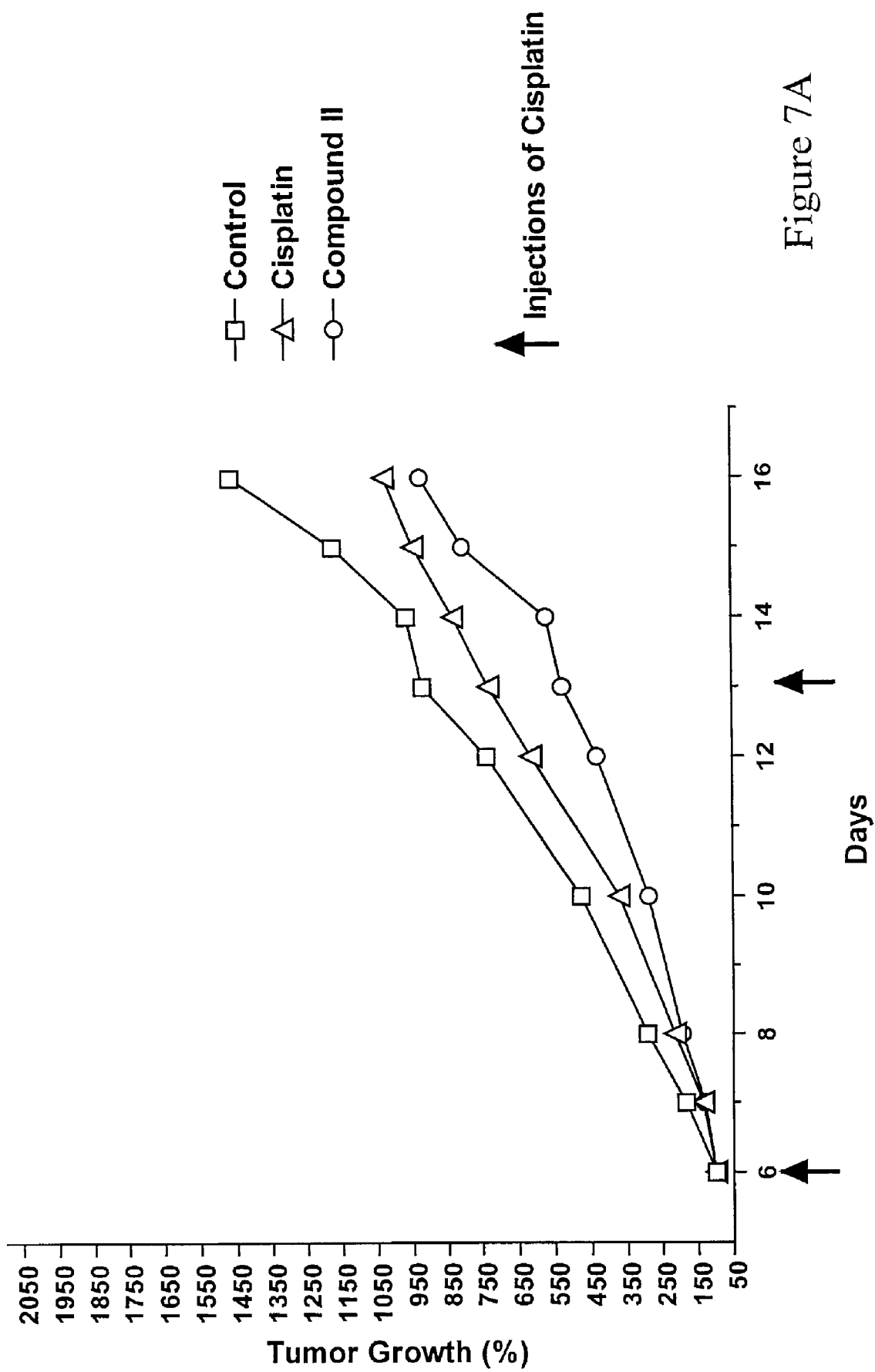
FIG. 7 shows the antitumor efficacy of compound II on a LL/2 lung tumor. The effects of compound II and cisplatin are compared in FIG. 7A. The effects of compound II alone, cyclophosphamide alone, and the combination of cyclophosphamide+compound II are compared in FIG. 7B.
Figure 7B:
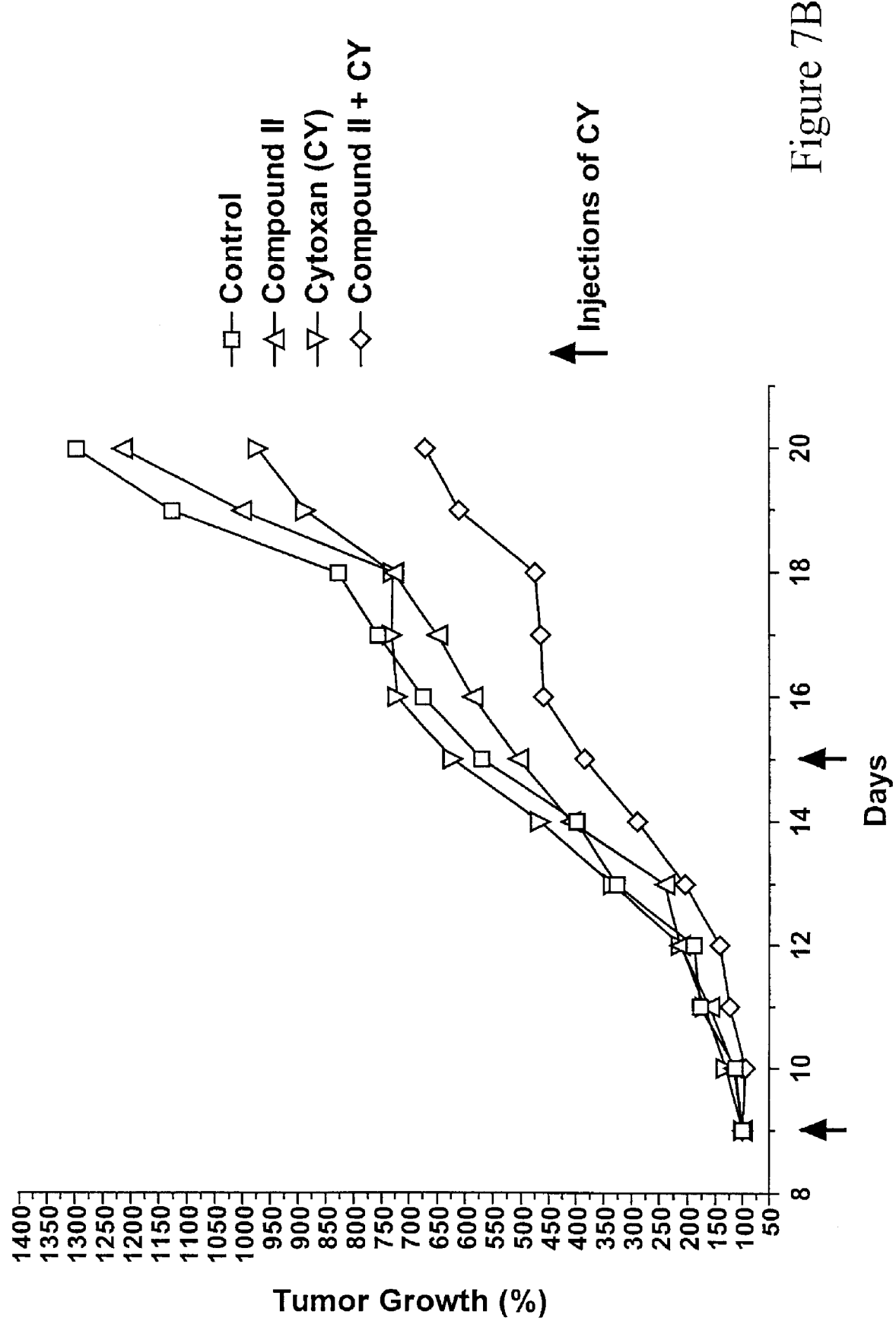

FIG. 7A shows the effect of oral administration of compound II or cisplatin (positive control) on primary tumor LL/2 cells. Compound II induces a significant reduction (T/C between 36% to 60%, $p<0.04$) of tumor growth from day 7 to day 16. Cisplatin induces a significant reduction (T/C between 42% to 84%, $p<0.04$) of tumor growth at day 7 and day 8. In another experiment, cyclophosphamide (100 mg/kg) was used as positive control and was injected at day 9 and day 15. Mice were sacrificed at day 20. FIG. 7B shows the effect of the combination therapy of cyclophosphamide and compound II. This combination therapy achieved a synergistic activity in the reduction of primary tumor LL/2 cells.

Figure 8:
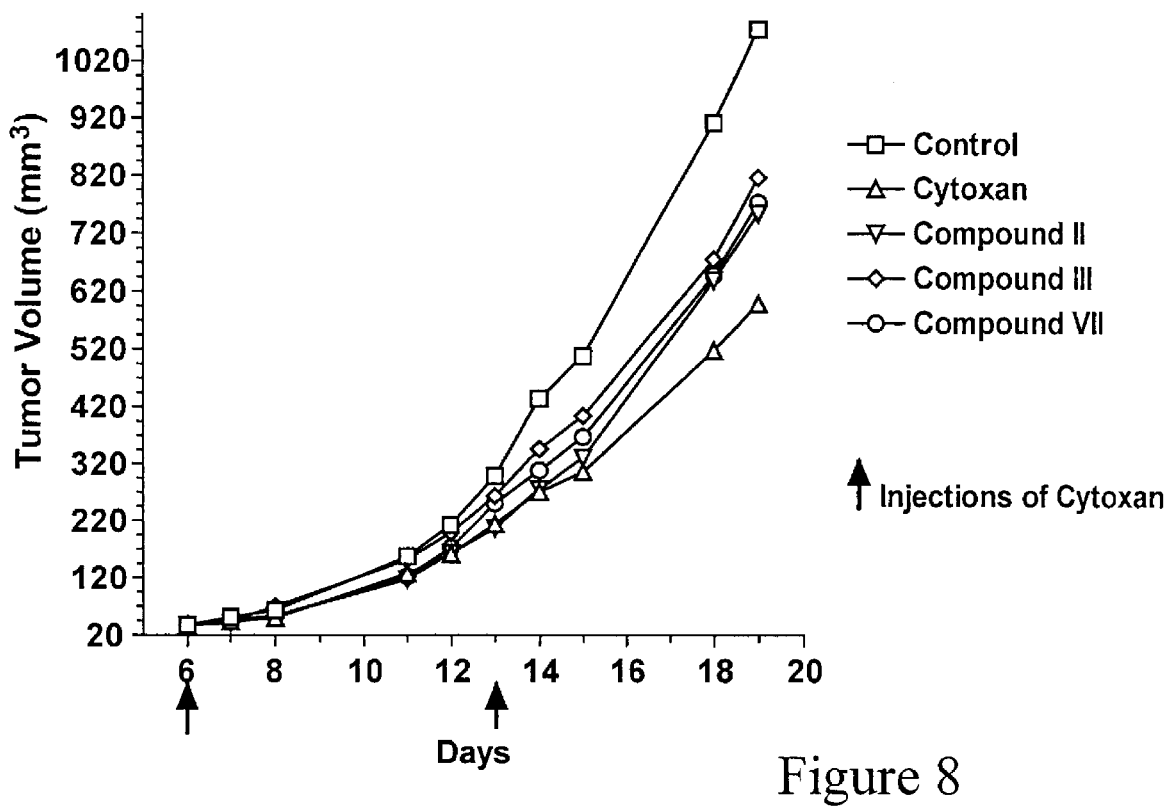
FIG. 8 shows the antitumor efficacy of compound II, compound III, compound VII, or cyclophosphamide on a LL/2 lung tumor.

FIG. 8 shows the effect of oral administration of compound II, compound III, compound VII, or cyclophosphamide (positive control) on primary tumor LL/2 cells. Compound II induces a reduction (T/C between 53% to 74%) of tumor growth. Compound III induces a reduction (T/C between 67% to 96%) of tumor growth. Compound VII induces a reduction (T/C between 72% to 85%) of tumor growth. Cyclophosphamide induces a reduction (T/C between 50% to 67%) of tumor growth.

Example 19

Antitumor Effects of Compounds on a PAN02 Pancreatic Tumor

The syngeneic PAN02 is a pancreatic tumor cell line obtained from NCl (0507232). PAN02 cells were grown in RPMI-1640 containing 10% fetal bovine serum. At day 0, 50 μl of $7.5 \times 10^5$ viable PAN02 cells were intradermally injected to produce localized tumors in 6- to 8-week old C57BL/6 mice. The animals were then serially monitored by manual palpation for evidence of tumor. Mice were then treated every day with oral administration of vehicle (negative control), or compound (50 mg/kg) and with intraperitoneal injection of gemcitabine (50 mg/kg) at day 6 and day 12. Mice were sacrificed at day 40. Serial tumor volume was obtained by bi-dimensional diameter measurements with calipers, using the formula $0.4$ $(a \times b^2)$ where "a" was the major tumor diameter and "b" the minor perpendicular diameter. Tumors were palpable, in general, 3 days to 5 days post-inoculation.

Figure 9:
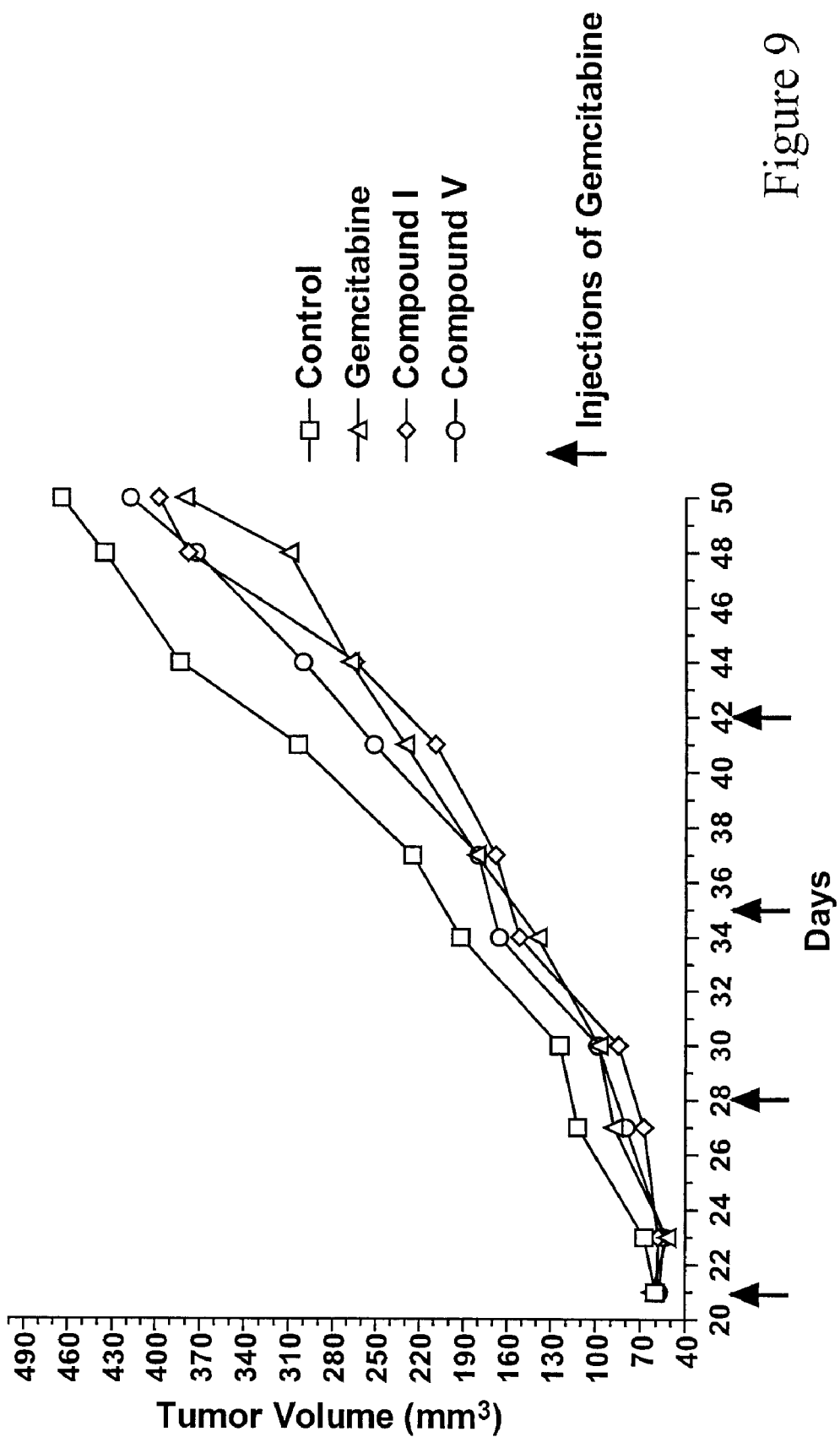
FIG. 9 shows the antitumor efficacy of compound I, compound V, or gemcitabine on a PAN02 pancreatic tumor.

FIG. 9 shows the effect of oral administration of compound I, compound V, or gemcitabine (positive control) on primary tumor PAN02 cells. Both compounds I and V induce a weak reduction (T/C between 17% to 67% and 40% to 84%, respectively) of tumor growth. Furthermore, the effects of all compounds were comparable to the gold standard gemcitabine (T/C between 52% to 77%), used for the therapy of pancreatic cancer.

Example 20

Antitumor Effects of Compounds on Xenograft Human Prostate PC-3 Tumor

The xenogenic human prostate tumor PC-3 was obtained from ATCC(CRL1435). PC-3 cells were grown in RPMI-1640 containing 10% fetal bovine serum. At day 0, 50 μl of viable PC-3 (1.5 to $2 \times 10^6$) cells were intradermally injected to produce localized tumors in 6- to 8-week old male CD1 nu/nu mice. The animals were then serially monitored by manual palpation for evidence of tumor. When the tumors reached a satisfactory volume, mice were randomized, and then treated four, three, and three times a week for the first, second, and third week respectively with intravenous injection of vehicle (negative control), cyclophosphamide (positive control, 100 mg/kg), or compound (5 mg/kg). Mice were sacrificed between day 56 to day 65. Serial tumor volume was obtained by bi-dimensional diameter measurements with calipers, using the formula $0.4$ $(a \times b^2)$ where "a" was the major tumor diameter and "b" the minor perpendicular diameter.

Figure 10A:
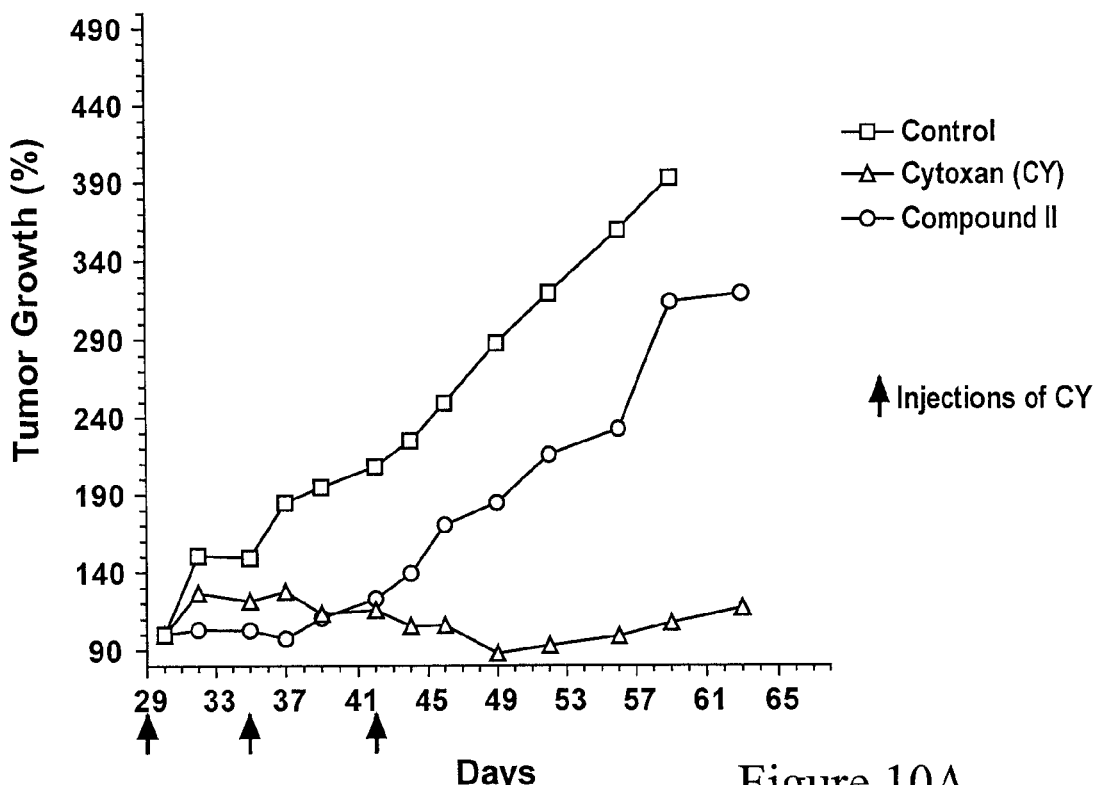
FIG. 10 shows the antitumor efficacy of compounds on a PC-3 prostate tumor: compound II alone (FIG. 10A), combination of cyclophosphamide+compound II (FIG. 10B), and comparing compound V to the combination of cyclophosphamide+compound V (FIG. 10C).

FIG. 10A shows the effect of compound II or cyclophosphamide on xenograft human prostate PC-3 tumor. Compound II induces a significant reduction (T/C between 29% to 75%) of tumor growth. Cyclophosphamide induces a significant reduction (T/C between 1% to 52%) of tumor growth. Furthermore, compound II demonstrated a cytostatic (no growth) effect up to day 42.

Figure 10B:
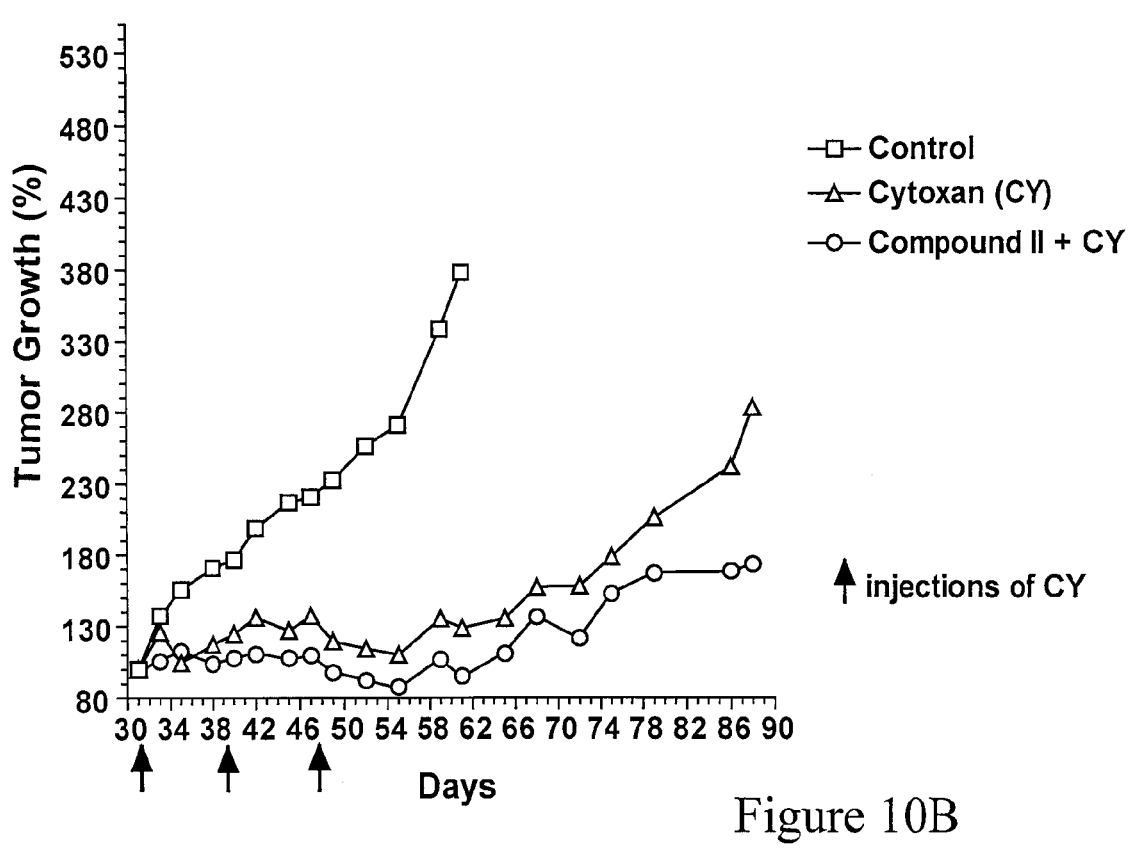

FIG. 10B shows the effect of compound II, cyclophosphamide, or the combination of compound II and cyclophosphamide on xenograft human prostate PC-3 tumor. Cyclophosphamide induces a significant reduction (T/C between 8% to 31%) of tumor growth. Treatment with the combination of compound II and cyclophosphamide resulted in a significant reduction (T/C between 1% to 23%) followed by tumor regression. The regrowth of the tumor was faster in the cyclophosphamide-treated group after termination of the treatment at day 48.

Figure 10C:
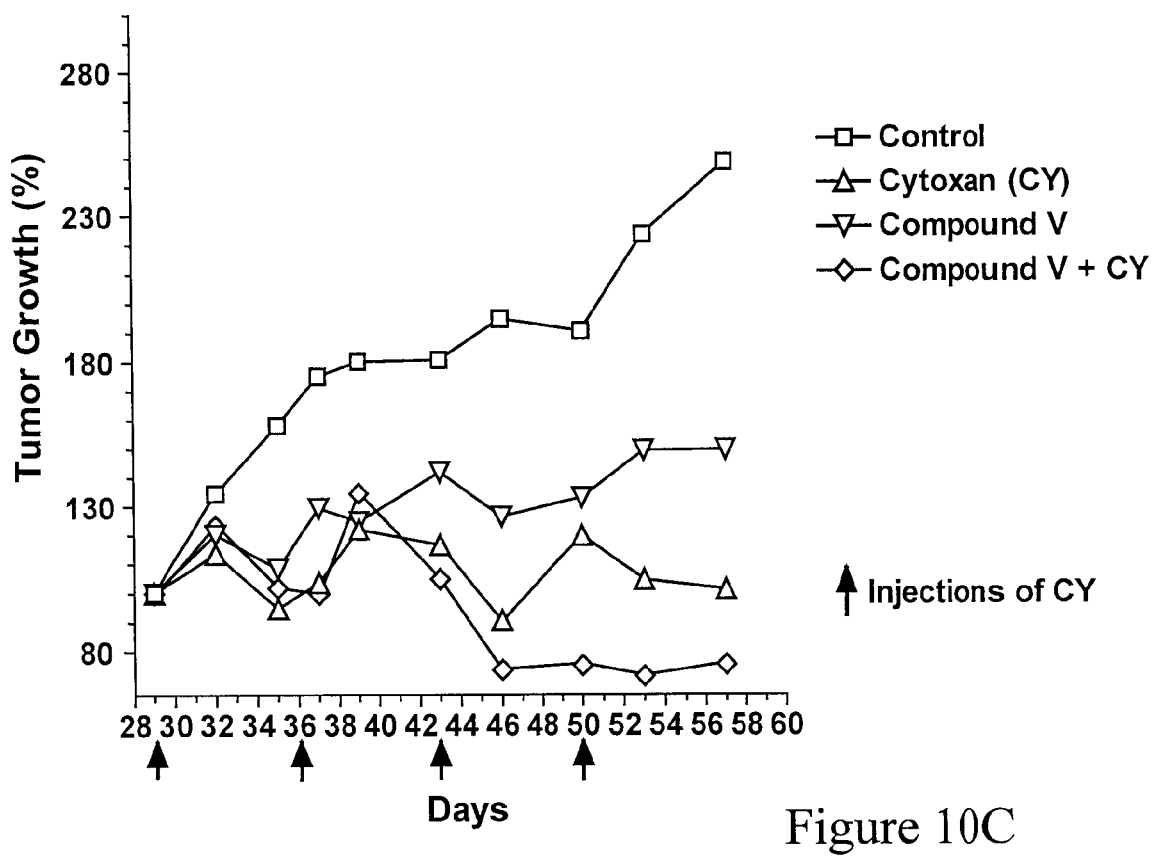

FIG. 10C shows the antitumor efficacy of oral administration of compound V with or without cyclophosphamide on xenograft human prostate PC-3 tumor. Oral administration of compound V induces a significant ($p<0.05$) inhibition of tumor volume with a T/C between 14% to 40%. Cyclophosphamide induces a significant inhibition ($p<0.05$) of tumor volume with a T/C between 1% to 39%. Mice treated with the combination of cyclophosphamide and oral administration of compound V demonstrated a significant ($p<0.01$) inhibition of tumor volume with a T/C between 1% to 40% accompanied with tumor regression.

Anti-Inflammatory Activity

Example 21

Effect of compounds on TNFα-Induced Apoptosis in WEHI-13VAR Cell Line

Effect of compounds on TNFα-induced apoptosis was measured by a standard biological assay using WEHI-13VAR cells. These cells undergo apoptosis when they are incubated in the presence of TNFα and actinomycin D. $2 \times 10^4$ WEHI-13VAR cells were incubated in RPMI supplemented with 1% sodium pyruvate and 10% FBS, overnight at 37° C. for cell adherence. The cells were then cultured in the presence of 1 μg/ml of actimomycin D (to inhibit protein synthesis) and 0.04 nM TNFα with or without compounds at 37° C. After 16 hr to 24 hr, 50 μl of a solution of 2 mg/ml of MIT was added to each well and the plate was then incubated for 4 hr at 37° C. Only viable cells metabolize MTT to form formazan salt, which is detectable by the measurement of absorbance at 570 nm. After the incubation, the plate was inverted to remove medium and dead cells. 150 μDMSO was added to each well to stop the reaction and solubilize the formazan salt. Optical density was read on a Bio-Tek EL 800 UV microplate reader. A decrease in the optical density is direct evidence of cell apoptosis induced by TNFα. Compounds were also compared to the activity of an anti-TNFα neutralizing antibody.

Table 2 represents the percentage of TNFα inhibition (apoptosis) of compounds tested in the cell-based TNFα sensitive WEHI-13VAR cell proliferation assay. The compounds demonstrated a TNFα inhibitory activity in the range of 40-80%. In comparison, TNFα antibody demonstrated a TNFα inhibitory activity of 90-95%. This data illustrates the ability of compounds of this invention to inhibit the apoptotic activity of TNFα, on TNFα sensitive WEHI-13VAR cells.

TABLE 2

Effect of compounds on TNF-α inhibition (apoptosis).

WEHI-13VAR assay
(% inhibition of apoptosis)

| Compound | $4 \times 10^{-5}$ M | $2 \times 10^{-5}$ M | $1 \times 10^{-5}$ M | $5 \times 10^{-6}$ M |
|---|---|---|---|---|
| I | — | 58.9 | 33.1 | 17.9 |
| II | 78.9 | 83.8 | 64.2 | 45.2 |
| III | — | 89.7 | 52.0 | 20.4 |
| IV | 47.2 | 31.6 | 13.1 | 3.7 |
| V | 75.9 | 51.9 | 22.2 | 8.2 |
| VI | 89.5 | 74.1 | 54.8 | 28.2 |
| VII | 118.1 | 99.9 | 65.8 | 30.0 |
| VIII | 55.6 | 48.1 | 35.6 | 17.0 |
| IX | 65.5 | 46.7 | 29.8 | 13.2 |
| X | 53.9 | 79.9 | 44.4 | 19.4 |
| XI | 35.0 | 23.7 | 14.6 | 9.9 |

Example 22

Effect of Compounds on LPS-Induced TNFα Production in Mouse J774A.1 Cell Line

Effect of compounds on TNFα production was measured by ELISA using J774A.1 cells stimulated by LPS. J774A.1 cells were cultured in the presence or absence of LPS and compound. Cells were cultured for 24 hr at 37° C. and thereafter the supernatants were collected for the determination of the concentration of TNFα by ELISA as recommended by the manufacturer (BD Biosciences). Data was analyzed in Microsoft Excel software and the concentration of compound which inhibits 50% of TNFα production ($IC_{50}$) was calculated using Prism software.

Table 3 summarizes the effect of compounds on TNFα production induced by LPS on J774A.1 cells.

TABLE 3

Effect of compounds on LPS-induced TNFα production.

| Compound | $IC_{50}$ (µM) |
|---|---|
| I | 29 |
| V | 13 |

Example 23

Effect of Compounds on LPS-Induced $PGE_2$ Production in Mouse J774A.1 Cell Line Effect of compounds on $PGE_2$ production was measured by ELISA using J774A.1 cells stimulated by LPS. J774A.1 cells were cultured in the presence or absence of LPS and compound. Cells were cultured for 24 hr at 37° C. and thereafter the supernatants were collected for the determination of the concentration of $PGE_2$ by ELISA as recommended by the manufacturer (GE Healthcare). Data was analyzed in Microsoft Excel software and the concentration of compound which inhibits 50% of $PGE_2$ production ($IC_{50}$) was calculated using Prism software.

Figure 11:
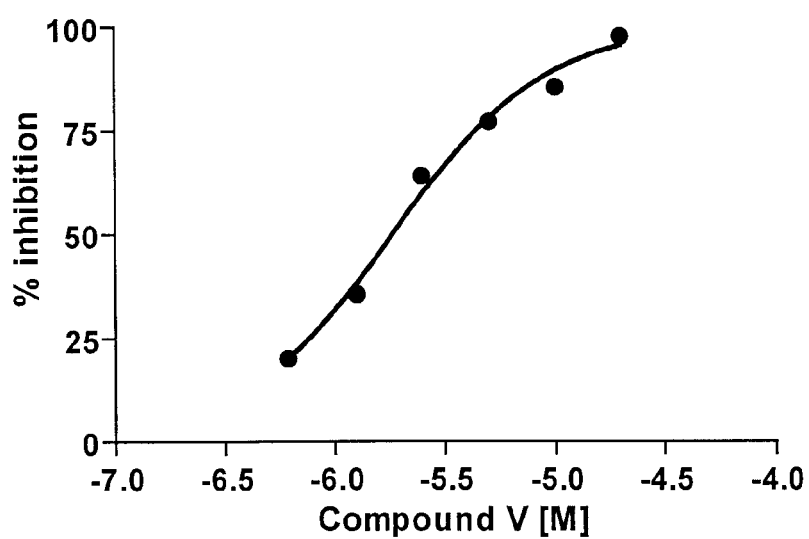
FIG. 11 shows the effect of compound V on the inhibition of $PGE_2$ released by LPS induction from J774A.1 cells.

FIG. 11 shows the effect of compound V on the production of $PGE_2$ in LPS-stimulated J774A.1. Compound V inhibits the production of $PGE_2$ with an $IC_{50}$ of 2 µM.

Example 24

Effect of Compounds on Peripheral Blood Mononuclear Leukocytes (PBML) Cells Cytotoxicity, DNA, RNA, and Protein Synthesis PBML were obtained from the peripheral blood of healthy volunteers. Blood was submitted to gradient centrifugation with Lympholyte-Poly media (Cedarlane, Hornby, Canada). The layer containing the mononuclear leukocytes was collected and the cells washed three times in PBS. Cells were then suspended in RPMI (Gibco, Burlington, Canada) supplemented with 10% FBS (Hyclone, Logan USA). Viability was greater than 99% as determined by trypan blue exclusion.

PBML were resuspended at $2 \times 10^6$ cells/ml. 100 µl of PBML ($2 \times 10^5$ cells) were incubated in a 96-well microtiter plate for 48 hr in the presence or absence of compound. Cells were quiescent or stimulated with concanavalin A (con A; T-cells) or pokeweed mitogen (PWM; B-cells). After incubation, cells were treated with MTT (cytotoxicity) or pulsed with 1 µCi of [$^3$H]-thymidine (DNA synthesis), [$^3$H]-uridine (RNA synthesis), or [$^3$H]-leucine (protein synthesis) for 6 hr. Plates were harvested on a Tomteck and counted on a Microbeta β-counter.

Table 4 summarizes the effect of compounds on cell cytotoxicity, DNA, RNA, and protein synthesis on human peripheral blood mononuclear leukocytes (PBML). Cell cytotoxicity was not observed. However, all compounds suppress DNA when PBML are stimulated with con A, a mitogen stimulating T-cell proliferation and PWM, a mitogen stimulating B-cell proliferation. RNA synthesis is inhibited in both resting and stimulated (con A and PWM) PBML. However, only compounds I and II inhibit protein synthesis in stimulated PBML. These results suggest a suppression of both T and B cells. These cells are strongly implicated in inflammatory diseases such as autoimmune diseases.

TABLE 4

Effect of compounds on resting or stimulated PBML cytotoxicity, DNA, RNA, and protein synthesis.

PBML ($IC_{50}$ Results in µM)

| Compound | Cytotoxicity | | | DNA Synthesis | | | RNA Synthesis | | | Protein Synthesis | | |
|---|---|---|---|---|---|---|---|---|---|---|---|---|
| | Resting | Con A | PWM | Resting | Con A | PWM | Resting | Con A | PWM | Resting | Con A | PWM |
| I | >10 | >10 | >10 | >10 | 3.7 | 2.8 | 6.8 | nd | 2.2 | >10 | 4.4 | 9.9 |
| II | >10 | >10 | >10 | >10 | 2.9 | 1.7 | 5.8 | nd | 1.1 | >10 | 6.4 | 5.7 |
| V | >10 | >10 | >10 | >10 | 8 | 6.1 | 7.4 | 6 | 4.5 | >10 | >10 | >10 | nd = not determined

Example 25

Effects of Compounds on Systemic Lupus Erythematosus (SLE)

New Zealand mice of the F1 hybrid cross NZB×NZW develop most of the autoimmune abnormalities seen in human SLE and die from SLE-like immune complex (IC)-mediated glomerulonephritis. The mice develop high titers of anti-DNA (double-strand and single-strand) and nuclear extract (NE) antibodies, as well as SLE-related clinical manifestations including leukopenia, thrombocytopenia, proteinuria, and glomerulonephritis. These mice develop anti-DNA antibodies after the age of three months, with a peak of anti-DNA antibody response occurring at seven months. Subsequently, the serum concentration of anti-DNA antibodies declines, presumably as a consequence of progressive uremia. The first serological manifestations of the disease occurs at about 150 days (i.e., five months). Their survival is evaluated at approximately 250 days.

Figure 12:
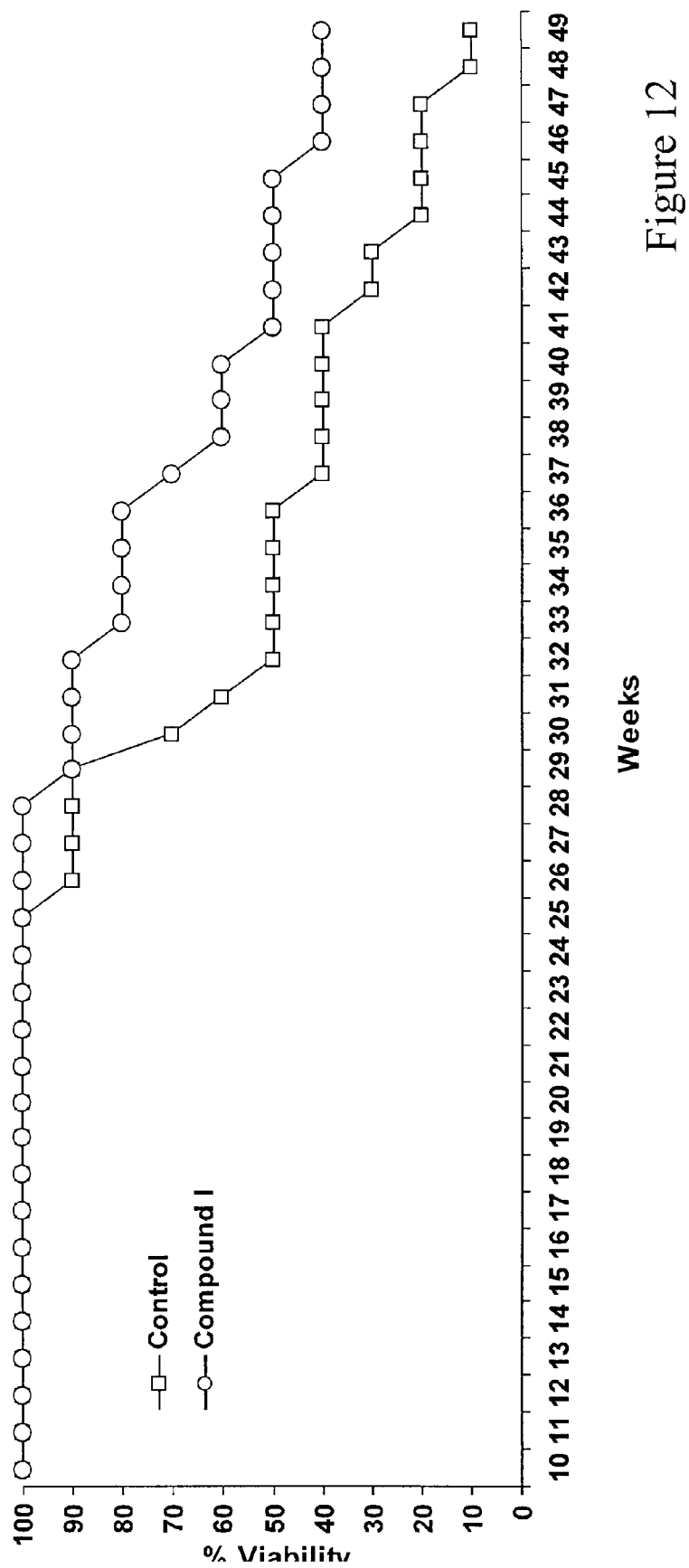
FIG. 12 shows the effect of compound I on mortality of NZB×NZW mice.

FIG. 12 shows the effect of compound I on the mortality of the NZB×NZW mice. Intravenous administration of compound or vehicle was undertaken once a week from week 10 to week 46. Results indicate that compound I reduces the mortality of NZB×NZW mice.

Example 26

Effects of Compounds on Delayed-Type Hypersensitivity (DTH)

Compounds were tested for their ability to treat oxazolone-induced delayed-type hypersensitivity (DTH) in mice. On day 0, mice were sensitized with 100 µl, of oxazolone in 5% acetone. On day 0, day 1, and day 2, mice were treated by intravenous (IV) or oral (PO) administrations of the vehicle (control) or methotrexate (MTX; positive control/IV) or hydrocortisone (positive control/PO) or the compound at concentration lower than or equal to 50 mg/kg or as specified. Mice were challenged with an application of 50 µl of oxazolone on the surface of the right ear (first challenge, day 3; second challenge, day 10). Ear thickness was measured on day 4 to day 7, and on day 11 to 14. Redness and crust formation was also observed. Mice were sacrificed on day 14. $T_{DTH}$ (CD4) cells play an important role in regulating the intensity of the DTH response. Compounds may exert an inhibitory influence on the DTH response through its inhibition of T-cell activation and DNA, RNA, and/or protein synthesis.

Figure 13A:
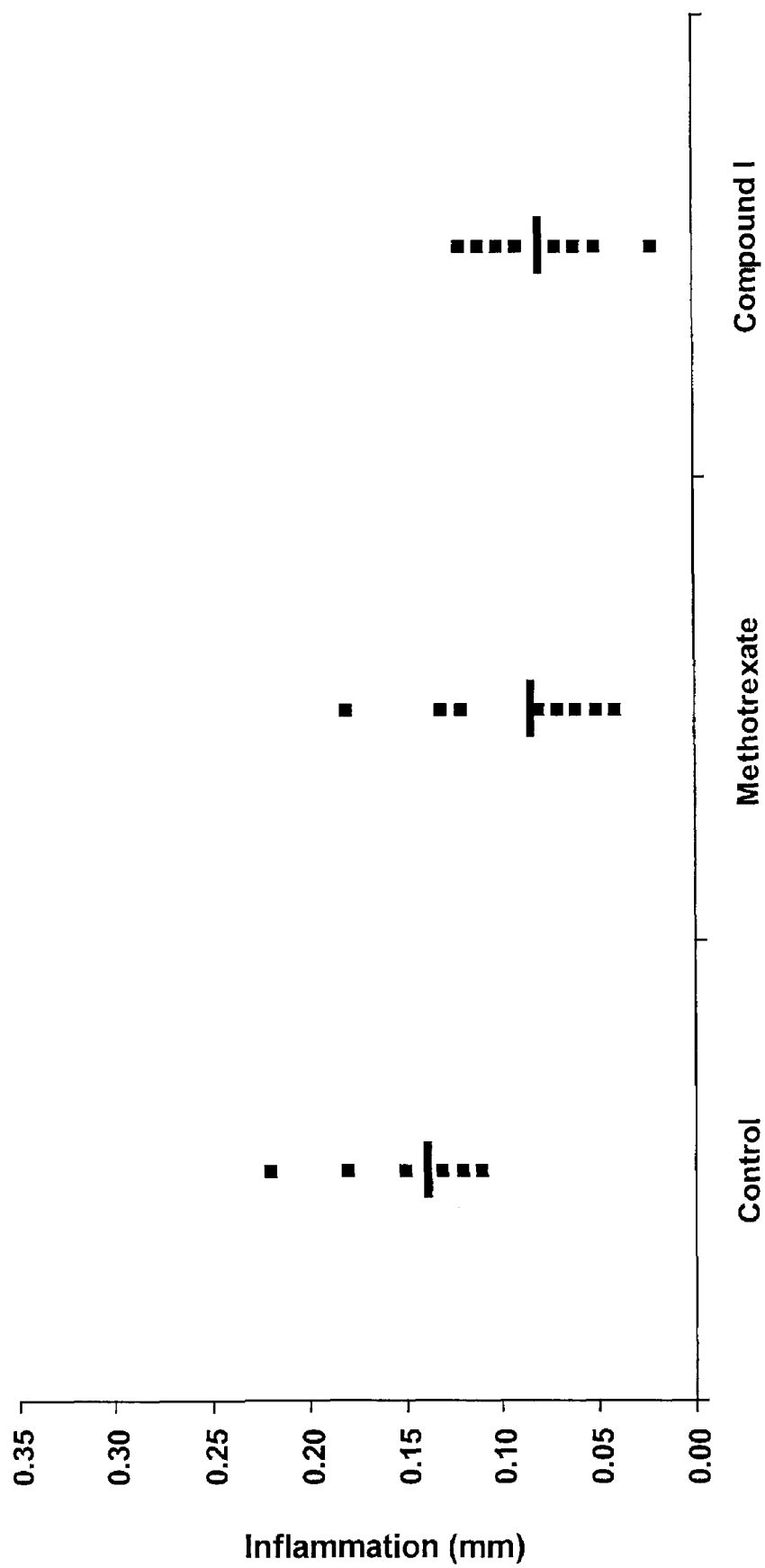
FIG. 13 shows the effect of intravenous administration of compound I on the development of delayed type hypersensitivity (DTH): primary challenge (FIG. 13A) and secondary challenge (FIG. 13B).
Figure 13B:
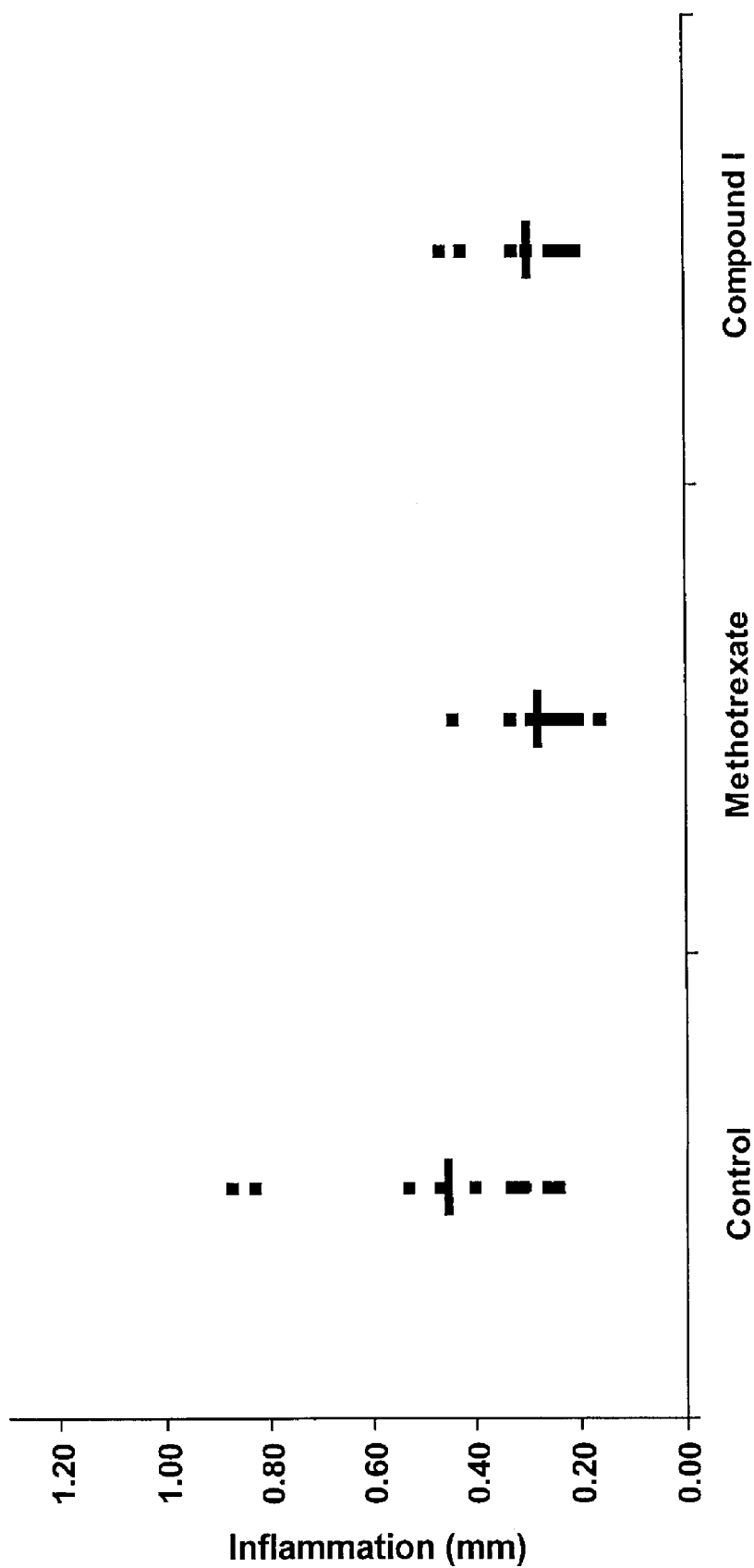

As shown in FIG. 13A, intravenous administration (25 mg/kg) of compound I induces a significant reduction of the inflammation induced after the first challenge of oxazolone as seen by decreased ear thickness. Furthermore, the inhibition of inflammation induced by compound I was comparable to the results obtained by an immunosuppressive dose of methotrexate. Intravenous administration (25 mg/kg) of compound I induces a significant reduction of the inflammation induced after the second challenge of oxazolone as seen by decreased ear thickness (FIG. 13B). Furthermore, the inhibition of inflammation induced by compound I was comparable to the results obtained by an immunosuppressive dose of methotrexate.

Figure 14A:
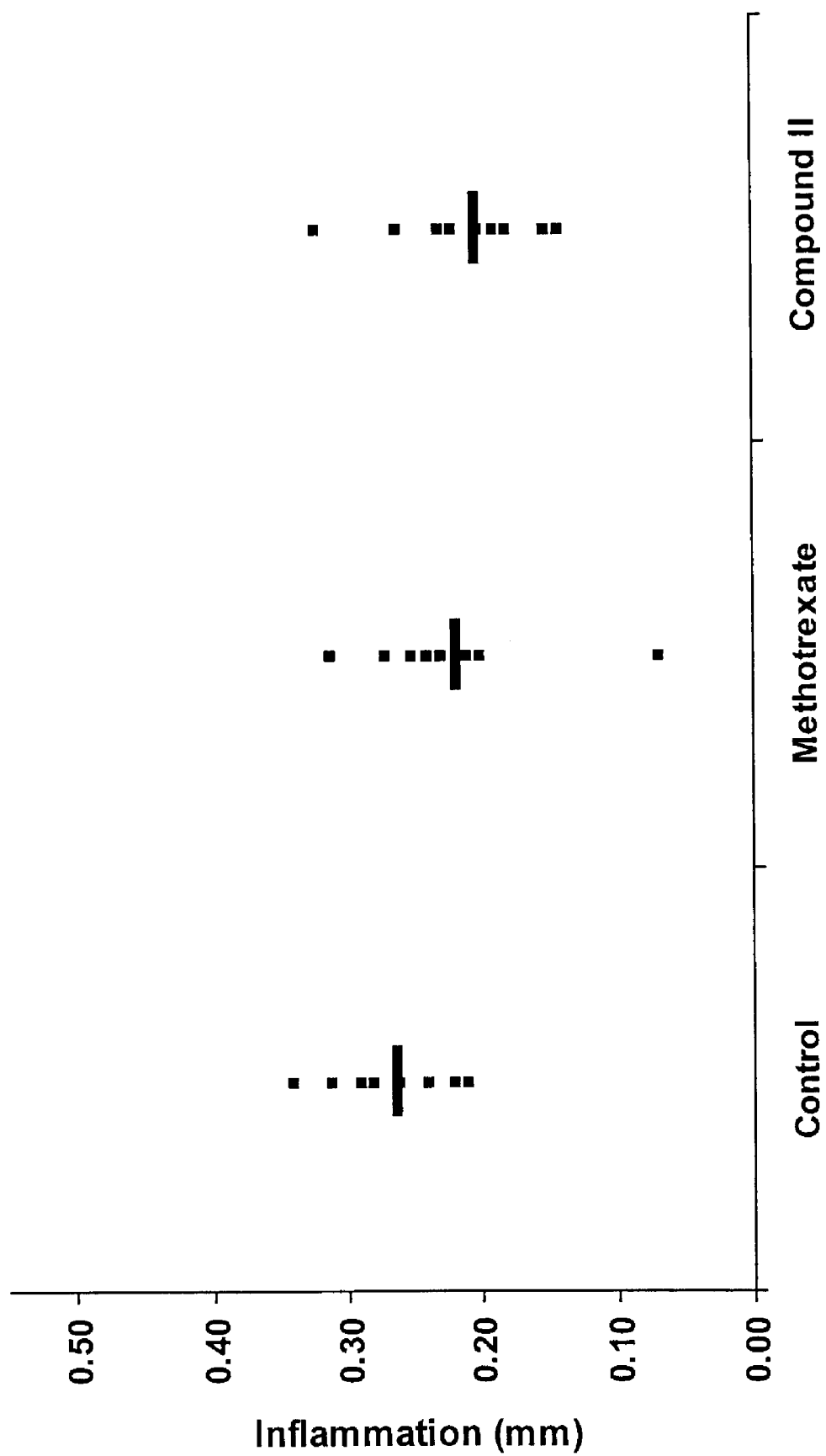
FIG. 14 shows the effect of intravenous administration of compound II on the development of delayed type hypersensitivity (DTH): primary challenge (FIG. 14A) and secondary challenge (FIG. 14B).
Figure 14B:
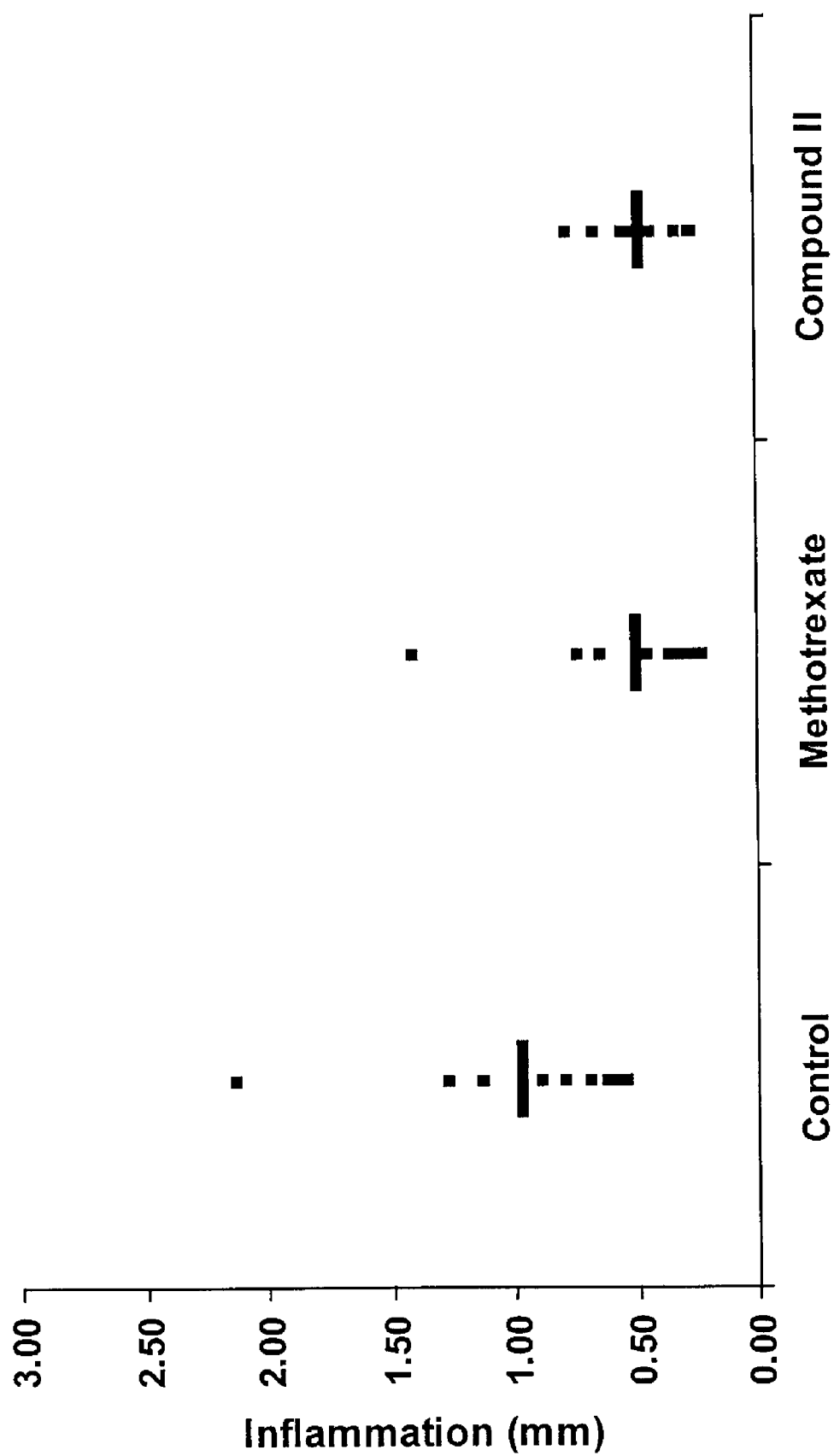

As shown in FIG. 14A, intravenous administration (5 mg/kg) of compound II induces a significant reduction of the inflammation induced after the first challenge of oxazolone as seen by decreased ear thickness. Furthermore, the inhibition of inflammation induced by compound II was comparable to the results obtained by an immunosuppressive dose of methotrexate. Intravenous administration (5 mg/kg) of compound II induces a significant reduction of the inflammation induced after the second challenge of oxazolone as seen by decreased ear thickness (FIG. 14B). Furthermore, the inhibition of inflammation induced by compound II was comparable to the results obtained by an immunosuppressive dose of methotrexate.

Figure 15:
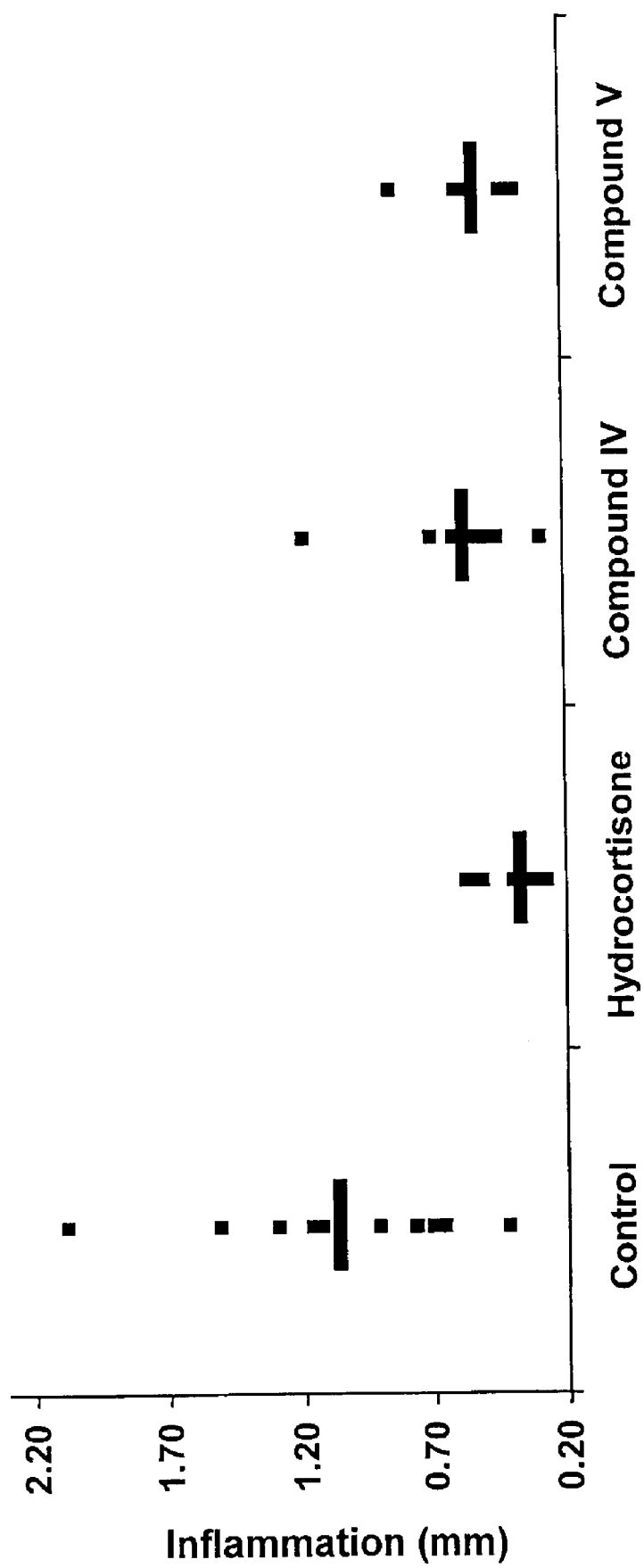
FIG. 15 shows the effect of oral administration of compound IV or compound V on inflammation as measured by ear thickness after DTH.

As shown in FIG. 15, oral administration (50 mg/kg) of compound IV or compound V induces a significant reduction of the inflammation as seen by decreased ear thickness. Furthermore, the inhibition of inflammation induced by compound IV or compound V was comparable to the result obtained by a therapeutic dose (50 mg/kg) of hydrocortisone.

Figure 16A:
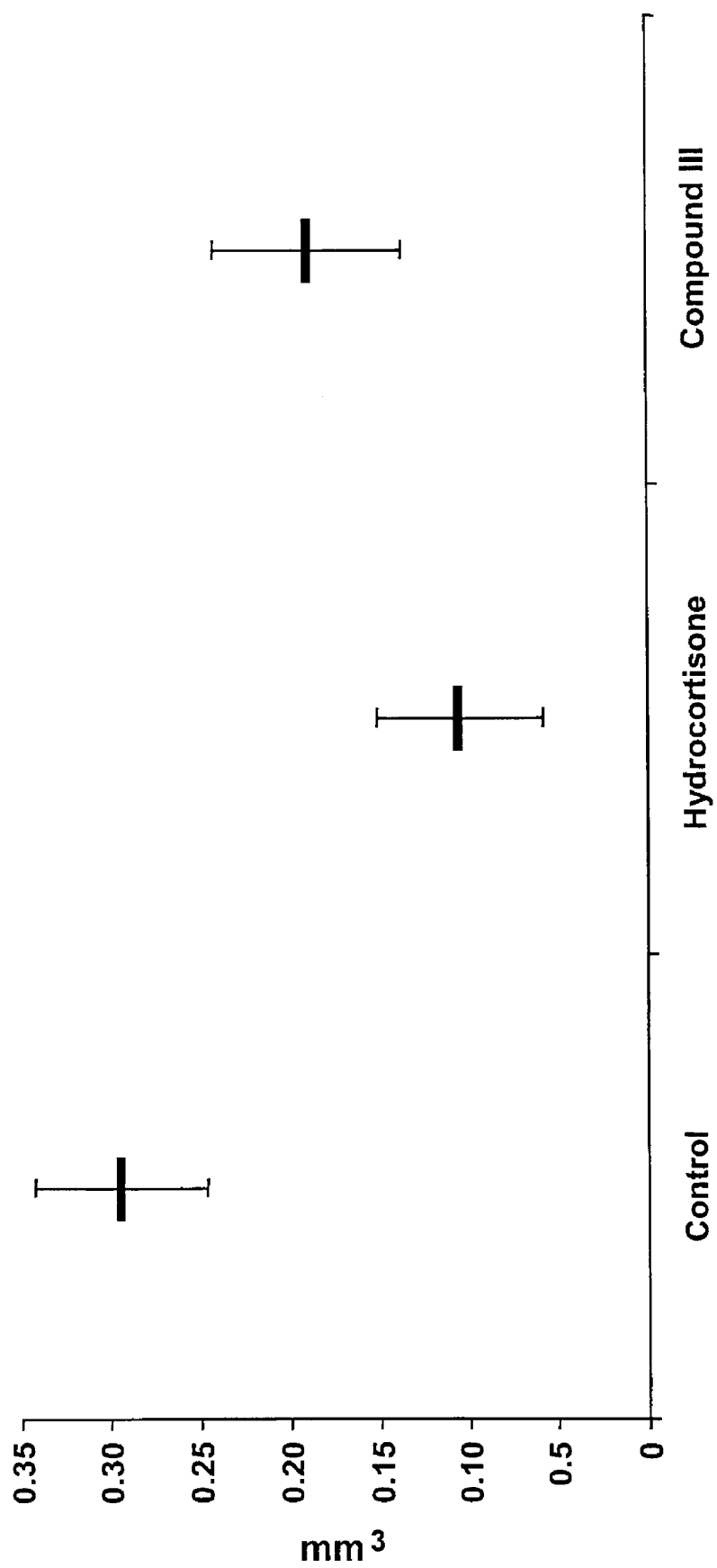
FIG. 16 shows the effect of oral administration of compound III on the development of delayed type hypersensitivity (DTH): primary challenge (FIG. 16A) and secondary challenge (FIG. 16B).
Figure 16B:
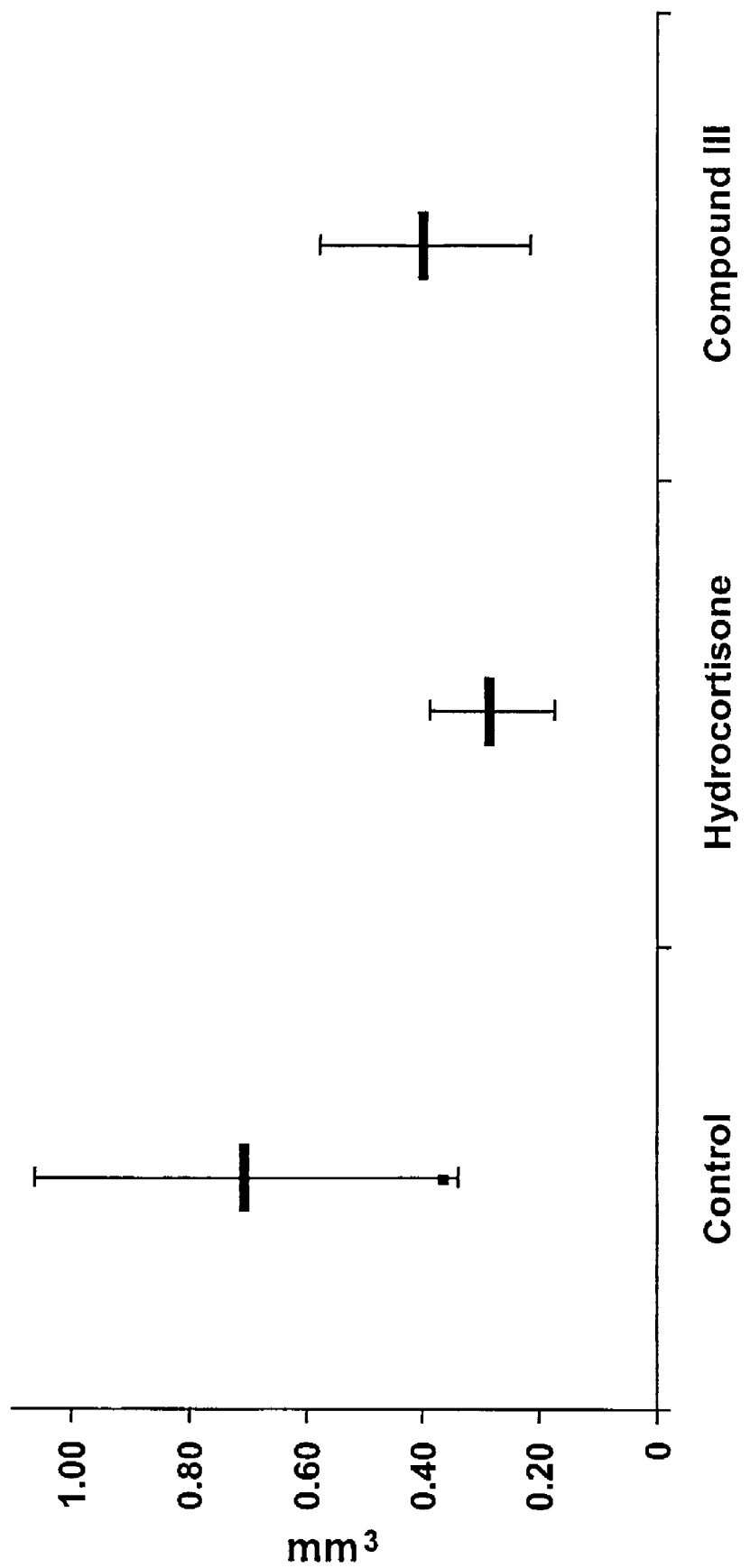

FIG. 16 shows the effect of oral administration of 50 mg/kg of compound III after the first (FIG. 16A) and second (FIG. 16B) challenge of oxazolone. Compound III induces a significant reduction of the inflammation as seen by decreased ear thickness in both challenges.

Figure 17:
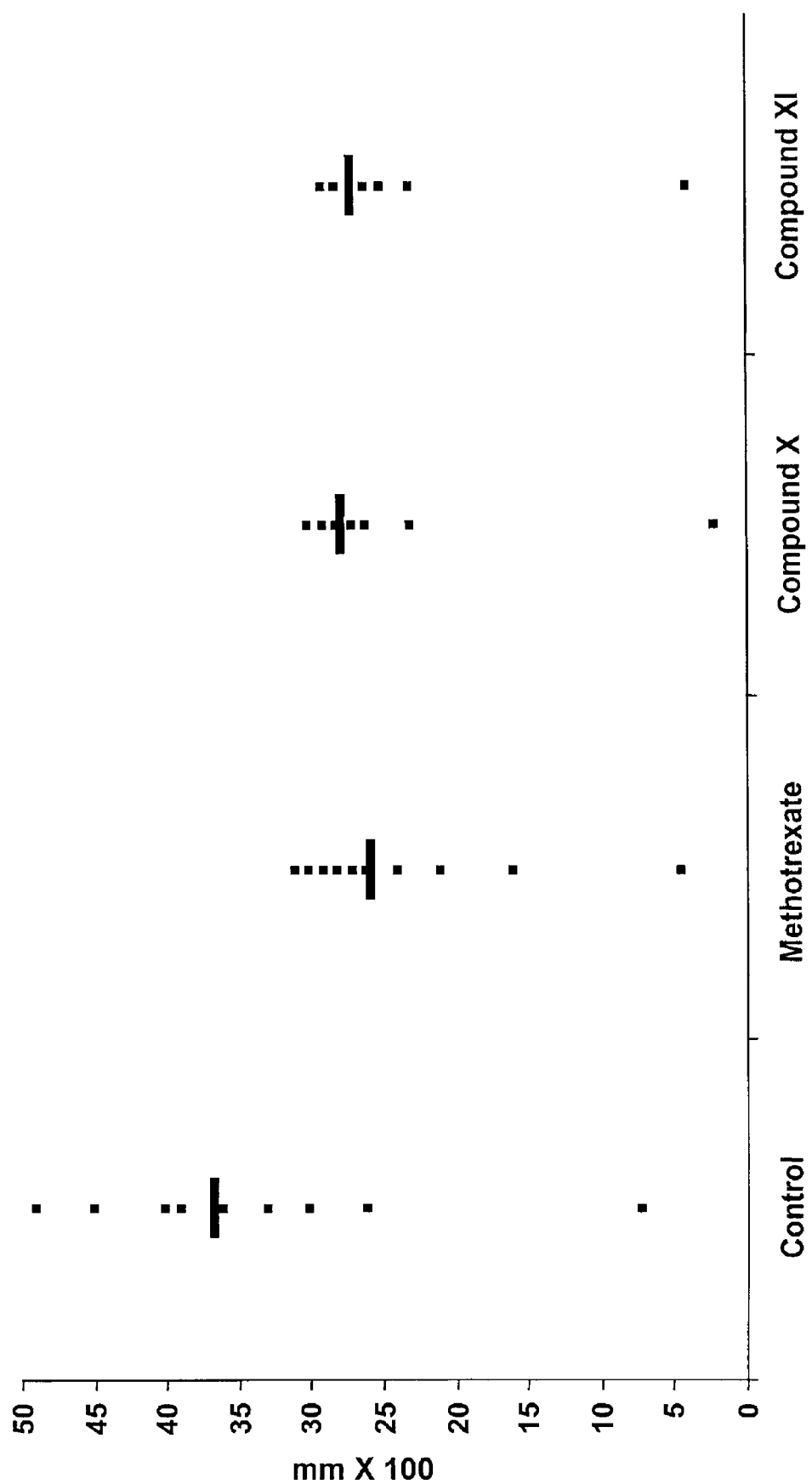
FIG. 17 shows the effect of intravenous administration of compound X or compound XI on inflammation as measured by ear thickness after DTH.

FIG. 17 shows the effect of intravenous administration of 5 mg/kg or 25 mg/kg of compound X or compound XI, respectively, after the first challenge of oxazolone. Compounds X and XI induce a significant reduction of the inflammation as seen by lower ear thickness. Furthermore, the inhibition of inflammation induced by compound X or XI was comparable to the results obtained by an immunosuppressive dose of methotrexate.

Example 27

Effects of compounds on Freund's Adjuvant-Induced Arthritis (AIA)

AIA was induced in female Lewis rats by the injection of lyophilized *Mycobacterium butyricum* suspended in mineral oil into the footpad. The development of arthritis was monitored over a 3-week period post-adjuvant injection. Inflammation peaks at day 3 following the adjuvant administration. Immune activation appears around day 10 to day 16. Compounds were orally administered from day −3 to day 21. Body weight was recorded. The arthritis index, which is a measure of inflammation (edema), redness, and stiffness of the articulations, was used to monitor the development of the disease. The degree of arthritis was determined by measuring two perpendicular diameters of the ankles in the mediolateral and dorsoventral planes using a caliper. Joint circumference in millimeters is then calculated using a geometric formula.

Figure 18:
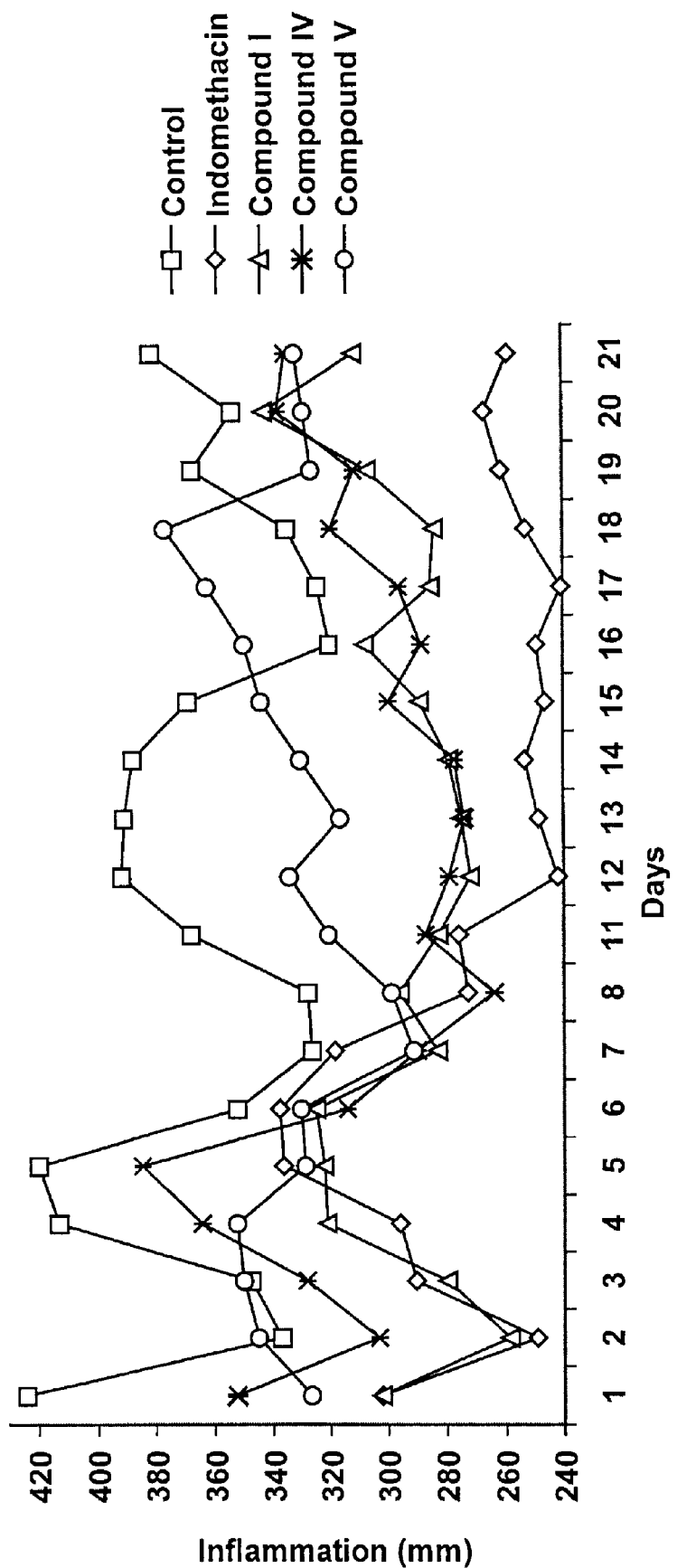
FIG. 18 shows the effect of oral administration of compound I, compound IV, or compound V on adjuvant-induced arthritis (AIA).

As shown in FIG. 18, 100% of the animals rapidly developed synovitis. A significant reduction in the severity of arthritis (inflammatory index) was observed by oral administration of indomethacin (positive control) from day 1 to day 5 and by day 8 and over. Similar reduction of the inflammatory index was also observed with compounds from day 1 to day 4 and by day 8 to day 16.

Example 28

Effect of Compounds on Air-Pouch Model of Inflammation

LPS-induced inflammation in the rat air-pouch model is believed to mimic the pathological process occurring in joint diseases such as arthritis. This is because the connective tissues formed along the air pouch are similar to those found in chronic joint diseases. LPS-induced inflammation and chronic joint diseases share other features, including markedly elevated $PGE_2$, neutrophil infiltration, cytokine formation, and tissue damage.

An air cavity was produced at day −6 by subcutaneous injection of 20 ml of sterile air into the intrascapular area of the back of male Lewis rats (175 to 200 g). An additional 10 ml of air was injected into the cavity at day −3 to keep the space open. At day 0, compounds were administered intravenously and one hour later lipopolysaccharide (LPS: 2.5 ml of 2 μg/ml in PBS) was injected into the pouch to produce an inflammatory reaction. After 2 hr, 4 hr, or 18 hr of LPS treatment, animals were euthanized by $CO_2$ asphyxiation and 5 ml of PBS/heparin (10 U/ml)/indomethacin (36 μg/ml) was injected into the pouch. The pouch fluid was collected. The volume of exudates was measured and the number of leukocytes present in the exudates was determined with a Coulter counter. The differential count was determined by Wright-Giemsa staining. $PGE_2$, $LTB_4$, MCP, and $TNF\alpha$ were determined in the pouch exudates by specific ELISAs.

Figure 19:
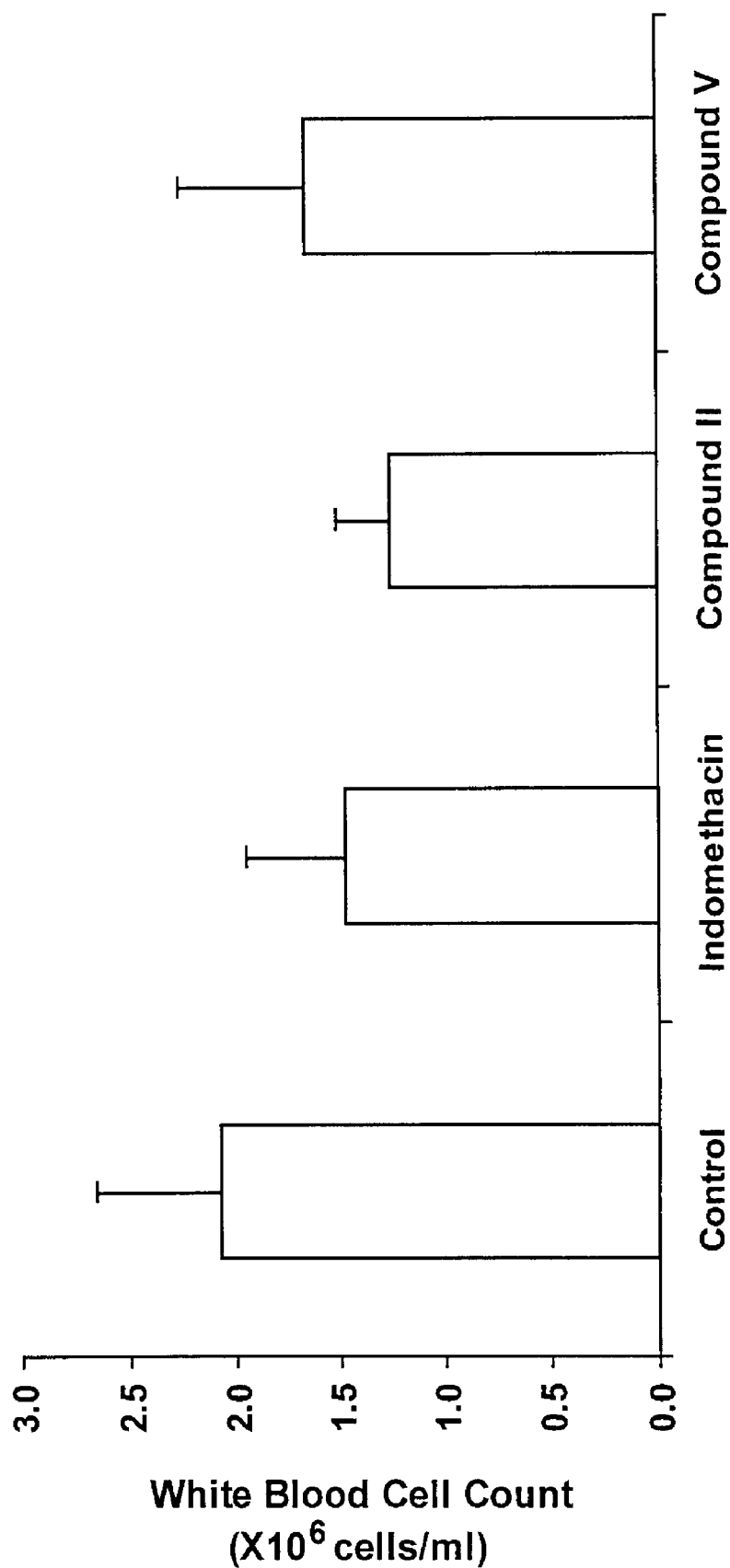
FIG. 19 shows the effect of intravenous administration of compound II or compound V on white blood cell count induced by lipopolysaccharide (LPS).

As shown in FIG. 19, intravenous administration of compound II or compound V induces a significant inhibition of white blood cell count two hours after LPS induction. The differential count of these white blood cells demonstrated more than 90% neutrophils as seen by Wright-Giemsa staining. The inhibition achieved by compound II or V was similar to the one obtained from the positive control indomethacin.

Figure 20A:
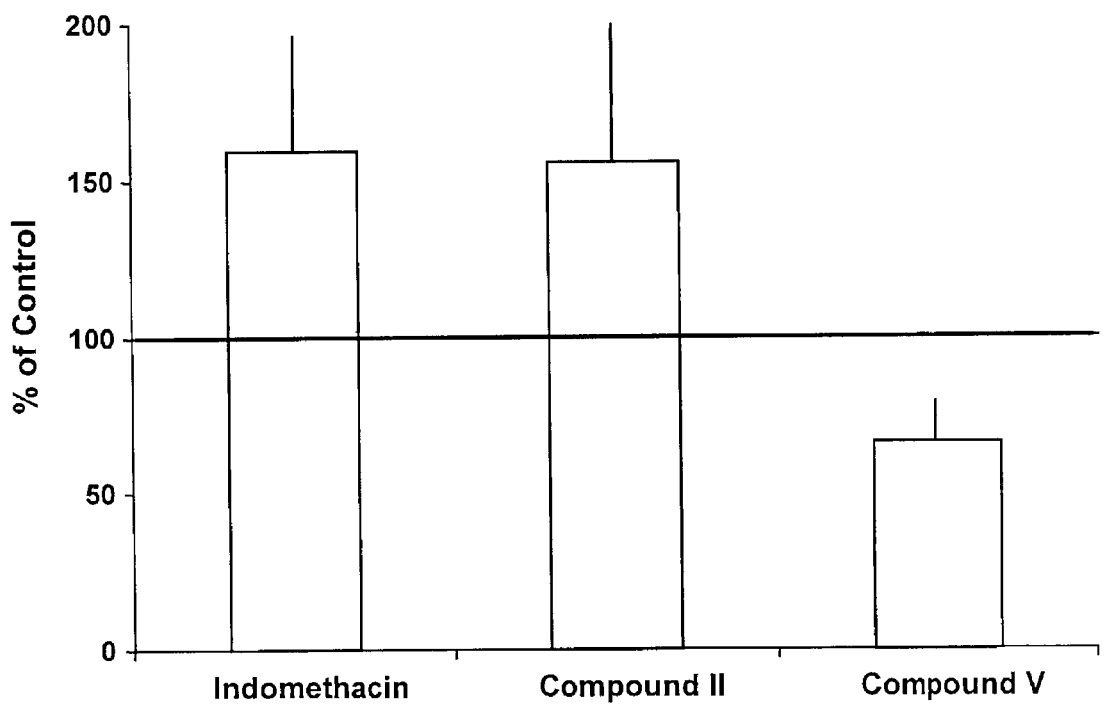
FIG. 20 shows the effect of intravenous administration of compound II or compound V on the production of different soluble mediators in an air-pouch rat model two hours after induction by lipopolysaccharide (LPS): TNFα (FIG. 20A), $PGE_2$ (FIG. 20B), $LTB_4$ (FIG. 20C), or MCP-1 (FIG. 20D).

FIG. 20A shows the effect of intravenous administration of compound II or compound V on $TNF\alpha$ production induced by LPS (two hours after induction) in an air-pouch rat model. Compound V induces a significant inhibition of $TNF\alpha$ production induced by LPS. But either compound II or indomethacin increase the concentration of $TNF\alpha$ after two hours post-LPS induction.

Figure 20B:
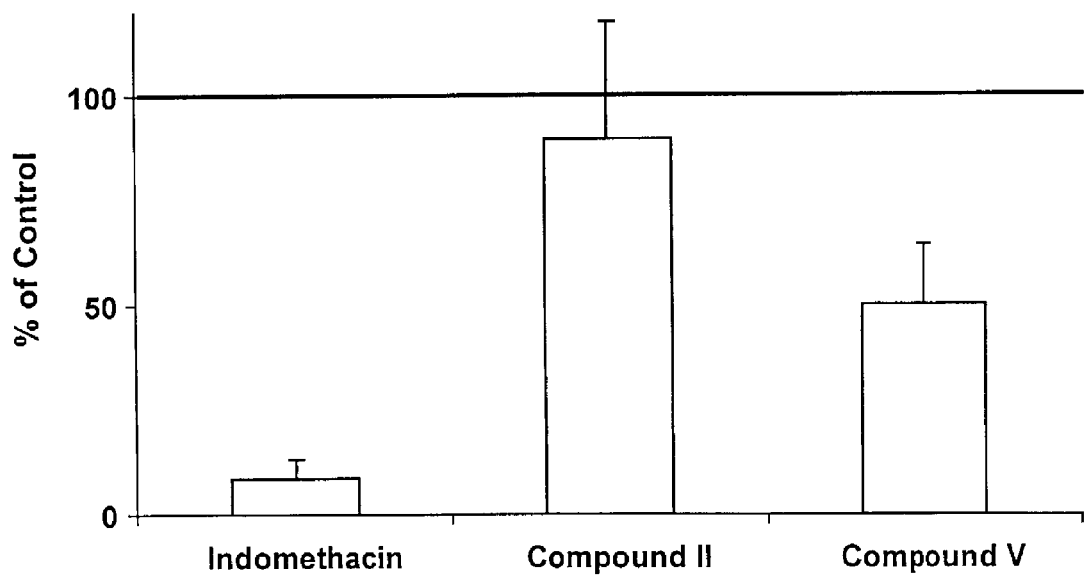

FIG. 20B shows the effect of intravenous administration of compound II or compound V on $PGE_2$ production induced by LPS (two hours after induction) in an air-pouch rat model. Compound V and indomethacin induce a significant inhibition of $PGE_2$ production induced by LPS. But a weak and insignificant inhibition of $PGE_2$ was observed with compound II.

Figure 20C:
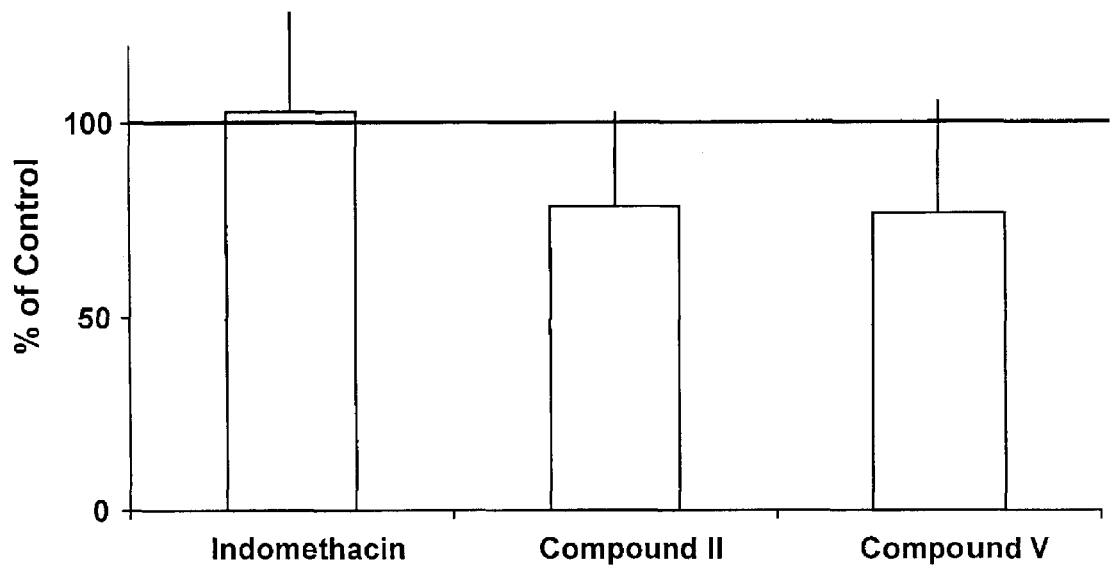

FIG. 20C shows the effect of intravenous administration of compound II or compound V on $LTB_4$ production induced by LPS (two hours after induction) in an air-pouch rat model. Compounds II and V induce a weak inhibition of $LTB_4$ production induced by LPS. But indomethacin did not affect the production of $LTB_4$.

Figure 20D:
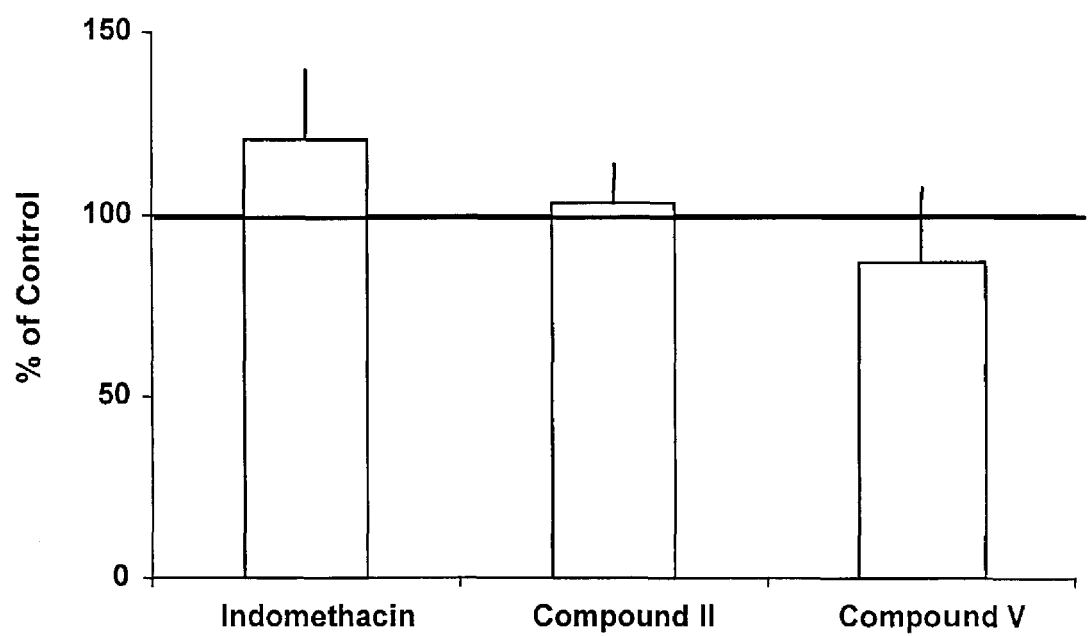

FIG. 20D represents the effect of intravenous administration of compound II or compound V on MCP-1 production induced by LPS (two hours after induction) in an air-pouch rat model. Compound V induces a weak inhibition of MCP-1 production induced by LPS. But indomethacin induces a significant increase while compound II has no influence on MCP-1 presence in the exudates after two hours post-LPS induction.

Figure 21A:
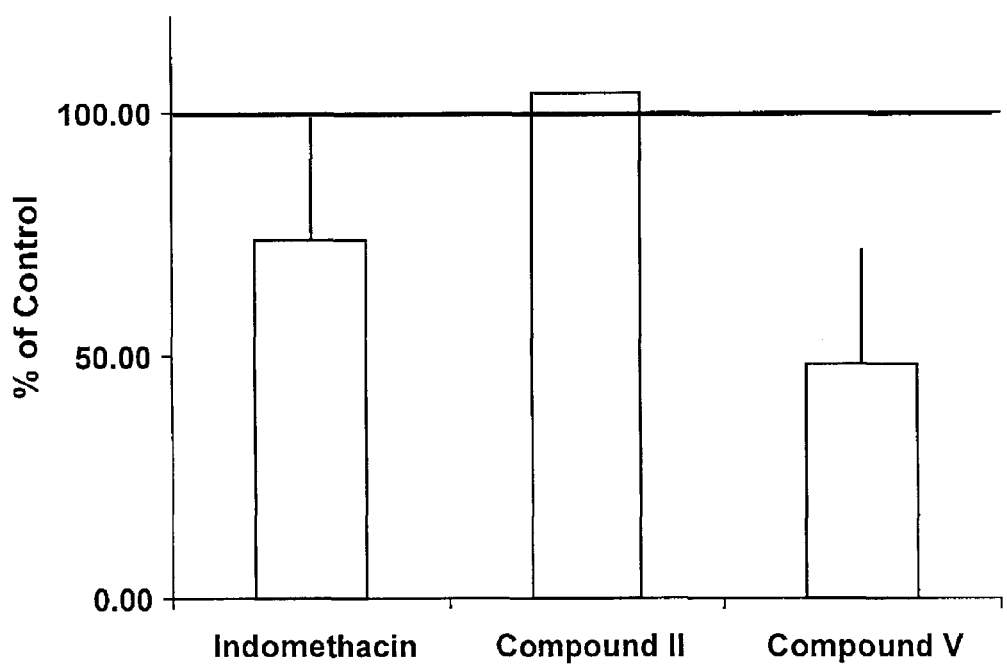
FIG. 21 shows the effect of intravenous administration of compound II or compound V on the production of different soluble mediators in an air-pouch rat model twelve hours after induction by lipopolysaccharide (LPS): TNFα (FIG. 21A) or $PGE_2$ (FIG. 21B).

In another set of experiments, exudates were collected after twelve hours post-LPS induction. FIG. 21A represents the effect of intravenous administration of compound II or compound V on $TNF\alpha$ production induced by LPS. Compound V induces a significant inhibition of $TNF\alpha$ production induced by LPS. But compound II has no effect on the concentration of $TNF\alpha$ in the exudates after twelve hours after post-LPS induction. Indomethacin induces a weak inhibition of $TNF\alpha$ in the exudates after twelve hours post-LPS induction.

Figure 21B:
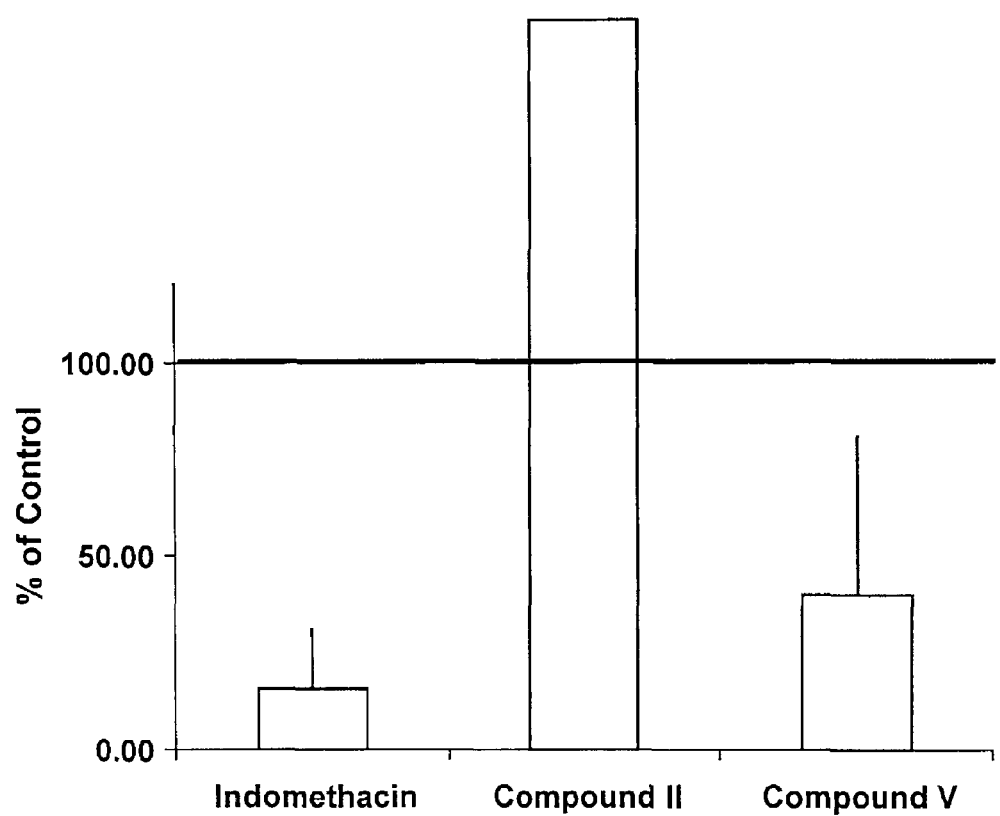

FIG. 21B shows the effect of intravenous administration of compound II or compound V on $PGE_2$ production induced by LPS (twelve hours after induction) in an air-pouch rat model. Compound V or indomethacin induces a significant inhibition of $PGE_2$ production induced by LPS. But a weak and insignificant increase of $PGE_2$ was observed with compound II.

Example 29

Effect of Compound V on DNBS-Induced Colitis

The 2,4-dinitrobenzene sulfonic acid (DNBS) induced experimental colitis mouse model serves as a model of inflammatory bowel disease. On day 0, CD1 mice were sensitized with DNBS by intra-colinic instillation of 0.1 ml of an ethanolic solution (30%) of DNBS (40 mg/ml). Compound V was administered orally once a day for four consecutive days at 25 mg/kg and 50 mg/kg, starting one hour after sensitization with DNBS. On the fourth day, mice were sacrificed and 8 cm of the distal colon was collected and opened longitudinally for macroscopic evaluation.

Compound V induced a weak but significant increase of body weight ($p=0.049$ at 25 mg/kg and $p=0.038$ at 50 mg/kg) compared to the negative control (vehicle) suggesting the treated mice were in better health. Indeed, mortality was observed in the control group but not in the groups treated with compound V.

Figure 22:
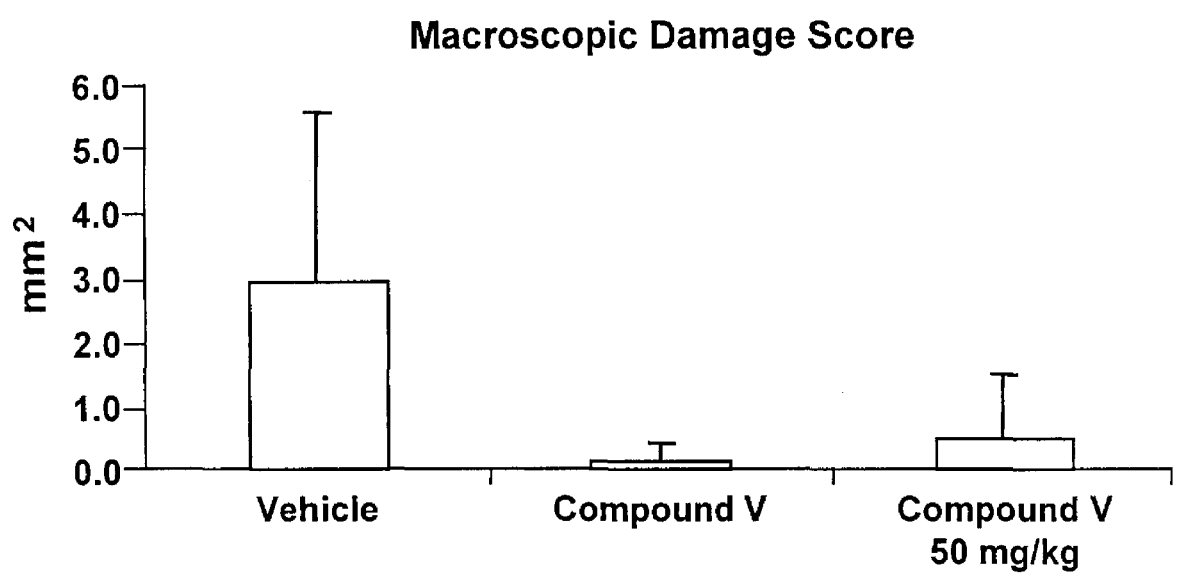
FIG. 22 shows inhibition of distal colon macroscopic damage by compound V.

As shown in FIG. 22, compound V induced a strong and significant decrease in DNBS-induced macroscopic damage area of the colon mucosal tissue ($p=0.003$ at 25 mg/kg and $p=0.012$ at 50 mg/kg) compared to the negative control (vehicle).

Example 30

Effect of Compound V on Experimental Autoimmune Encephalomyelitis

The PLP-induced experimental autoimmune encephalomyelitis (EAE) mouse model serves as a model of multiple sclerosis. On day O, SJL mice were immunized with 75 μg of PLP (139-151) emulsified in Freund's complete adjuvant (200 μl emulsion per mouse s.c. divided among four sites) and with pertussis toxin (200 ng, i.p.). The i.p. injection of pertussis toxin was repeated on day 2. Compound V was administered orally once a day at 25 mg/kg and 50 mg/kg, starting at day 0 and until 30 days post immunization, six times a week.

Figure 23:
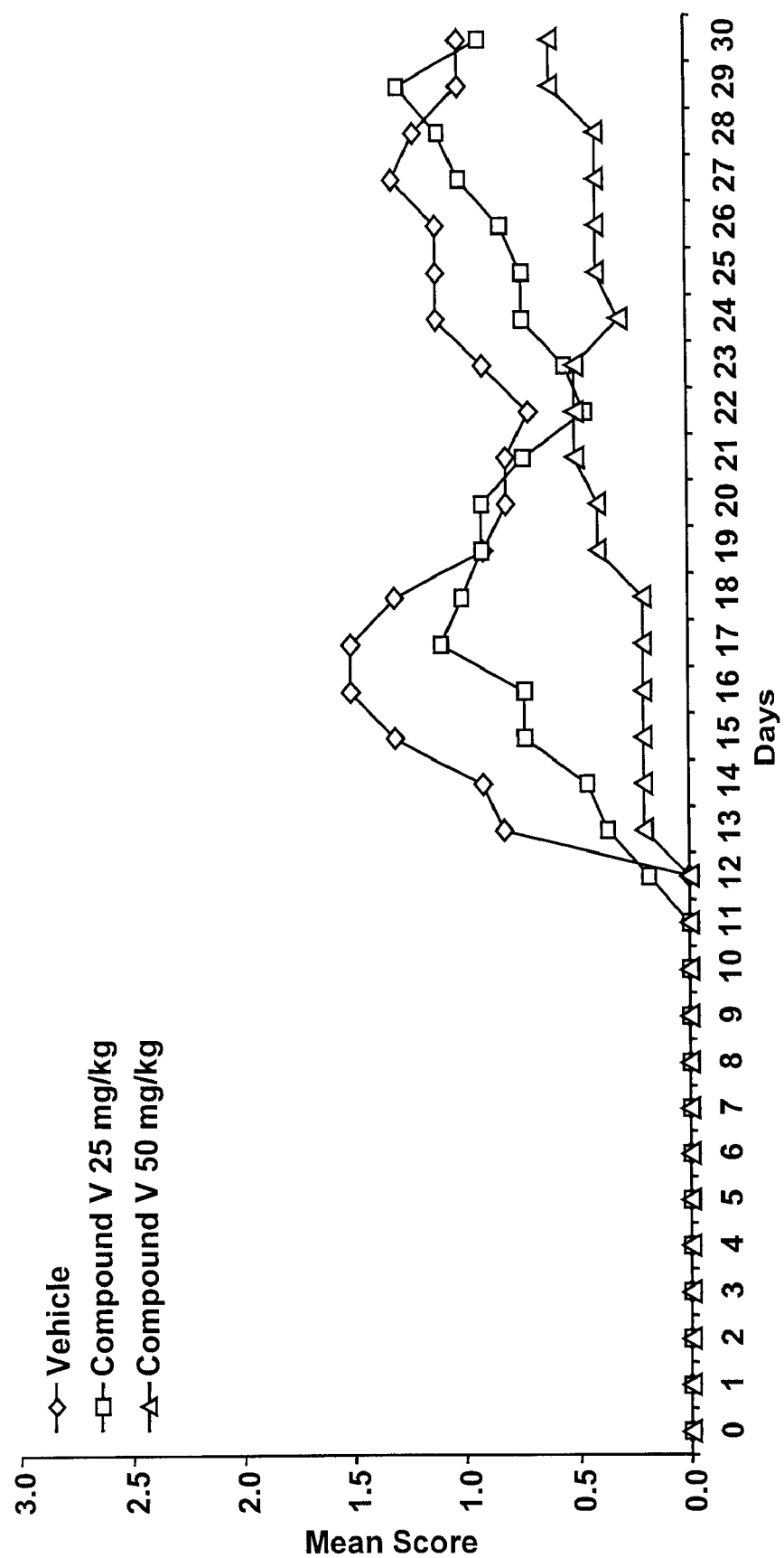
FIG. 23 shows the effect of compound V on clinical signs of experimental autoimmune encephalomyelitis (EAE).

Mice were observed for clinical signs of EAE until 30 days after immunization. Clinical grading of symptoms was carried out according to the following scale: 0=no illness, 1=flaccid tail, 2=moderate paraparesis, 3=severe paraparesis, 4=moribound state, 5=death. As shown in FIG. 23, compound V reduces in a dose dependent manner the appearance of signs of EAE. At 50 mg/kg, compound V displayed a significant activity ($p=0.048$) compared to the negative control (vehicle).

Patents, patent applications, and other publications cited herein are incorporated by reference in their entirety.

All modifications and substitutions that come within the meaning of the claims and the range of their legal equivalents are to be embraced within their scope. A claim using the transition "comprising" allows the inclusion of other elements to be within the scope of the claim; the invention is also described by such claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or inconsequential activities which are ordinarily associated with the invention) instead of the "comprising" term. Any of the three transitions can be used to claim the invention.

It should be understood that an element described in this specification should not be construed as a limitation of the claimed invention unless it is explicitly recited in the claims. Thus, the claims are the basis for determining the scope of legal protection granted instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of the individual elements disclosed herein are considered to be aspects of the invention; similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

What is claimed is:

1. A compound of the following formula:

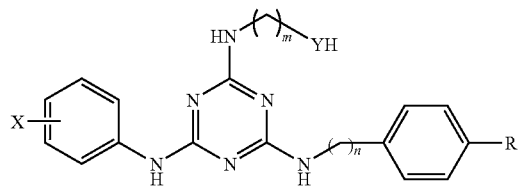

wherein X is F or Cl;

Y is NH, O, or S;

R is $NH_2$, OH, $SO_2NH_2$, $SO_2N(CH_3)H$, $SO_2N(CH_3)_2$, or $CONH_2$;

m is an integer from 2 to 6; and n is an integer from 1 to 2 in which a two-carbon fragment (n =2) includes

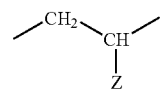

for Z=H or OH.

2. The compound of claim 1, wherein X is F.

3. The compound of claim 1, wherein Y is NH or O.

4. The compound of claim 1, wherein m is 4, 5, or 6.

5. The compound of claim 1, wherein n is 2.

6. The compound of claim 1, wherein R is $NH_2$, OH, $SO_2NH_2$, or $SO_2N(CH_3)_2$.

7. The compound of claim 1, wherein:

X is F;

Y is NH;

R is $NH_2$, OH, $SO_2NH_2$, $SO_2N(CH_3)_2$, or $CONH_2$;

m is 4 or 5; and n is 0 or n is 2 when Z is OH.

8. A compound selected from the group consisting of:

| Compound Structure |
| --- |
| I 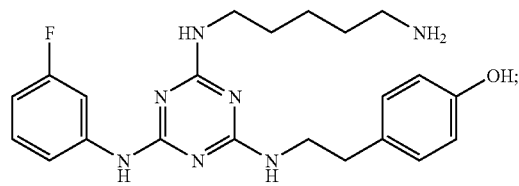 |
| II 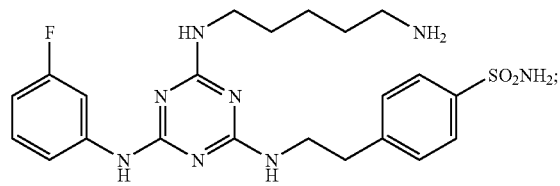 |

-continued
| Compound | Structure |
|---|---|
| III | 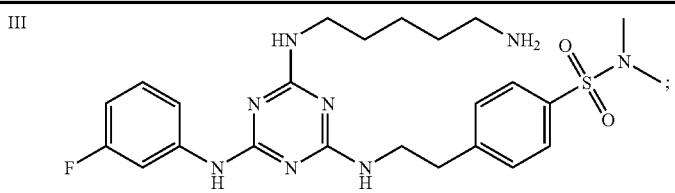 |
| IV | 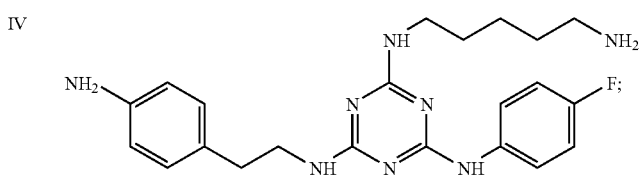 |
| V | 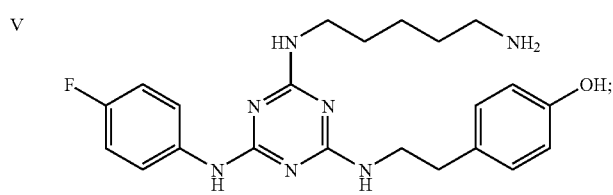 |
| VI | 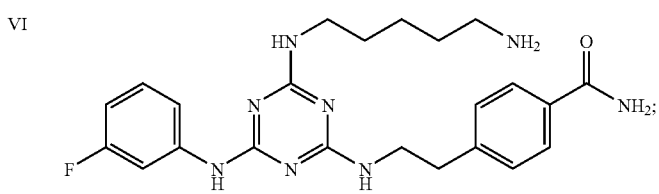 |
| VII | 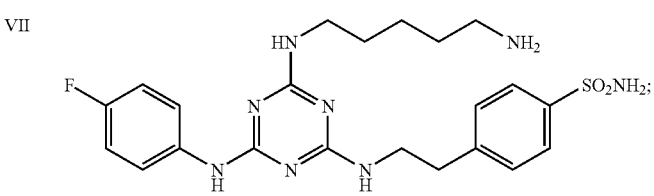 |
| VIII | 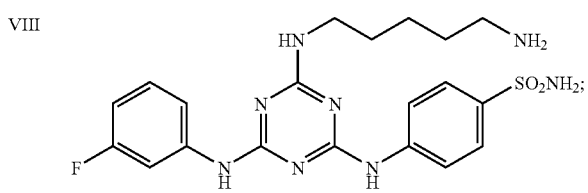 |
| IX | 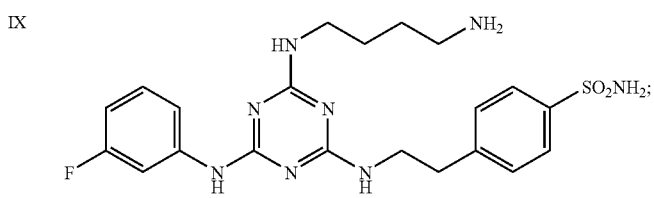 |
| X | 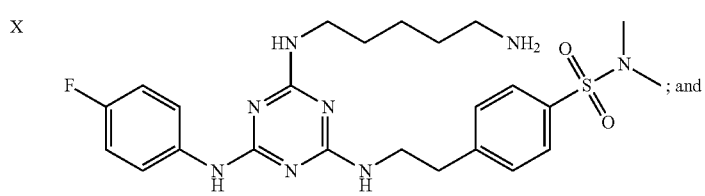 |
| XI | 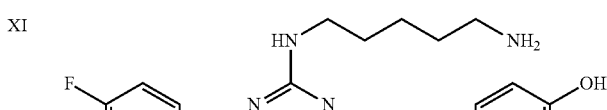 |

9. A pharmaceutical composition comprising a compound according to claim 1 and a pharmaceutically-acceptable carrier.

10. A pharmaceutical composition comprising a compound according to claim 8 and a pharmaceutically-acceptable carrier.

11. The composition of claim 9, wherein the pharmaceutically-acceptable carrier is selected from the group consisting of alcohols, polyol solvents, and aqueous solutions of mono- or disaccharides.

12. The composition of claim 9 further comprising a chemotherapeutic agent.

13. The composition of claim 12, wherein the chemotherapeutic agent is selected from the group consisting of decarbazine, doxorubicin, daunorubicin, cyclophosphamide, vinblastine, vincristine, bleomycin, etoposide, topotecan, irinotecan, taxotere, taxol, 5-fluorouracil, gemcitabine, cisplatin, carboplatin, oxaliplatin, satraplatin, and chlorambucil.

14. The composition of claim 9, further comprising a therapeutic agent blocking binding of TNFα to its receptor or subsequent signal transduction.

15. The composition of claim 14, wherein the therapeutic agent is an anti-TNFα antibody or soluble TNFα receptor.

16. The composition of claim 9, further comprising an agent selected from the group consisting of methotrexate, an anti-inflammatory corticosteroid, a nonsteroidal anti-inflammatory drug, and combinations thereof.

17. A method for the treatment of cancer in a patient in need thereof, wherein said cancer is prostate cancer, mastocytoma, melanoma, breast cancer, lung cancer, or pancreatic cancer, comprising administration to said patient of a therapeutically effective amount of a compound as defined in claim 1.

18. A method for the treatment of an autoimmune disease in a patient in need thereof, wherein said autoimmune disease is rheumatoid arthritis, ankylosing spondylitis, Crohn's disease, psoriasis, Systemic Lupus Erythematosus (SLE), eczema, gout, inflammatory bowel disease, or multiple sclerosis, comprising administration to said patient of a therapeutically effective amount of a compound as defined in claim 1.

19. The method according to claim 18, wherein the autoimmune disease is Crohn's disease, inflammatory bowel disease, or multiple sclerosis.

* * * * *